(12) United States Patent
Su et al.

(10) Patent No.: US 11,154,582 B2
(45) Date of Patent: Oct. 26, 2021

(54) METHOD OF CHINESE HERBAL MEDICINE EXTRACT USED FOR TREATING MULTIPLE DISEASES CAUSED BY DRUG RESISTANT BACTERIA INFECTION

(71) Applicant: SUN YAT-SEN UNIVERSITY, Guangdong (CN)

(72) Inventors: Weiwei Su, Guangdong (CN); Chong Liu, Guangdong (CN); Qian Zhou, Guangdong (CN); Peibo Li, Guangdong (CN); Wei Peng, Guangdong (CN); Yonggang Wang, Guangdong (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 650 days.

(21) Appl. No.: 15/920,480

(22) Filed: Mar. 14, 2018

(65) Prior Publication Data

US 2018/0200319 A1    Jul. 19, 2018

Related U.S. Application Data

(63) Continuation of application No. PCT/CN2017/071671, filed on Jan. 19, 2017.

(30) Foreign Application Priority Data

| May 10, 2016 | (CN) | .......................... 201610308207.4 |
| May 10, 2016 | (CN) | .......................... 201610308716.7 |
| May 10, 2016 | (CN) | .......................... 201610308717.1 |
| May 10, 2016 | (CN) | .......................... 201610308718.6 |

(51) Int. Cl.
*A61K 36/48* (2006.01)

(52) U.S. Cl.
CPC ........ *A61K 36/48* (2013.01); *A61K 2236/331* (2013.01); *Y02A 50/30* (2018.01)

(58) Field of Classification Search
None
See application file for complete search history.

(56) References Cited

FOREIGN PATENT DOCUMENTS

| CN | 1718222 A | 1/2006 |
| CN | 103385912 A | 11/2013 |
| GN | 101032547 A | 9/2007 |

OTHER PUBLICATIONS

Machine translation of CN103385912A (published Nov. 13, 2013; machine translation from Google Patents). (Year: 2013).*
International Search Report of PCT Patent Application No. PCT/CN2017/071671 dated Apr. 20, 2017.
Sha, Jingshu et al., Pitecollobium Clypearia Benth, Chinese Pharmaceutical Bulletin, Nov. 30, 1986, p. 665, vol. 21, No. 11.

* cited by examiner

Primary Examiner — Michael Barker

(57) ABSTRACT

Disclosed is a new drug application of a *Pithecellobium Clypearia* Benth Extract (EA), and particularly is a method of the EA used for treating multiple diseases caused by drug resistant bacteria infection. Related drug resistant bacteria include a Multi-Drug Resistant (MDR) *Acinetobacter Baumannii* (MDRAB), an MDR *Pseudomonas Aeruginosa* (MDRPA), an Extended-Spectrum Beta-Lactamase (ESBL) producing *Escherichia Coli* (ECO) and an ESBL-producing *Klebsiella Pneumonia* (KPN).

3 Claims, No Drawings

METHOD OF CHINESE HERBAL MEDICINE EXTRACT USED FOR TREATING MULTIPLE DISEASES CAUSED BY DRUG RESISTANT BACTERIA INFECTION

CROSS-REFERENCE TO RELATED APPLICATIONS

The present application is a continuation application of PCT application No. PCT/CN2017/071671 filed on Jan. 19, 2017, which claims the benefit of Chinese patent application Nos. 201610308716.7, 201610308717.1, 201610308207.4 and 201610308718.6, each filed on May 10, 2016. The contents of all of the above are hereby incorporated by reference.

TECHNICAL FIELD

The present disclosure relates to a new drug application of a *Pithecellobium Clypearia* Benth Extract (EA), and particularly, to a method of the EA used for treating multiple diseases caused by drug resistant bacteria infection.

BACKGROUND

The twenty-first century is an age of Multi-Drug Resistant (MDR) bacteria. After 60 years of clinical use of an antibiotic, more and more hospital infections and infections with the MDR bacteria have become a major challenge to clinical antibacterial treatment at present. Since a first case of clinical Methicillin-Resistant *Staphylococcus Aureus* (MRSA) infected patient was reported by Jerons in 1961, the MRSA infections have gradually spread all over the world till now. In 2011, China Bacterial Resistance Surveillance in clinic showed that, in distribution of main drug resistant bacteria, *escherichia coli* and *klebsiella pneumonia* produced Extended-Spectrum Beta-Lactamase (ESBL) strains respectively were 50.7% and 38.5%, and the transition and current status of the drug resistance thereof are highly concerned. In addition, according to an annual report 2010 from a Drug Resistance Surveillance Cooperating Group of Ministry of Health, pathogenic bacteria separated by *acinetobacter baumannii* and *pseudomonas aeruginosa* in a hospital ICU ranked the top, and the drug resistance rates of the *acinetobacter baumannii* to imipenem (IMP) and meropenem respectively were up to 60.4% and 61.4%. To sum up, in various MRSA and ESBL produced bacteria, the clinical occupied rates of the MDR *Acinetobacter Baumannii* (MDRAB) and *Pseudomonas Aeruginosa* (MDRPA) have been growing every year. Under the pressure that the drug resistance rates are rising continuously, the antibiotic treatment is facing an enormous challenge. In order to prevent further deterioration of a bacterial drug resistant phenomenon, experts and scholars are sparing no effort to discover a new method for inhibiting bacterial growth and treating a bacteria-induced disease. A research has been reported and proved that traditional Chinese herbal medicines such as *Coptis chinensis, Scutellaria baicalensis* and *Forsythia suspensa* have a certain inhibition effect to different drug resistant bacteria. The key to further research the Chinese herbal medicine to inhibit the growth of the drug resistant bacteria is to discover a new Chinese herbal medicine with a stronger bactericidal capacity and a wider drug resistant inhibitory spectrum.

With *Pithecellobium bigemimum* (L.) Benth as a scientific name, the *Pithecellobium clypearia* Benth is dry young branches and leaves of *mimosa pithecellobium* plant that is the *Pithecellobium clypearia* Benth. It is cold, tastes bitter and has the effects of clearing away heat and toxic materials, astringing dampness and healing sore. It is a unique southern medicinal material for treating multiple heat toxin symptoms.

Currently, there has disclosed in a literature that the *Pithecellobium clypearia* Benth and an extract thereof have an antiviral effect, but lacks a research in an effect of the *Pithecellobium clypearia* Benth and the extract thereof in aspect of anti-drug resistant bacteria.

SUMMARY

In order to overcome the above defects, the present disclosure discloses an application of an EA in preparing a drug resistant bacteria resistant drug and in an aspect of a sensibilization effect by using with a similar antibiotic thereof, specifically:

1. a method of the EA used for treating disease caused by an MDRAB resistant infection, in which the EA is used with an antibiotic IMP or Tetracycline (TE) or Polymycin B (POLB) or Ceftazidime (CAZ) or Levofloxacin (LVX) and all show an obvious sensibilization effect;

2. a method of the EA used for treating disease caused by an MDRPA resistant infection, in which the EA is used with an antibiotic LVX or IMP or Amikacin (AMK) or CAZ or Cefoperazone (CFP) and all show an obvious sensibilization effect;

3. a method of the EA used for treating disease caused by an ESBL-producing *Escherichia Coli* (ECO) resistant infection, in which the EA is used with an antibiotic AMK or Compound Sulfamethoxazole (SXT) and all show an obvious sensibilization effect;

4. a method of the EA used for treating disease caused by an ESBL-producing *Klebsiella Pneumonia* (KPN) resistant infection, in which the EA shows an obvious inhibitory effect to the ESBL-producing KPN.

The EA preferably is a *Pithecellobium clypearia* Benth water extract or a *Pithecellobium clypearia* Benth ethanol extract.

A method for preparing the EA is as follows: extracting *Pithecellobium clypearia* Benth coarse powder with water or an ethanol aqueous solution having a concentration of 10%-95% by a volume ratio, and then extracting an obtained extracting solution with ethyl acetate, in which the obtained extract is a final product. The ethanol aqueous solution preferably is an ethanol aqueous solution having the concentration of 60% by the volume ratio.

In the present disclosure, the drug includes a human drug or an animal drug, or a soil treatment drug or preparation.

The present disclosure achieves the following beneficial effects.

The present disclosure first discloses the antibacterial effect of the EA to the MDRAB, the MDRPA, the ESBL-producing ECO and the ESBL-producing KPN and the sensibilization effect by using with the antibiotics thereof.

A test proves that the EA by using with the IMP or the TE or the POLB or the CAZ or the LVX has a synergistic effect to the MDRA resistance, and compared with the single use, the usage of the antibiotic is reduced by 50%-87%.

The EA by using with the LVX or the IMP or the AMK or the CAZ or the CFP has a synergistic effect to the MDRPA resistance, and compared with the single use, the usage of the antibiotic is reduced by 50%-99.2%.

The EA by using with the AMK or the SXT has a synergistic effect to the ESBL-producing ECO, and compared with the single use, the usage of the antibiotic is reduced by 75%-99.3%.

The EA in the present disclosure can be taken as a natural antibacterial drug for the above drug resistant bacteria or a sensitizer similar to the antibiotic, and is applied to treatment of a disease caused by the above bacteria. The present disclosure provides a new way and a replacement drug to solve the drug resistant problem of the antibiotics, and is applied to the human drug, other animal drugs and soil remediation of corresponding infectious bacteria. It is a natural plant extract and has no side effect, and the extracting method is simple and environment-friendly.

DETAILED DESCRIPTION OF THE EMBODIMENTS

The EA to resist the drug resistant bacteria and the pharmacological actions of the sensibilization effect to similar antibiotics will be further described with the reference to the following implementation solutions.

Preparation of the EA: the *Pithecellobium clypearia* Benth is provided by Guangzhou Huacheng Pharmaceutical Factory. An appropriate amount of *Pithecellobium clypearia* Benth medicinal materials are taken and are crushed into coarse powder; the coarse powder is reflowed for two times with water or with a 10%-95% ethanol aqueous solution, each time for 2 h, and is filtered; filtrates are merged and are condensed to obtain an extractum (namely, the *Pithecellobium clypearia* Benth water or ethanol extract); after being taken and suspended in the water, the extractum is extracted with ethyl acetate for three times, and ethyl acetate extracting solutions are merged and are condensed to obtain an ethyl acetate extract. The extract obtained by reflowing with a 10% ethanol aqueous solution is referred to as a *Pithecellobium clypearia* Benth 10% ethanol extract, and the extract obtained by reflowing with other concentrations of ethanol aqueous solutions are by that analogy.

Strains: test strains in the present disclosure all are provided by the Clinical Microbiology Lab of Department of Lab Medicine at First Affiliated Hospital of Sun Yat-Sen University and the drug resistance is tested and confirmed by the same.

*Mycoplasma Hominis* (MH) broth culture medium: 2.1 g of MH broth dry powder (British OXOID LTD.) is taken and a volume is fixed to 100 ml; the pH is adjusted to 7.0 with NAOH; and the culture medium is sterilized at a high pressure and is placed into a refrigerator at 4° C. for later use.

Determination methods of a Minimal Inhibitory Concentration (MIC) and a Minimum Bactericidal Concentration (MBC) of a test product: the MIC and the MBC of the *Pithecellobium clypearia* Benth water or ethanol extract to the MDRAB are determined by a microdilution broth method. And it is operated by referring to the microdilution broth method recommended by National Committee for Clinical Laboratory Standards (NCCLS).

Test methods of the sensibilization effects of the test product to similar antibiotics: it is operated by referring to a checkerboard assay recommended by NCCLS.

I. Inhibitory and bactericidal tests of MDRA resistance of the EA and test of the sensibilization effect by respectively using with the IMP or the TE or the POLB or the CAZ or the LVX Embodiment 1

1. Test Method
1) MIC Determination

The EA, the IMP, the TE, the POLB, the CAZ and the LVX are respectively diluted in the MH broth culture medium by a series of ratios, with each pore for 50 μl; the inoculant bacteria are adjusted to $1.0*10^6$ CFU/ml and 50 μl of a bacteria solution is added to each pore; the culture is at 35° C. and for 24 h; and the concentration, at which no precipitate occurs, of a minimum antibacterial drug is the MIC.

2) MBC Determination

A spread plate count method is adopted. 50 μl of bacterial suspension is absorbed from a pore for sterile growth in item 1) to a blood plate, is uniformly coated and is cultured for 24 h at 35° C. Bacterial colonies are counted, and the concentration, at which the initial number of experimental viable bacteria is reduced by 99.9% or more, of the minimum antibacterial drug is the MBC.

By determining the MIC and the MBC of the drug and making statistics of the data to obtain $MIC_{50}$, $MIC_{90}$, $MBC_{50}$ and $MBC_{90}$, the effect of the MDRA resistance of the drug is evaluated.

3) Checkerboard Assay

The checkerboard assay is performed in a 96-pore sterile culture plate. The EA, the IMP, the TE, the POLB and the CAZ are respectively diluted into a series of concentrations in a doubling manner in the MH broth culture medium, and two drugs are combined respectively at ¼MIC to 4 MIC; 25 μl of A drug and 25 μl of B drug are respectively added to each pore, the concentration of the bacterial suspension is adjusted to $1.0*10^6$ CFU/ml, 50 μl of the bacteria solution is inoculated to each pore and is cultured for 24 h at 35° C.; and then, the MIC to the MDRAB after the A drug is used with the B drug is observed.

Calculation of a Fractional Inhibitory Concentration (FIC): FIC=S20b combined-use MIC/S20b single-use MIC+ antibiotic combined-use MIC/antibiotic single-use MIC. By calculating the FIC, the combined antibacterial interaction between the EA and the antibiotic is evaluated, with synergistic effect for FIC≤0.5, additive effect for 0.5<FIC≤1, indifferent effect for 1<FIC≤2 and antagonistic effect for FIC>2. According to a sterile growth pore, the optimum concentration ratio between the EA and the antibiotic is founded out. At last, the effect of the EA to strengthen the efficacy of the antibiotic is evaluated.

The test products in the embodiment include: the *Pithecellobium clypearia* Benth water extract, the *Pithecellobium clypearia* Benth 10% ethanol extract, the *Pithecellobium clypearia* Benth 60% ethanol extract and the *Pithecellobium clypearia* Benth 95% ethanol extract.

The MDRABs are numbered as A1-A20.

2. Test Results 2.1 In-vitro inhibitory test results of the *Pithecellobium clypearia* Benth water extract and the five antibiotics (the IMP, the TE, the POLB, the CAZ and LVX) to the MDRABs are shown in table A1.

In-vitro bactericidal test results of the *Pithecellobium clypearia* Benth water extract to the MDRABs are shown in table A2.

The statistic analysis on in-vitro inhibitory and bactericidal $MIC_{50}$ and $MIC_{90}$ of the *Pithecellobium clypearia* Benth water extract and the five antibiotics to the MDRABs is shown in table A3.

The statistic analysis on $MBC_{50}$ and $MBC_{90}$ of the *Pithecellobium clypearia* Benth water extract to the MDRABs is shown in table A4.

FIC values of a combined drug sensitive test of the *Pithecellobium clypearia* Benth water extract and the five antibiotics and distribution statistical results of the FIC values are shown in table A5 and table A6.

The sensibilization effects of the *Pithecellobium clypearia* Benth water extract to the five antibiotics and the $MIC_{50}$ and $MIC_{90}$ after combined use are shown in tables A7-A12.

TABLE A1

In-vitro inhibitory test results of the *Pithecellobium clypearia* Benth water extract and the five antibiotics to the MDRABs

| Strain No. | MIC (µg/ml) | | | | | |
|---|---|---|---|---|---|---|
| | EA | IMP | TE | LVX | CAZ | POLB |
| A1 | 600 | 1 | 2 | 0.5 | 128 | 8 |
| A2 | 600 | 32 | 256 | 16 | 512 | 2 |
| A3 | 600 | 32 | 256 | 4 | 512 | 2 |
| A4 | 600 | 8 | 8 | 0.5 | 256 | 2 |
| A5 | 600 | 32 | 32 | 4 | 64 | 4 |
| A6 | 600 | 32 | 256 | 8 | >512 | 8 |
| A7 | 600 | 32 | 512 | 8 | >512 | 4 |
| A8 | 600 | 32 | 256 | 4 | 512 | 8 |
| A9 | 600 | 32 | 256 | 4 | 512 | 1 |
| A10 | 600 | 16 | 128 | 32 | 512 | 32 |
| A11 | 600 | 32 | 256 | 4 | 512 | 16 |
| A12 | 600 | 32 | 512 | 32 | 512 | 2 |
| A13 | 600 | 32 | 512 | 32 | 256 | 2 |
| A14 | 600 | 32 | 256 | 16 | 512 | 0.5 |
| A15 | 1200 | 32 | >512 | 32 | 256 | 2 |
| A16 | 600 | 32 | 512 | 8 | 512 | 4 |
| A17 | 600 | 16 | 512 | 16 | 256 | 64 |
| A18 | 600 | 32 | 512 | 8 | 512 | 4 |
| A19 | 600 | 32 | 512 | 16 | 256 | 4 |
| A20 | 600 | 32 | 256 | 16 | 512 | 2 |
| ATCC27853 | 300 | 1 | 8 | 1 | 4 | 1 |

TABLE A2

In-vitro bactericidal test results of the *Pithecellobium clypearia* Benth water extract to the MDRABs

| Strain No. | MBC (µg/ml) |
|---|---|
| A1 | 1200 |
| A2 | 1200 |
| A3 | 1200 |
| A4 | 1200 |
| A5 | 1200 |
| A6 | 1200 |
| A7 | 1200 |
| A8 | 1200 |
| A9 | 1200 |
| A10 | 1200 |
| A11 | 1200 |
| A12 | 1200 |
| A13 | 1200 |
| A14 | 1200 |
| A15 | 2400 |
| A16 | 1200 |
| A17 | 1200 |
| A18 | 1200 |
| A19 | 1200 |
| A20 | 1200 |

TABLE A3

Statistical results on in-vitro inhibitory $MIC_{50}$ and $MIC_{90}$ of the *Pithecellobium clypearia* Benth water extract and the antibiotics to the MDRABs

| | MIC (µg/ml) | | |
|---|---|---|---|
| Drug | Range | $MIC_{50}$ | $MIC_{90}$ |
| EA | 600-1200 | 600 | 600 |
| IMP | 1-32 | 32 | 32 |
| TE | 2-512 | 256 | 512 |
| POLB | 0.5-64 | 4 | 16 |
| CAZ | 64-512 | 512 | 512 |
| LVX | 0.5-32 | 8 | 32 |

TABLE A4

Bactericidal $MIC_{50}$ and $MIC_{90}$ of the *Pithecellobium clypearia* Benth water extract to the MDRABs

| | MBC (µg/ml) | | |
|---|---|---|---|
| Drug | Range | $MBC_{50}$ | $MBC_{90}$ |
| EA | 1200-2400 | 1200 | 1200 |

TABLE A5

FIC values of the combined drug sensitive test of the *Pithecellobium clypearia* Benth water extract and the five antibiotics

| Strain No. | FIC | | | | |
|---|---|---|---|---|---|
| | EA + IMP | EA + TE | EA + POLB | EA + CAZ | EA + LVX |
| A1 | 1 | 1 | 1.5 | 0.75 | 0.625 |
| A2 | 1 | 1 | 1 | 1 | 1.5 |
| A3 | 1 | 0.75 | 1.25 | 0.75 | 0.375 |
| A4 | 0.625 | 0.75 | 0.5 | 0.625 | 0.375 |
| A5 | 1.5 | 0.375 | 0.375 | 1 | 0.5 |
| A6 | 1 | 0.5 | 0.5 | 1 | 1 |
| A7 | 1 | 1 | 0.75 | 1 | 1 |
| A8 | 1 | 1 | 1.007813 | 1 | 1.25 |
| A9 | 1.5 | 0.75 | 1.0625 | 0.375 | 0.265625 |
| A10 | 1 | 1.5 | 0.5 | 1 | 0.75 |
| A11 | 1.25 | 0.75 | 0.5 | 1 | 1 |
| A12 | 1 | 0.75 | 1.03125 | 0.5 | 0.5625 |
| A13 | 1.5 | 0.5 | 1.5 | 1 | 0.75 |
| A14 | 0.375 | 0.375 | 0.625 | 0.375 | 1 |
| A15 | 0.375 | 0.3125 | 0.53125 | 1 | 0.501953 |
| A16 | 0.5 | 0.625 | 0.515625 | 1.125 | 0.5 |
| A17 | 0.375 | 1.25 | 1.03125 | 0.625 | 1 |
| A18 | 0.375 | 0.75 | 1.5 | 1 | 0.375 |
| A19 | 0.5 | 0.375 | 1 | 1 | 1 |
| A20 | 0.5 | 0.5 | 1 | 0.375 | 0.5 |

TABLE A6

Distribution statistics of the FIC values of the combined drug sensitive test of the *Pithecellobium clypearia* Benth water extract and the five antibiotics

| FIC_Range | EA + IMP | EA + TE | EA + POLB | EA + CAZ | EA + LVX |
|---|---|---|---|---|---|
| FIC ≤ 0.5 | 35% | 35% | 25% | 20% | 35% |
| 0.5 < FIC ≤ 1 | 45% | 55% | 35% | 75% | 55% |
| 1 < FIC ≤ 2 | 20% | 10% | 40% | 5% | 10% |
| FIC > 2 | — | — | — | — | — |

TABLE A7

Sensibilization effect of the *Pithecellobium clypearia* Benth water extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
|---|---|---|---|---|
| A1  | 600  | 300  | 1  | 0.5 |
| A2  | 600  | 300  | 32 | 16  |
| A3  | 600  | 300  | 32 | 16  |
| A4  | 600  | 300  | 8  | 1   |
| A5  | 600  | 600  | 32 | 16  |
| A6  | 600  | 300  | 32 | 16  |
| A7  | 600  | 300  | 32 | 16  |
| A8  | 600  | 300  | 32 | 16  |
| A9  | 600  | 600  | 32 | 16  |
| A10 | 600  | 300  | 16 | 8   |
| A11 | 600  | 600  | 32 | 8   |
| A12 | 600  | 300  | 32 | 16  |
| A13 | 600  | 600  | 32 | 16  |
| A14 | 600  | 150  | 32 | 4   |
| A15 | 1200 | 300  | 32 | 4   |
| A16 | 600  | 150  | 32 | 8   |
| A17 | 600  | 150  | 16 | 2   |
| A18 | 600  | 75   | 32 | 8   |
| A19 | 600  | 150  | 32 | 8   |
| A20 | 600  | 150  | 32 | 8   |

TABLE A8

Sensibilization effect of the *Pithecellobium clypearia* Benth water extract to the TE and MIC after combined use

| Strain No. | EA single-use MIC (μg/ml) | EA combined-use MIC (μg/ml) | TE single-use MIC (μg/ml) | TE combined-use MIC (μg/ml) |
|---|---|---|---|---|
| A1  | 600  | 300 | 2    | 1   |
| A2  | 600  | 300 | 256  | 128 |
| A3  | 600  | 300 | 256  | 64  |
| A4  | 600  | 300 | 8    | 2   |
| A5  | 600  | 150 | 32   | 4   |
| A6  | 600  | 150 | 256  | 64  |
| A7  | 600  | 300 | 512  | 256 |
| A8  | 600  | 300 | 256  | 128 |
| A9  | 600  | 300 | 256  | 64  |
| A10 | 600  | 600 | 128  | 64  |
| A11 | 600  | 300 | 256  | 64  |
| A12 | 600  | 150 | 512  | 256 |
| A13 | 600  | 150 | 512  | 128 |
| A14 | 600  | 150 | 256  | 32  |
| A15 | 1200 | 300 | 1024 | 64  |
| A16 | 600  | 300 | 512  | 64  |
| A17 | 600  | 600 | 512  | 128 |
| A18 | 600  | 300 | 512  | 128 |
| A19 | 600  | 150 | 512  | 64  |
| A20 | 600  | 150 | 256  | 64  |

TABLE A9

Sensibilization effect of the *Pithecellobium clypearia* Benth water extract to the POLB and MIC after combined use

| Strain No. | EA single-use MIC (μg/ml) | EA combined-use MIC (μg/ml) | POLB single-use MIC (μg/ml) | POLB combined-use MIC (μg/ml) |
|---|---|---|---|---|
| A1  | 600  | 600 | 8  | 4      |
| A2  | 600  | 300 | 2  | 1      |
| A3  | 600  | 600 | 2  | 0.5    |
| A4  | 600  | 150 | 2  | 0.5    |
| A5  | 600  | 150 | 4  | 0.5    |
| A6  | 600  | 150 | 8  | 2      |
| A7  | 600  | 300 | 4  | 1      |
| A8  | 600  | 600 | 8  | 0.0625 |
| A9  | 600  | 600 | 1  | 0.0625 |
| A10 | 600  | 150 | 32 | 8      |
| A11 | 600  | 150 | 16 | 4      |
| A12 | 600  | 600 | 2  | 0.0625 |
| A13 | 600  | 600 | 2  | 1      |
| A14 | 600  | 300 | 0.5| 0.0625 |
| A15 | 1200 | 600 | 2  | 0.0625 |
| A16 | 600  | 300 | 4  | 0.0625 |
| A17 | 600  | 600 | 64 | 2      |
| A18 | 600  | 600 | 4  | 2      |
| A19 | 600  | 300 | 4  | 2      |
| A20 | 600  | 300 | 2  | 1      |

TABLE A10

Sensibilization effect of the *Pithecellobium clypearia* Benth water extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| A1  | 600  | 150 | 128  | 64  |
| A2  | 600  | 300 | 512  | 256 |
| A3  | 600  | 150 | 512  | 256 |
| A4  | 600  | 300 | 256  | 32  |
| A5  | 600  | 300 | 64   | 32  |
| A6  | 600  | 300 | 1024 | 512 |
| A7  | 600  | 300 | 1024 | 512 |
| A8  | 600  | 300 | 512  | 256 |
| A9  | 600  | 150 | 512  | 64  |
| A10 | 600  | 300 | 512  | 256 |
| A11 | 600  | 300 | 512  | 256 |
| A12 | 600  | 150 | 512  | 128 |
| A13 | 600  | 300 | 256  | 128 |
| A14 | 600  | 150 | 512  | 64  |
| A15 | 1200 | 600 | 256  | 128 |
| A16 | 600  | 600 | 512  | 64  |
| A17 | 600  | 300 | 256  | 32  |
| A18 | 600  | 300 | 512  | 256 |
| A19 | 600  | 300 | 256  | 128 |
| A20 | 600  | 150 | 512  | 64  |

TABLE A11

Sensibilization effect of the *Pithecellobium clypearia* Benth water extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| A1  | 600  | 300 | 0.5 | 0.0625 |
| A2  | 600  | 300 | 16  | 16     |
| A3  | 600  | 150 | 16  | 2      |
| A4  | 600  | 150 | 0.5 | 0.0625 |
| A5  | 600  | 150 | 4   | 1      |
| A6  | 600  | 300 | 8   | 4      |
| A7  | 600  | 300 | 8   | 4      |
| A8  | 600  | 150 | 4   | 4      |
| A9  | 600  | 150 | 4   | 0.0625 |
| A10 | 600  | 300 | 32  | 8      |
| A11 | 600  | 300 | 4   | 2      |
| A12 | 600  | 300 | 32  | 2      |
| A13 | 600  | 300 | 32  | 8      |
| A14 | 600  | 300 | 16  | 8      |
| A15 | 1200 | 600 | 32  | 0.0625 |
| A16 | 600  | 150 | 8   | 2      |

TABLE A11-continued

Sensibilization effect of the *Pithecellobium clypearia*
Benth water extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| A17 | 600 | 300 | 16 | 8 |
| A18 | 600 | 150 | 8 | 1 |
| A19 | 600 | 300 | 16 | 8 |
| A20 | 600 | 150 | 16 | 4 |

TABLE A12

$MIC_{50}$ and $MIC_{90}$ of the five antibiotics after combined use

| Combined drug | Antibiotic (μg/ml) | |
|---|---|---|
| | $MIC_{50}$ after combined use | $MIC_{90}$ after combined use |
| EA + IMP | 8 | 16 |
| EA + TE | 64 | 128 |
| EA + POLB | 1 | 4 |
| EA + CAZ | 128 | 256 |
| EA + LVX | 2 | 8 |

With the single use of the *Pithecellobium clypearia* Benth water extract to the MDRABs, the $MIC_{50}$ is 600 μg/ml, the $MIC_{90}$ is 600 μg/ml, the $MBC_{50}$ is 1200 μg/ml, and the $MBC_{90}$ is 1200 μg/ml.

It is indicated by FIC≤1 with the combined use of the *Pithecellobium clypearia* Benth water extract and the IMP that the two drugs have the synergistic effect or partial synergistic effect, wherein 35% with FIC≤0.5 have the synergistic effect. For the 20 MDRABs, when the concentration of the *Pithecellobium clypearia* Benth water extract is smaller than or equal to the single-use MIC, the $MIC_{50}$ of the IMP is reduced from single-use 32 μg/ml to 8 μg/ml and is reduced by 75%; and the $MIC_{90}$ is reduced from 32 μg/ml to 16 μg/ml and is reduced by 50%.

It is indicated by FIC≤1 with the combined use of the *Pithecellobium clypearia* Benth water extract and the TE to the 20 MDRABs that the two drugs have the synergistic effect or partial synergistic effect, wherein 35% with FIC≤0.5 have the synergistic effect. For the 20 MDRABs, when the *Pithecellobium clypearia* Benth water extract is smaller than or equal to the single-use MIC, the $MIC_{50}$ of the TE is reduced from single-use 256 μg/ml to 64 μg/ml and is reduced by 75%; and the $MIC_{90}$ is reduced from 512 μg/ml to 128 μg/ml and is reduced by 75%.

For the 20 MDRABs, it is indicated by FIC≤2 with the combined use of the *Pithecellobium clypearia* Benth water extract and the POLB that the two drugs have no antagonistic effect, wherein 25% with FIC≤0.5 have the synergistic effect. For the 20 MDRABs, when the *Pithecellobium clypearia* Benth water extract is smaller than or equal to the single-use MIC, the $MIC_{50}$ of the POLB is reduced from single-use 4 μg/ml to 1 μg/ml and is reduced by 75%; and the $MIC_{90}$ is reduced from 16 μg/ml to 4 μg/ml and is reduced by 75%.

It is indicated by FIC≤2 with the combined use of the *Pithecellobium clypearia* Benth water extract and the CAZ to the 20 MDRABs that the two drugs have no antagonistic effect, wherein 20% with FIC≤0.5 have the synergistic effect. When the *Pithecellobium clypearia* Benth water extract is smaller than or equal to the single-use MIC, the $MIC_{50}$ of the CAZ is reduced from single-use 512 μg/ml to 128 μg/ml and is reduced by 75%; and the $MIC_{90}$ is reduced from 512 μg/ml to 256 μg/ml and is reduced by 50%.

It is indicated by FIC≤2 with the combined use of the *Pithecellobium clypearia* Benth water extract and the LVX to the 20 MDRABs that the two drugs have no antagonistic effect, wherein 35% with FIC≤0.5 show that the two drugs have a certain synergistic effect. For the 20 MDRAB, when the *Pithecellobium clypearia* Benth water extract is smaller than or equal to the single-use MIC, the $MIC_{50}$ of the LVX is reduced from single-use 8 μg/ml to 2 μg/ml and is reduced by 75%; and the $MIC_{90}$ is reduced from 32 μg/ml to 8 μg/ml and is reduced by 75%.

2.2. In-vitro inhibitory test results of the *Pithecellobium clypearia* Benth 10% ethanol extract and the five antibiotics (the IMP, the TE, the POLB, the CAZ and the LVX) to the MDRABs are shown in table A13.

In-vitro bactericidal test results of the *Pithecellobium clypearia* Benth 10% ethanol extract to the MDRABs are shown in table A14.

The statistic analysis on in-vitro inhibitory and bactericidal $MIC_{50}$ and $MIC_{90}$ of the *Pithecellobium clypearia* Benth 10% ethanol extract and the five antibiotics to the MDRABs is shown in table A15.

The statistic analysis on $MBC_{50}$ and $MBC_{90}$ of the EA to the MDRABs is shown in table A16.

FIC values of a combined drug sensitive test of the *Pithecellobium clypearia* Benth 10% ethanol extract and the five antibiotics and distribution statistical results of the FIC values are shown in table A17 and table A18.

The sensibilization effects of the *Pithecellobium clypearia* Benth 10% ethanol extract to the five antibiotics and the $MIC_{50}$ and $MIC_{90}$ after combined use are shown in tables A19-A24.

TABLE A13

In-vitro inhibitory test results of the *Pithecellobium clypearia*
Benth 10% ethanol extract and the five antibiotics to the MDRABs

| Strain No. | MIC (μg/ml) | | | | | |
|---|---|---|---|---|---|---|
| | EA | IMP | TE | LVX | CAZ | POLB |
| A1 | 600 | 1 | 2 | 0.5 | 128 | 8 |
| A2 | 600 | 32 | 256 | 16 | 512 | 2 |
| A3 | 600 | 32 | 256 | 4 | 512 | 2 |
| A4 | 600 | 8 | 8 | 0.5 | 256 | 2 |
| A5 | 600 | 32 | 32 | 4 | 64 | 4 |
| A6 | 600 | 32 | 256 | 8 | >512 | 8 |
| A7 | 600 | 32 | 512 | 8 | >512 | 4 |
| A8 | 600 | 32 | 256 | 4 | 512 | 8 |
| A9 | 600 | 32 | 256 | 4 | 512 | 1 |
| A10 | 600 | 16 | 128 | 32 | 512 | 32 |
| A11 | 600 | 32 | 256 | 4 | 512 | 16 |
| A12 | 600 | 32 | 512 | 32 | 512 | 2 |
| A13 | 600 | 32 | 512 | 32 | 256 | 2 |
| A14 | 600 | 32 | 256 | 16 | 512 | 0.5 |
| A15 | 600 | 32 | >512 | 32 | 256 | 2 |
| A16 | 600 | 32 | 512 | 8 | 512 | 4 |
| A17 | 600 | 16 | 512 | 16 | 256 | 64 |
| A18 | 600 | 32 | 512 | 8 | 512 | 4 |
| A19 | 600 | 32 | 512 | 16 | 256 | 4 |
| A20 | 600 | 32 | 256 | 16 | 512 | 2 |
| ATCC27853 | 300 | 1 | 8 | 1 | 4 | 1 |

TABLE A14

In-vitro bactericidal test results of the *Pithecellobium clypearia* Benth 10% ethanol extract to the MDRABs

| Strain No. | MBC (µg/ml) |
|---|---|
| A1 | 1200 |
| A2 | 1200 |
| A3 | 1200 |
| A4 | 1200 |
| A5 | 1200 |
| A6 | 1200 |
| A7 | 1200 |
| A8 | 1200 |
| A9 | 1200 |
| A10 | 1200 |
| A11 | 1200 |
| A12 | 1200 |
| A13 | 1200 |
| A14 | 1200 |
| A15 | 1200 |
| A16 | 1200 |
| A17 | 1200 |
| A18 | 1200 |
| A19 | 1200 |
| A20 | 1200 |

TABLE A15

Statistical results on in-vitro inhibitory $MIC_{50}$ and $MIC_{90}$ of the *Pithecellobium clypearia* Benth 10% ethanol extract and the antibiotics to the MDRABs

| | MIC (µg/ml) | | |
|---|---|---|---|
| Drug | Range | $MIC_{50}$ | $MIC_{90}$ |
| EA | 600 | 600 | 600 |
| IMP | 1-32 | 32 | 32 |
| TE | 2-512 | 256 | 512 |
| POLB | 0.5-64 | 4 | 16 |
| CAZ | 64-512 | 512 | 512 |
| LVX | 0.5-32 | 8 | 32 |

TABLE A16 bactericidal $MBC_{50}$ and $MBC_{90}$ of the *Pithecellobium clypearia* Benth 10% ethanol extract to the MDRABs

| | MBC (µg/ml) | | |
|---|---|---|---|
| Drug | Range | $MBC_{50}$ | $MBC_{90}$ |
| EA | 1200 | 1200 | 1200 |

TABLE A17

FIC values of the combined drug sensitive test of the *Pithecellobium clypearia* Benth 10% ethanol extract and the five antibiotics

| Strain No. | FIC | | | | |
|---|---|---|---|---|---|
| | EA + IMP | EA + TE | EA + POLB | EA + CAZ | EA + LVX |
| A1 | 1 | 1 | 1 | 1 | 0.625 |
| A2 | 0.75 | 0.75 | 1 | 1 | 1 |
| A3 | 0.75 | 0.75 | 1 | 1 | 0.625 |
| A4 | 1.5 | 0.5 | 1 | 0.5 | 0.625 |
| A5 | 0.5 | 0.375 | 0.75 | 1 | 1 |
| A6 | 0.625 | 0.75 | 0.375 | 1 | 1 |
| A7 | 0.5 | 0.5 | 0.375 | 1 | 1 |
| A8 | 1 | 0.5 | 0.507813 | 0.75 | 1 |
| A9 | 0.375 | 0.375 | 0.5625 | 0.75 | 0.265625 |
| A10 | 0.75 | 0.75 | 0.375 | 1 | 0.75 |
| A11 | 0.5 | 0.5 | 1 | 0.75 | 1 |
| A12 | 0.5 | 0.5 | 1 | 0.75 | 0.75 |
| A13 | 0.5 | 1 | 1 | 1 | 0.75 |
| A14 | 1 | 1 | 0.625 | 0.375 | 1 |
| A15 | 0.75 | 0.625 | 1 | 1 | 1 |
| A16 | 0.5 | 1 | 0.75 | 0.5 | 0.75 |
| A17 | 0.75 | 0.375 | 0.75 | 0.5 | 0.5 |
| A18 | 1 | 0.5 | 0.75 | 1 | 1 |
| A19 | 0.5 | 1 | 0.75 | 0.5 | 0.375 |
| A20 | 0.5 | 1.5 | 1 | 0.5 | 0.5 |

TABLE A18

Distribution statistics of the FIC values of the combined drug sensitive test of the *Pithecellobium clypearia* Benth 10% ethanol extract and the five antibiotics

| FIC Range | EA + IMP | EA + TE | EA + POLB | EA + CAZ | EA + LVX |
|---|---|---|---|---|---|
| FIC ≤ 0.5 | 45% | 45% | 15% | 30% | 20% |
| 0.5 < FIC ≤ 1 | 50% | 50% | 85% | 70% | 80% |
| 1 < FIC ≤ 2 | 5% | 5% | — | — | — |
| FIC > 2 | — | — | — | — | — |

TABLE A19

Sensibilization effect of the *Pithecellobium clypearia* Benth 10% ethanol extract to the IMP and MIC after combined use

| Strain No. | EA single-use MIC (µg/ml) | EA combined-use MIC (µg/ml) | IMP single-use MIC (µg/ml) | IMP combined-use MIC (µg/ml) |
|---|---|---|---|---|
| A1 | 600 | 300 | 1 | 0.5 |
| A2 | 600 | 300 | 32 | 8 |
| A3 | 600 | 300 | 32 | 8 |
| A4 | 600 | 300 | 8 | 8 |
| A5 | 600 | 150 | 32 | 8 |
| A6 | 600 | 300 | 32 | 4 |
| A7 | 600 | 150 | 32 | 8 |
| A8 | 600 | 300 | 32 | 16 |
| A9 | 600 | 75 | 32 | 8 |
| A10 | 600 | 150 | 16 | 8 |
| A11 | 600 | 150 | 32 | 8 |
| A12 | 600 | 150 | 32 | 8 |
| A13 | 600 | 150 | 32 | 8 |
| A14 | 600 | 300 | 32 | 16 |
| A15 | 600 | 300 | 32 | 8 |
| A16 | 600 | 150 | 32 | 8 |
| A17 | 600 | 300 | 16 | 4 |
| A18 | 600 | 300 | 32 | 16 |
| A19 | 600 | 150 | 32 | 8 |
| A20 | 600 | 150 | 32 | 8 |

TABLE A20

Sensibilization effect of the *Pithecellobium clypearia* Benth 10% ethanol extract to the TE and MIC after combined use

| Strain No. | EA single-use MIC (µg/ml) | EA combined-use MIC (µg/ml) | TE single-use MIC (µg/ml) | TE combined-use MIC (µg/ml) |
|---|---|---|---|---|
| A1 | 600 | 300 | 2 | 1 |
| A2 | 600 | 300 | 256 | 64 |

TABLE A20-continued

Sensibilization effect of the *Pithecellobium clypearia* Benth 10% ethanol extract to the TE and MIC after combined use

| Strain No. | EA single-use MIC (μg/ml) | EA combined-use MIC (μg/ml) | TE single-use MIC (μg/ml) | TE combined-use MIC (μg/ml) |
|---|---|---|---|---|
| A3 | 600 | 300 | 256 | 64 |
| A4 | 600 | 150 | 8 | 2 |
| A5 | 600 | 150 | 32 | 4 |
| A6 | 600 | 300 | 256 | 64 |
| A7 | 600 | 150 | 512 | 128 |
| A8 | 600 | 150 | 256 | 64 |
| A9 | 600 | 150 | 256 | 32 |
| A10 | 600 | 300 | 128 | 32 |
| A11 | 600 | 150 | 256 | 64 |
| A12 | 600 | 150 | 512 | 128 |
| A13 | 600 | 300 | 512 | 256 |
| A14 | 600 | 300 | 256 | 128 |
| A15 | 600 | 300 | 1024 | 128 |
| A16 | 600 | 300 | 512 | 256 |
| A17 | 600 | 150 | 512 | 64 |
| A18 | 600 | 150 | 512 | 128 |
| A19 | 600 | 300 | 512 | 256 |
| A20 | 600 | 300 | 256 | 256 |

TABLE A21

Sensibilization effect of the *Pithecellobium clypearia* Benth 10% ethanol extract to the POLB and MIC after combined use

| Strain No. | EA single-use MIC (μg/ml) | EA combined-use MIC (μg/ml) | POLB single-use MIC (μg/ml) | POLB combined-use MIC (μg/ml) |
|---|---|---|---|---|
| A1 | 600 | 300 | 8 | 4 |
| A2 | 600 | 300 | 2 | 1 |
| A3 | 600 | 300 | 2 | 1 |
| A4 | 600 | 300 | 2 | 1 |
| A5 | 600 | 300 | 4 | 1 |
| A6 | 600 | 150 | 8 | 1 |
| A7 | 600 | 75 | 4 | 1 |
| A8 | 600 | 300 | 8 | 0.0625 |
| A9 | 600 | 300 | 1 | 0.0625 |
| A10 | 600 | 150 | 32 | 4 |
| A11 | 600 | 300 | 16 | 8 |
| A12 | 600 | 300 | 2 | 1 |
| A13 | 600 | 300 | 2 | 1 |
| A14 | 600 | 300 | 0.5 | 0.0625 |
| A15 | 600 | 300 | 2 | 1 |
| A16 | 600 | 300 | 4 | 1 |
| A17 | 600 | 300 | 64 | 16 |
| A18 | 600 | 300 | 4 | 1 |
| A19 | 600 | 300 | 4 | 1 |
| A20 | 600 | 300 | 2 | 1 |

TABLE A22

Sensibilization effect of the *Pithecellobium clypearia* Benth 10% ethanol extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| A1 | 600 | 300 | 128 | 64 |
| A2 | 600 | 300 | 512 | 256 |
| A3 | 600 | 300 | 512 | 256 |
| A4 | 600 | 150 | 256 | 64 |
| A5 | 600 | 300 | 64 | 32 |
| A6 | 600 | 300 | 1024 | 512 |
| A7 | 600 | 300 | 1024 | 512 |
| A8 | 600 | 150 | 512 | 256 |
| A9 | 600 | 300 | 512 | 128 |
| A10 | 600 | 300 | 512 | 256 |
| A11 | 600 | 300 | 512 | 128 |
| A12 | 600 | 300 | 512 | 128 |
| A13 | 600 | 300 | 256 | 128 |
| A14 | 600 | 150 | 512 | 64 |
| A15 | 600 | 300 | 256 | 128 |
| A16 | 600 | 150 | 512 | 128 |
| A17 | 600 | 150 | 256 | 64 |
| A18 | 600 | 300 | 512 | 256 |
| A19 | 600 | 150 | 256 | 64 |
| A20 | 600 | 150 | 512 | 128 |

TABLE A23

Sensibilization effect of the *Pithecellobium clypearia* Benth 10% ethanol extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| A1 | 600 | 300 | 0.5 | 0.0625 |
| A2 | 600 | 300 | 16 | 8 |
| A3 | 600 | 300 | 16 | 2 |
| A4 | 600 | 300 | 0.5 | 0.0625 |
| A5 | 600 | 300 | 4 | 2 |
| A6 | 600 | 300 | 8 | 4 |
| A7 | 600 | 300 | 8 | 4 |
| A8 | 600 | 300 | 4 | 2 |
| A9 | 600 | 150 | 4 | 0.0625 |
| A10 | 600 | 300 | 32 | 8 |
| A11 | 600 | 300 | 4 | 2 |
| A12 | 600 | 300 | 32 | 8 |
| A13 | 600 | 300 | 32 | 8 |
| A14 | 600 | 300 | 16 | 8 |
| A15 | 600 | 300 | 32 | 16 |
| A16 | 600 | 150 | 8 | 4 |
| A17 | 600 | 150 | 16 | 4 |
| A18 | 600 | 300 | 8 | 4 |
| A19 | 600 | 150 | 16 | 2 |
| A20 | 600 | 150 | 16 | 4 |

TABLE A24

$MIC_{50}$ and $MIC_{90}$ of the five antibiotics after combined use

| Combined drug | Antibiotic (μg/ml) $MIC_{50}$ after combined use | $MIC_{90}$ after combined use |
|---|---|---|
| EA + IMP | 8 | 16 |
| EA + TE | 64 | 256 |
| EA + POLB | 1 | 4 |
| EA + CAZ | 128 | 256 |
| EA + LVX | 4 | 8 |

With the single use of the *Pithecellobium clypearia* Benth 10% ethanol extract to the MDRABs, the $MIC_{50}$ is 600 μg/ml, the $MIC_{90}$ is 600 μg/ml, the $MBC_{50}$ is 1200 μg/ml, and the $MBC_{90}$ is 1200 μg/ml.

It is indicated by FIC≤1 with the combined use of the *Pithecellobium clypearia* Benth 10% ethanol extract and the IMP that the two drugs have the synergistic effect or partial synergistic effect, wherein 45% with FIC≤0.5 have the synergistic effect. For the 20 MDRABs, when the concentration of the *Pithecellobium clypearia* Benth 10% ethanol extract is smaller than or equal to ½ of the single-use MIC, the $MIC_{50}$ of the IMP is reduced from single-use 32 μg/ml to 8 μg/ml and is reduced by 75%; and the $MIC_{90}$ is reduced from 32 μg/ml to 16 μg/ml and is reduced by 50%.

It is indicated by FIC≤1 with the combined use of the *Pithecellobium clypearia* Benth 10% ethanol extract and the TE to the 20 MDRABs that the two drugs have the synergistic effect or partial synergistic effect, wherein 45% with FIC≤0.5 have the synergistic effect. For the 20 MDRABs, when the *Pithecellobium clypearia* Benth 10% ethanol extract is smaller than or equal to ½ of the single-use MIC, the $MIC_{50}$ of the TE is reduced from single-use 256 μg/ml to 64 μg/ml and is reduced by 75%; and the $MIC_{90}$ is reduced from 512 μg/ml to 256 μg/ml and is reduced by 50%.

For the 20 MDRABs, it is indicated by FIC≤2 with the combined use of the *Pithecellobium clypearia* Benth 10% ethanol extract and the POLB that the two drugs have no antagonistic effect, wherein 15% with FIC≤0.5 have the synergistic effect. For the 20 MDRABs, when the *Pithecellobium clypearia* Benth 10% ethanol extract is smaller than or equal to the single-use MIC, the $MIC_{50}$ of the POLB is reduced from single-use 4 μg/ml to 1 μg/ml and is reduced by 75%; and the $MIC_{90}$ is reduced from 16 μg/ml to 4 μg/ml and is reduced by 75%.

It is indicated by FIC≤2 with the combined use of the *Pithecellobium clypearia* Benth 10% ethanol extract and the CAZ to the 20 MDRABs that the two drugs have no antagonistic effect, wherein 30% with FIC≤0.5 have the synergistic effect. When an ethyl acetate extract of the *Pithecellobium clypearia* Benth 10% ethanol extract is smaller than or equal to ½ of the single-use MIC, the $MIC_{50}$ of the CAZ is reduced from single-use 512 μg/ml to 128 μg/ml and is reduced by 75%; and the $MIC_{90}$ is reduced from 512 μg/ml to 256 μg/ml and is reduced by 50%.

It is indicated by FIC≤2 with the combined use of the *Pithecellobium clypearia* Benth 10% ethanol extract and the LVX to the 20 MDRABs that the two drugs have no antagonistic effect, wherein 25% with FIC≤0.5 show that the two drugs have a certain synergistic effect. For the 20 MDRABs, when the *Pithecellobium clypearia* Benth 10% ethanol extract is smaller than or equal to the single-use MIC, the $MIC_{50}$ of the LVX is reduced from single-use 8 μg/ml to 4 μg/ml and is reduced by 50%; and the $MIC_{90}$ is reduced from 32 μg/ml to 8 μg/ml and is reduced by 75%.

2.3. In-vitro inhibitory test results of the *Pithecellobium clypearia* Benth 60% ethanol extract and the five antibiotics (the IMP, the TE, the POLB, the CAZ and the LVX) to the MDRABs are shown in table A25.

In-vitro bactericidal test results of the *Pithecellobium clypearia* Benth 60% ethanol extract to the MDRABs are shown in table A26.

The statistic analysis on in-vitro inhibitory and bactericidal $MIC_{50}$ and $MIC_{90}$ of the *Pithecellobium clypearia* Benth 60% ethanol extract and the five antibiotics to the MDRABs is shown in table A27.

The statistic analysis on $MBC_{50}$ and $MBC_{90}$ of the EA to the MDRABs is shown in table A28.

FIC values of a combined drug sensitive test of the *Pithecellobium clypearia* Benth 60% ethanol extract and the five antibiotics and distribution statistical results of the FIC values are shown in table A29 and table A30.

The sensibilization effects of the *Pithecellobium clypearia* Benth 60% ethanol extract to the five antibiotics and the $MIC_{50}$ and $MIC_{90}$ after combined use are shown in tables A31-A36.

TABLE A25

In-vitro inhibitory test results of the *Pithecellobium clypearia* Benth 60% ethanol extract and the five antibiotics to the MDRABs

| Strain No. | MIC (μg/ml) | | | | | |
|---|---|---|---|---|---|---|
| | EA | IMP | TE | LVX | CAZ | POLB |
| A1 | 300 | 1 | 2 | 0.5 | 128 | 8 |
| A2 | 300 | 32 | 256 | 16 | 512 | 2 |
| A3 | 600 | 32 | 256 | 4 | 512 | 2 |
| A4 | 600 | 8 | 8 | 0.5 | 256 | 2 |
| A5 | 300 | 32 | 32 | 4 | 64 | 4 |
| A6 | 300 | 32 | 256 | 8 | >512 | 8 |
| A7 | 300 | 32 | 512 | 8 | >512 | 4 |
| A8 | 300 | 32 | 256 | 4 | 512 | 8 |
| A9 | 600 | 32 | 256 | 4 | 512 | 1 |
| A10 | 300 | 16 | 128 | 32 | 512 | 32 |
| A11 | 600 | 32 | 256 | 4 | 512 | 16 |
| A12 | 300 | 32 | 512 | 32 | 512 | 2 |
| A13 | 300 | 32 | 512 | 32 | 256 | 2 |
| A14 | 600 | 32 | 256 | 16 | 512 | 0.5 |
| A15 | 600 | 32 | >512 | 32 | 256 | 2 |
| A16 | 300 | 32 | 512 | 8 | 512 | 4 |
| A17 | 300 | 16 | 512 | 16 | 256 | 64 |
| A18 | 300 | 32 | 512 | 8 | 512 | 4 |
| A19 | 300 | 32 | 512 | 16 | 256 | 4 |
| A20 | 300 | 32 | 256 | 16 | 512 | 2 |
| ATCC27853 | 300 | 1 | 8 | 1 | 4 | 1 |

TABLE A26

In-vitro bactericidal test results of the *Pithecellobium clypearia* Benth 60% ethanol extract to the MDRABs

| Strain No. | MBC (μg/ml) |
|---|---|
| A1 | 600 |
| A2 | 600 |
| A3 | 1200 |
| A4 | 1200 |
| A5 | 600 |
| A6 | 600 |
| A7 | 600 |
| A8 | 1200 |
| A9 | 600 |
| A10 | 600 |
| A11 | 600 |
| A12 | 600 |
| A13 | 600 |
| A14 | 1200 |
| A15 | 1200 |
| A16 | 1200 |
| A17 | 600 |
| A18 | 600 |
| A19 | 600 |
| A20 | 600 |

TABLE A27

Statistics on in-vitro inhibitory $MIC_{50}$ and $MIC_{90}$ of the *Pithecellobium clypearia* Benth 60% ethanol extract and the antibiotics to the MDRABs

| Drug | MIC (μg/ml) | | |
|---|---|---|---|
| | Range | $MIC_{50}$ | $MIC_{90}$ |
| EA | 300-600 | 300 | 600 |
| IMP | 1-32 | 32 | 32 |
| TE | 2-512 | 256 | 512 |
| POLB | 0.5-64 | 4 | 16 |
| CAZ | 64-512 | 512 | 512 |
| LVX | 0.5-32 | 8 | 32 |

TABLE A28

Bactericidal MBC$_{50}$ and MIC$_{90}$ of the *Pithecellobium clypearia* Benth 60% ethanol extract to the MDRABs

|  | MBC (μg/ml) | | |
| --- | --- | --- | --- |
| Drug | Range | MBC$_{50}$ | MBC$_{90}$ |
| EA | 600-1200 | 600 | 1200 |

TABLE A29

FIC values of the combined drug sensitive test of the *Pithecellobium clypearia* Benth 60% ethanol extract and the five antibiotics

| Strain No. | FIC | | | | |
| --- | --- | --- | --- | --- | --- |
|  | EA + IMP | EA + TE | EA + POLB | EA + CAZ | EA + LVX |
| A1 | 0.75 | 0.75 | 1.5 | 0.75 | 0.375 |
| A2 | 0.5 | 0.5 | 1.25 | 0.75 | 1.25 |
| A3 | 0.375 | 0.375 | 1 | 0.5 | 1.0040 |
| A4 | 0.1875 | 0.625 | 0.75 | 0.5 | 0.625 |
| A5 | 0.5 | 0.75 | 1 | 0.75 | 1.25 |
| A6 | 0.625 | 0.75 | 0.5 | 1 | 1 |
| A7 | 0.625 | 0.75 | 0.75 | 0.75 | 1 |
| A8 | 0.625 | 0.625 | 1.0080 | 0.75 | 1.25 |
| A9 | 0.375 | 0.375 | 0.5625 | 0.625 | 0.5156 |
| A10 | 0.75 | 0.75 | 0.5 | 0.75 | 1.0020 |
| A11 | 0.375 | 0.375 | 0.5 | 0.625 | 1.125 |
| A12 | 0.3125 | 0.5 | 1.25 | 0.75 | 1.03125 |
| A13 | 0.5 | 0.5 | 1.5 | 1 | 1.0020 |
| A14 | 0.25 | 0.375 | 0.625 | 0.625 | 0.625 |
| A15 | 0.375 | 0.3125 | 0.53125 | 0.75 | 0.5020 |
| A16 | 0.5 | 0.5 | 1.0156 | 0.75 | 0.75 |
| A17 | 0.625 | 1 | 1.03125 | 0.75 | 0.75 |
| A18 | 0.5 | 0.625 | 1.125 | 0.75 | 0.75 |
| A19 | 0.375 | 0.5 | 1.125 | 1 | 1 |
| A20 | 0.5 | 0.625 | 1.25 | 1 | 1 |

TABLE A30

Distribution statistics of the FIC values of the combined drug sensitive test of the *Pithecellobium clypearia* Benth 60% ethanol extract and the five antibiotics

| FIC Range | EA + IMP | EA + TE | EA + POLB | EA + CAZ | EA + LVX |
| --- | --- | --- | --- | --- | --- |
| FIC ≤ 0.5 | 70% | 50% | 15% | 10% | 5% |
| 0.5 < FIC ≤ 1 | 30% | 50% | 35% | 85% | 55% |
| 1 < FIC ≤ 2 | — | — | 50% | 5% | 40% |
| FIC > 2 | — | — | — | — | — |

TABLE A31

Sensibilization effect of the *Pithecellobium clypearia* Benth 60% ethanol extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
| --- | --- | --- | --- | --- |
| A1 | 300 | 75 | 1 | 0.5 |
| A2 | 300 | 75 | 32 | 8 |
| A3 | 600 | 75 | 32 | 8 |
| A4 | 600 | 75 | 8 | 0.5 |
| A5 | 300 | 75 | 32 | 8 |
| A6 | 300 | 37.5 | 32 | 16 |
| A7 | 300 | 37.5 | 32 | 16 |
| A8 | 300 | 37.5 | 32 | 16 |
| A9 | 600 | 150 | 32 | 4 |
| A10 | 300 | 75 | 16 | 8 |
| A11 | 600 | 150 | 32 | 4 |
| A12 | 300 | 18.75 | 32 | 8 |
| A13 | 300 | 75 | 32 | 8 |
| A14 | 600 | 75 | 32 | 4 |
| A15 | 600 | 150 | 32 | 4 |
| A16 | 300 | 75 | 32 | 8 |
| A17 | 300 | 150 | 16 | 2 |
| A18 | 300 | 75 | 32 | 8 |
| A19 | 300 | 37.5 | 32 | 8 |
| A20 | 300 | 75 | 32 | 8 |

TABLE A32

Sensibilization effect of the *Pithecellobium clypearia* Benth 60% ethanol extract to the TE and MIC after combined use

| Strain No. | EA single-use MIC (μg/ml) | EA combined-use MIC (μg/ml) | TE single-use MIC (μg/ml) | TE combined-use MIC (μg/ml) |
| --- | --- | --- | --- | --- |
| A1 | 300 | 75 | 2 | 1 |
| A2 | 300 | 75 | 256 | 64 |
| A3 | 600 | 150 | 256 | 32 |
| A4 | 600 | 300 | 8 | 1 |
| A5 | 300 | 150 | 32 | 8 |
| A6 | 300 | 75 | 256 | 128 |
| A7 | 300 | 150 | 512 | 128 |
| A8 | 300 | 150 | 256 | 32 |
| A9 | 600 | 150 | 256 | 32 |
| A10 | 300 | 150 | 128 | 32 |
| A11 | 600 | 150 | 256 | 32 |
| A12 | 300 | 75 | 512 | 128 |
| A13 | 300 | 75 | 512 | 128 |
| A14 | 600 | 150 | 256 | 32 |
| A15 | 600 | 150 | 1024 | 64 |
| A16 | 300 | 75 | 512 | 128 |
| A17 | 300 | 150 | 512 | 256 |
| A18 | 300 | 150 | 512 | 64 |
| A19 | 300 | 75 | 512 | 128 |
| A20 | 300 | 150 | 256 | 32 |

TABLE A33

Sensibilization effect of the *Pithecellobium clypearia* Benth 60% ethanol extract to the POLB and MIC after combined use

| Strain No. | EA single-use MIC (μg/ml) | EA combined-use MIC (μg/ml) | POLB single-use MIC (μg/ml) | POLB combined-use MIC (μg/ml) |
| --- | --- | --- | --- | --- |
| A1 | 300 | 300 | 8 | 4 |
| A2 | 300 | 300 | 2 | 0.5 |
| A3 | 600 | 300 | 2 | 1 |
| A4 | 600 | 150 | 2 | 1 |
| A5 | 300 | 150 | 4 | 2 |
| A6 | 300 | 75 | 8 | 2 |
| A7 | 300 | 75 | 4 | 2 |
| A8 | 300 | 300 | 8 | 0.0625 |
| A9 | 600 | 300 | 1 | 0.0625 |
| A10 | 300 | 75 | 32 | 8 |
| A11 | 600 | 150 | 16 | 4 |
| A12 | 300 | 300 | 2 | 0.5 |
| A13 | 300 | 300 | 2 | 1 |
| A14 | 600 | 300 | 0.5 | 0.0625 |
| A15 | 600 | 300 | 2 | 0.0625 |
| A16 | 300 | 300 | 4 | 0.0625 |
| A17 | 300 | 300 | 64 | 2 |
| A18 | 300 | 300 | 4 | 0.5 |

TABLE A33-continued

Sensibilization effect of the *Pithecellobium clypearia* Benth 60% ethanol extract to the POLB and MIC after combined use

| Strain No. | EA single-use MIC (μg/ml) | EA combined-use MIC (μg/ml) | POLB single-use MIC (μg/ml) | POLB combined-use MIC (μg/ml) |
|---|---|---|---|---|
| A19 | 300 | 300 | 4 | 0.5 |
| A20 | 300 | 300 | 2 | 0.5 |

TABLE A34

Sensibilization effect of the *Pithecellobium clypearia* Benth 60% ethanol extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| A1 | 300 | 75 | 128 | 64 |
| A2 | 300 | 150 | 512 | 128 |
| A3 | 600 | 150 | 512 | 128 |
| A4 | 600 | 150 | 256 | 64 |
| A5 | 300 | 75 | 64 | 32 |
| A6 | 300 | 150 | 1024 | 512 |
| A7 | 300 | 150 | 1024 | 256 |
| A8 | 300 | 75 | 512 | 256 |
| A9 | 600 | 300 | 512 | 64 |
| A10 | 300 | 150 | 512 | 128 |
| A11 | 600 | 300 | 512 | 64 |
| A12 | 300 | 150 | 512 | 128 |
| A13 | 300 | 150 | 256 | 128 |
| A14 | 600 | 75 | 512 | 256 |
| A15 | 600 | 150 | 256 | 128 |
| A16 | 300 | 150 | 512 | 128 |
| A17 | 300 | 75 | 256 | 128 |
| A18 | 300 | 150 | 512 | 128 |
| A19 | 300 | 150 | 256 | 128 |
| A20 | 300 | 150 | 512 | 256 |

TABLE A35

Sensibilization effect of the *Pithecellobium clypearia* Benth 60% ethanol extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| A1 | 300 | 75 | 0.5 | 0.0625 |
| A2 | 300 | 75 | 16 | 16 |
| A3 | 300 | 300 | 16 | 0.0625 |
| A4 | 600 | 300 | 0.5 | 0.0625 |
| A5 | 300 | 75 | 4 | 4 |
| A6 | 300 | 150 | 8 | 4 |
| A7 | 300 | 150 | 8 | 4 |
| A8 | 300 | 75 | 4 | 4 |
| A9 | 600 | 300 | 4 | 0.0625 |
| A10 | 300 | 300 | 32 | 0.0625 |
| A11 | 600 | 75 | 4 | 4 |
| A12 | 300 | 300 | 32 | 1 |
| A13 | 300 | 300 | 32 | 0.0625 |
| A14 | 600 | 75 | 16 | 8 |
| A15 | 600 | 300 | 32 | 0.0625 |
| A16 | 300 | 75 | 8 | 4 |
| A17 | 300 | 150 | 16 | 4 |
| A18 | 300 | 75 | 8 | 4 |
| A19 | 300 | 150 | 16 | 8 |
| A20 | 300 | 150 | 16 | 8 |

TABLE A36

$MIC_{50}$ and $MIC_{90}$ of the five antibiotics after combined use

| Combined drug | $MIC_{50}$ after combined use | $MIC_{90}$ after combined use |
|---|---|---|
| EA + IMP | 8 | 16 |
| EA + TE | 32 | 128 |
| EA + POLB | 0.5 | 4 |
| EA + CAZ | 128 | 256 |
| EA + LVX | 4 | 8 |

With the single use of the *Pithecellobium clypearia* Benth 60% ethanol extract to the MDRABs, the $MIC_{50}$ is 300 μg/ml, the $MIC_{90}$ is 600 μg/ml, the $MBC_{50}$ is 600 μg/ml, and the $MBC_{90}$ is 1200 μg/ml.

It is indicated by FIC≤1 with the combined use of the *Pithecellobium clypearia* Benth 60% ethanol extract and the IMP that the two drugs have the synergistic effect or partial synergistic effect, wherein 70% with FIC≤0.5 have the synergistic effect. For the 20 MDRABs, when the concentration of the *Pithecellobium clypearia* Benth 60% ethanol extract is smaller than or equal to ½ of the single-use MIC, the $MIC_{50}$ of the IMP is reduced from single-use 32 μg/ml to 8 μg/ml and is reduced by 75%; and the $MIC_{90}$ is reduced from 32 μg/ml to 16 μg/ml and is reduced by 50%.

It is indicated by FIC≤1 with the combined use of the *Pithecellobium clypearia* Benth 60% ethanol extract and the TE to the 20 MDRABs that the two drugs have the synergistic effect or partial synergistic effect, wherein 50% with FIC≤0.5 have the synergistic effect. For the 20 MDRABs, when the *Pithecellobium clypearia* Benth 60% ethanol extract is smaller than or equal to ½ of the single-use MIC, the $MIC_{50}$ of the TE is reduced from single-use 256 μg/ml to 32 μg/ml and is reduced by 87.5%; and the $MIC_{90}$ is reduced from 512 μg/ml to 128 μg/ml and is reduced by 75%.

For the 20 MDRABs, it is indicated by FIC≤2 with the combined use of the *Pithecellobium clypearia* Benth 60% ethanol extract and the POLB that the two drugs have no antagonistic effect, wherein 15% with FIC≤0.5 have the synergistic effect. For the 20 MDRABs, when the *Pithecellobium clypearia* Benth 60% ethanol extract is smaller than or equal to the single-use MIC, the $MIC_{50}$ of the POLB is reduced from single-use 4 μg/ml to 0.5 μg/ml and is reduced by 87.5%; and the $MIC_{90}$ is reduced from 16 μg/ml to 4 μg/ml and is reduced by 75%.

It is indicated by FIC≤2 with the combined use of the *Pithecellobium clypearia* Benth 60% ethanol extract and the CAZ to the 20 MDRABs that the two drugs have no antagonistic effect, wherein 10% with FIC≤0.5 have the synergistic effect. When the *Pithecellobium clypearia* Benth 60% ethanol extract is smaller than or equal to ½ of the single-use MIC, the $MIC_{50}$ of the CAZ is reduced from single-use 512 μg/ml to 128 μg/ml and is reduced by 75%; and the $MIC_{90}$ is reduced from 512 μg/ml to 256 μg/ml and is reduced by 50%.

It is indicated by FIC≤2 with the combined use of the *Pithecellobium clypearia* Benth 60% ethanol extract and the LVX to the 20 MDRABs that the two drugs have no antagonistic effect, wherein 5% with FIC≤0.5 show that the two drugs have a certain synergistic effect. For the 20 MDRABs, when the *Pithecellobium clypearia* Benth 60% ethanol extract is smaller than or equal to the single-use MIC, the $MIC_{50}$ of the LVX is reduced from single-use 8

µg/ml to 4 µg/ml and is reduced by 50%; and the $MIC_{90}$ is reduced from 32 µg/ml to 8 µg/ml and is reduced by 75%.

2.4. In-vitro inhibitory test results of the *Pithecellobium clypearia* Benth 95% ethanol extract and the five antibiotics (the IMP, the TE, the POLB, the CAZ and the LVX) to the MDRABs are shown in table A37.

In-vitro bactericidal test results of the *Pithecellobium clypearia* Benth 95% ethanol extract to the MDRABs are shown in table A38.

The statistic analysis on in-vitro inhibitory and bactericidal $MIC_{50}$ and $MIC_{90}$ of the *Pithecellobium clypearia* Benth 95% ethanol extract and the five antibiotics to the MDRABs is shown in table A39.

The statistic analysis on $MBC_{50}$ and $MBC_{90}$ of the EA to the MDRABs is shown in table A40.

FIC values of a combined drug sensitive test of the *Pithecellobium clypearia* Benth 95% ethanol extract and the five antibiotics and distribution statistical results of the FIC values are shown in table A41 and table A42.

The sensibilization effects of the *Pithecellobium clypearia* Benth 95% ethanol extract to the five antibiotics and the $MIC_{50}$ and $MIC_{90}$ after combined use are shown in tables A43-A48.

TABLE A37

In-vitro inhibitory test results of the *Pithecellobium clypearia* Benth 95% ethanol extract and the five antibiotics to the MDRABs

| Strain No. | MIC (µg/ml) | | | | | |
|---|---|---|---|---|---|---|
| | EA | IMP | TE | LVX | CAZ | POLB |
| A1 | 600 | 1 | 2 | 0.5 | 128 | 8 |
| A2 | 600 | 32 | 256 | 16 | 512 | 2 |
| A3 | 600 | 32 | 256 | 4 | 512 | 2 |
| A4 | 600 | 8 | 8 | 0.5 | 256 | 2 |
| A5 | 600 | 32 | 32 | 4 | 64 | 4 |
| A6 | 600 | 32 | 256 | 8 | >512 | 8 |
| A7 | 600 | 32 | 512 | 8 | >512 | 4 |
| A8 | 600 | 32 | 256 | 4 | 512 | 8 |
| A9 | 600 | 32 | 256 | 4 | 512 | 1 |
| A10 | 600 | 16 | 128 | 32 | 512 | 32 |
| A11 | 600 | 32 | 256 | 4 | 512 | 16 |
| A12 | 600 | 32 | 512 | 32 | 512 | 2 |
| A13 | 600 | 32 | 512 | 32 | 256 | 2 |
| A14 | 600 | 32 | 256 | 16 | 512 | 0.5 |
| A15 | 1200 | 32 | >512 | 32 | 256 | 2 |
| A16 | 600 | 32 | 512 | 8 | 512 | 4 |
| A17 | 600 | 16 | 512 | 16 | 256 | 64 |
| A18 | 600 | 32 | 512 | 8 | 512 | 4 |
| A19 | 600 | 32 | 512 | 16 | 256 | 4 |
| A20 | 600 | 32 | 256 | 16 | 512 | 2 |
| ATCC27853 | 300 | 1 | 8 | 1 | 4 | 1 |

TABLE A38

In-vitro bactericidal test results of the *Pithecellobium clypearia* Benth 95% ethanol extract to the MDRABs

| Strain No. | MBC (µg/ml) |
|---|---|
| A1 | 1200 |
| A2 | 1200 |
| A3 | 1200 |
| A4 | 1200 |
| A5 | 1200 |
| A6 | 1200 |
| A7 | 1200 |
| A8 | 1200 |
| A9 | 1200 |
| A10 | 1200 |
| A11 | 1200 |
| A12 | 1200 |
| A13 | 1200 |
| A14 | 1200 |
| A15 | 1200 |
| A16 | 1200 |
| A17 | 1200 |
| A18 | 1200 |
| A19 | 1200 |
| A20 | 1200 |

TABLE A39

Statistical results on in-vitro inhibitory $MIC_{50}$ and $MIC_{90}$ of the *Pithecellobium clypearia* Benth 95% ethanol extract and the antibiotics to the MDRABs

| Drug | MIC (µg/ml) | | |
|---|---|---|---|
| | Range | $MIC_{50}$ | $MIC_{90}$ |
| EA | 600-1200 | 600 | 600 |
| IMP | 1-32 | 32 | 32 |
| TE | 2-512 | 256 | 512 |
| POLB | 0.5-64 | 4 | 16 |
| CAZ | 64-512 | 512 | 512 |
| LVX | 0.5-32 | 8 | 32 |

TABLE A40

Bactericidal $MBC_{50}$ and $MBC_{90}$ of the *Pithecellobium clypearia* Benth 95% ethanol extract to the MDRABs

| Drug | MBC (µg/ml) | | |
|---|---|---|---|
| | Range | $MBC_{50}$ | $MBC_{90}$ |
| EA | 1200 | 1200 | 1200 |

TABLE A41

FIC values of the combined drug sensitive test of the *Pithecellobium clypearia* Benth 95% ethanol extract and the five antibiotics

| Strain No. | FIC | | | | |
|---|---|---|---|---|---|
| | EA + IMP | EA + TE | EA + POLB | EA + CAZ | EA + LVX |
| A1 | 0.75 | 0.75 | 1 | 1 | 1 |
| A2 | 0.5 | 0.5 | 0.75 | 0.75 | 1 |
| A3 | 0.5 | 0.375 | 1 | 0.75 | 0.625 |
| A4 | 0.3125 | 0.625 | 1 | 0.75 | 0.375 |
| A5 | 0.75 | 0.5 | 1 | 1 | 1 |
| A6 | 0.75 | 1 | 0.5 | 1 | 1 |
| A7 | 0.75 | 0.75 | 0.75 | 0.5 | 1 |
| A8 | 0.75 | 0.625 | 0.625 | 1 | 1 |
| A9 | 0.375 | 0.625 | 0.75 | 1 | 0.515625 |
| A10 | 0.75 | 0.75 | 0.5 | 1 | 0.3125 |
| A11 | 0.375 | 0.625 | 0.5 | 0.625 | 1.5 |
| A12 | 0.5 | 0.75 | 1 | 0.75 | 0.53125 |
| A13 | 0.75 | 0.5 | 1 | 0.75 | 0.5625 |
| A14 | 0.75 | 0.375 | 1 | 1 | 1 |
| A15 | 0.75 | 0.3125 | 0.28125 | 0.75 | 0.3125 |
| A16 | 0.5 | 0.75 | 0.515625 | 1 | 0.75 |
| A17 | 0.375 | 0.75 | 0.5625 | 1 | 0.5 |
| A18 | 0.5 | 0.75 | 0.75 | 0.5 | 1 |
| A19 | 0.5 | 0.75 | 0.75 | 0.75 | 1 |
| A20 | 0.5 | 0.625 | 0.75 | 1 | 0.75 |

TABLE A42

Distribution statistics of the FIC values of the combined drug sensitive test of the *Pithecellobium clypearia* Benth 95% ethanol extract and the five antibiotics

| FIC Range | EA + IMP | EA + TE | EA + POLB | EA + CAZ | EA + LVX |
|---|---|---|---|---|---|
| FIC ≤ 0.5 | 55% | 30% | 20% | 10% | 20% |
| 0.5 < FIC ≤ 1 | 45% | 70% | 80% | 90% | 75% |
| 1 < FIC ≤ 2 | — | — | — | — | 5% |
| FIC > 2 | — | — | — | — | — |

TABLE A43

Sensibilization effect of the *Pithecellobium clypearia* Benth 95% ethanol extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
|---|---|---|---|---|
| A1 | 600 | 150 | 1 | 0.5 |
| A2 | 600 | 150 | 32 | 8 |
| A3 | 600 | 150 | 32 | 8 |
| A4 | 600 | 150 | 8 | 0.5 |
| A5 | 600 | 300 | 32 | 8 |
| A6 | 600 | 150 | 32 | 16 |
| A7 | 600 | 150 | 32 | 16 |
| A8 | 600 | 150 | 32 | 16 |
| A9 | 600 | 150 | 32 | 4 |
| A10 | 600 | 150 | 16 | 8 |
| A11 | 600 | 150 | 32 | 4 |
| A12 | 600 | 150 | 32 | 8 |
| A13 | 600 | 300 | 32 | 8 |
| A14 | 600 | 300 | 32 | 8 |
| A15 | 1200 | 600 | 32 | 8 |
| A16 | 600 | 150 | 32 | 8 |
| A17 | 600 | 150 | 16 | 2 |
| A18 | 600 | 150 | 32 | 8 |
| A19 | 600 | 150 | 32 | 8 |
| A20 | 600 | 150 | 32 | 8 |

TABLE A44

Sensibilization effect of the *Pithecellobium clypearia* Benth 95% ethanol extract to the TE and MIC after combined use

| Strain No. | EA single-use MIC (μg/ml) | EA combined-use MIC (μg/ml) | TE single-use MIC (μg/ml) | TE combined-use MIC (μg/ml) |
|---|---|---|---|---|
| A1 | 600 | 150 | 2 | 1 |
| A2 | 600 | 150 | 256 | 64 |
| A3 | 600 | 150 | 256 | 32 |
| A4 | 600 | 300 | 8 | 1 |
| A5 | 600 | 150 | 32 | 8 |
| A6 | 600 | 300 | 256 | 128 |
| A7 | 600 | 300 | 512 | 128 |
| A8 | 600 | 300 | 256 | 32 |
| A9 | 600 | 300 | 256 | 32 |
| A10 | 600 | 300 | 128 | 32 |
| A11 | 600 | 300 | 256 | 32 |
| A12 | 600 | 300 | 512 | 128 |
| A13 | 600 | 150 | 512 | 128 |
| A14 | 600 | 150 | 256 | 32 |
| A15 | 1200 | 300 | 1024 | 64 |
| A16 | 600 | 300 | 512 | 128 |
| A17 | 600 | 300 | 512 | 128 |
| A18 | 600 | 300 | 512 | 128 |
| A19 | 600 | 300 | 512 | 128 |
| A20 | 600 | 300 | 256 | 32 |

TABLE A45

Sensibilization effect of the *Pithecellobium clypearia* Benth 95% ethanol extract to the POLB and MIC after combined use

| Strain No. | EA single-use MIC (μg/ml) | EA combined-use MIC (μg/ml) | POLB single-use MIC (μg/ml) | POLB combined-use MIC (μg/ml) |
|---|---|---|---|---|
| A1 | 600 | 300 | 8 | 4 |
| A2 | 600 | 300 | 2 | 0.5 |
| A3 | 600 | 300 | 2 | 1 |
| A4 | 600 | 300 | 2 | 1 |
| A5 | 600 | 300 | 4 | 2 |
| A6 | 600 | 150 | 8 | 2 |
| A7 | 600 | 150 | 4 | 2 |
| A8 | 600 | 300 | 8 | 1 |
| A9 | 600 | 300 | 1 | 0.25 |
| A10 | 600 | 150 | 32 | 8 |
| A11 | 600 | 150 | 16 | 4 |
| A12 | 600 | 300 | 2 | 1 |
| A13 | 600 | 300 | 2 | 1 |
| A14 | 600 | 300 | 0.5 | 0.25 |
| A15 | 1200 | 300 | 2 | 0.0625 |
| A16 | 600 | 300 | 4 | 0.0625 |
| A17 | 600 | 300 | 64 | 4 |
| A18 | 600 | 300 | 4 | 1 |
| A19 | 600 | 300 | 4 | 1 |
| A20 | 600 | 300 | 2 | 0.5 |

TABLE A46

Sensibilization effect of the *Pithecellobium clypearia* Benth 95% ethanol extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| A1 | 600 | 300 | 128 | 64 |
| A2 | 600 | 300 | 512 | 128 |
| A3 | 600 | 300 | 512 | 128 |
| A4 | 600 | 300 | 256 | 64 |
| A5 | 600 | 300 | 64 | 32 |
| A6 | 600 | 300 | 1024 | 512 |
| A7 | 600 | 150 | 1024 | 256 |
| A8 | 600 | 300 | 512 | 256 |
| A9 | 600 | 300 | 512 | 256 |
| A10 | 600 | 300 | 512 | 256 |
| A11 | 600 | 300 | 512 | 64 |
| A12 | 600 | 300 | 512 | 128 |
| A13 | 600 | 150 | 256 | 128 |
| A14 | 600 | 300 | 512 | 256 |
| A15 | 1200 | 300 | 256 | 128 |
| A16 | 600 | 300 | 512 | 256 |
| A17 | 600 | 300 | 256 | 128 |
| A18 | 600 | 150 | 512 | 128 |
| A19 | 600 | 150 | 256 | 128 |
| A20 | 600 | 300 | 512 | 256 |

TABLE A47

Sensibilization effect of the *Pithecellobium clypearia* Benth 95% ethanol extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| A1 | 600 | 300 | 0.5 | 0.25 |
| A2 | 600 | 300 | 16 | 8 |
| A3 | 600 | 300 | 16 | 2 |
| A4 | 600 | 150 | 0.5 | 0.0625 |
| A5 | 600 | 300 | 4 | 2 |
| A6 | 600 | 300 | 8 | 4 |
| A7 | 600 | 300 | 8 | 4 |
| A8 | 600 | 300 | 4 | 2 |

TABLE A47-continued

Sensibilization effect of the *Pithecellobium clypearia* Benth 95% ethanol extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| A9  | 600  | 300 | 4  | 0.0625 |
| A10 | 600  | 150 | 32 | 2 |
| A11 | 600  | 300 | 4  | 4 |
| A12 | 600  | 300 | 32 | 1 |
| A13 | 600  | 300 | 32 | 2 |
| A14 | 600  | 300 | 16 | 8 |
| A15 | 1200 | 300 | 32 | 2 |
| A16 | 600  | 150 | 8  | 4 |
| A17 | 600  | 150 | 16 | 4 |
| A18 | 600  | 300 | 8  | 4 |
| A19 | 600  | 300 | 16 | 8 |
| A20 | 600  | 150 | 16 | 8 |

TABLE A48

$MIC_{50}$ and $MIC_{90}$ of the five antibiotics after combined use

| Combined drug | Antibiotic (μg/ml) | |
|---|---|---|
|  | $MIC_{50}$ after combined use | $MIC_{90}$ after combined use |
| EA + IMP  | 8   | 16  |
| EA + TE   | 32  | 128 |
| EA + POLB | 1   | 4   |
| EA + CAZ  | 128 | 256 |
| EA + LVX  | 4   | 8   |

With the single use of the *Pithecellobium clypearia* Benth 95% ethanol extract to the MDRABs, the $MIC_{50}$ is 600 μg/ml, the $MIC_{90}$ is 600 μg/ml, the $MBC_{50}$ is 1200 μg/ml, and the $MBC_{90}$ is 1200 μg/ml.

It is indicated by FIC≤1 with the combined use of the *Pithecellobium clypearia* Benth 95% ethanol extract and the IMP that the two drugs have the synergistic effect or partial synergistic effect, wherein 55% with FIC≤0.5 have the synergistic effect. For the 20 MDRABs, when the concentration of the *Pithecellobium clypearia* Benth 95% ethanol extract is smaller than or equal to the single-use MIC, the $MIC_{50}$ of the IMP is reduced from single-use 32 μg/ml to 8 μg/ml and is reduced by 75%; and the $MIC_{90}$ is reduced from 32 μg/ml to 16 μg/ml and is reduced by 50%.

It is indicated by FIC≤1 with the combined use of the *Pithecellobium clypearia* Benth 95% ethanol extract and the TE to the 20 MDRABs that the two drugs have the synergistic effect or partial synergistic effect, wherein 35% with FIC≤0.5 have the synergistic effect. For the 20 MDRABs, when the *Pithecellobium clypearia* Benth 95% ethanol extract is smaller than or equal to the single-use MIC, the $MIC_{50}$ of the TE is reduced from single-use 256 μg/ml to 32 μg/ml and is reduced by 87.5%; and the $MIC_{90}$ is reduced from 512 μg/ml to 128 μg/ml and is reduced by 75%.

For the 20 MDRABs, it is indicated by FIC≤2 with the combined use of the *Pithecellobium clypearia* Benth 95% ethanol extract and the POLB that the two drugs have no antagonistic effect, wherein 20% with FIC≤0.5 have the synergistic effect. For the 20 MDRABs, when the *Pithecellobium clypearia* Benth 95% ethanol extract is smaller than or equal to the single-use MIC, the $MIC_{50}$ of the POLB is reduced from single-use 4 μg/ml to 1 μg/ml and is reduced by 75%; and the $MIC_{90}$ is reduced from 16 μg/ml to 4 μg/ml and is reduced by 75%.

It is indicated by FIC≤2 with the combined use of the *Pithecellobium clypearia* Benth 95% ethanol extract and the CAZ to the 20 MDRABs that the two drugs have no antagonistic effect, wherein 10% with FIC≤0.5 have the synergistic effect. When the *Pithecellobium clypearia* Benth 95% ethanol extract is smaller than or equal to the single-use MIC, the $MIC_{50}$ of the CAZ is reduced from single-use 512 μg/ml to 128 μg/ml and is reduced by 75%; and the $MIC_{90}$ is reduced from 512 μg/ml to 256 μg/ml and is reduced by 50%.

It is indicated by FIC≤2 with the combined use of the *Pithecellobium clypearia* Benth 95% ethanol extract and the LVX to the 20 MDRABs that the two drugs have no antagonistic effect, wherein 20% with FIC≤0.5 show that the two drugs have a certain synergistic effect. For the 20 MDRABs, when the *Pithecellobium clypearia* Benth 95% ethanol extract is smaller than or equal to the single-use MIC, the $MIC_{50}$ of the LVX is reduced from single-use 8 μg/ml to 4 μg/ml and is reduced by 50%; and the $MIC_{90}$ is reduced from 32 μg/ml to 8 μg/ml and is reduced by 75%.

II. Inhibitory and bactericidal tests of the MDRPA resistance of the EA and test of the sensibilization effect by respectively using with the LVX, the IMP, the AMK, the CAZ and the CFP Embodiment 2

1. Test method: the MDRPA (serial No.: P1-P20) strains are tested and are evaluated with reference to the method in the first embodiment.

2. Test Results:

2.1. In-vitro inhibitory test results of the *Pithecellobium clypearia* Benth water extract and the five antibiotics (the LVX, the IMP, the AMK, the CAZ and the CFP) to the MDRPAs are shown in table P1.

In-vitro bactericidal test results of the *Pithecellobium clypearia* Benth water extract to the MDRPAs are shown in table P2.

The statistic analysis on in-vitro inhibitory and bactericidal $MIC_{50}$ and $MIC_{90}$ of the EA and the five antibiotics to the MDRPAs is shown in table P3.

The statistic analysis on $MBC_{50}$ and $MBC_{90}$ of the EA to the MDRPAs is shown in table P4.

FIC values of a combined drug sensitive test of the *Pithecellobium clypearia* Benth water extract and the five antibiotics and distribution statistical results of the FIC values are shown in table P5 and table P6.

The sensibilization effects of the *Pithecellobium clypearia* Benth water extract to the five antibiotics and the $MIC_{50}$ and $MIC_{90}$ after combined use are shown in tables P7-P12.

TABLE P1

In-vitro inhibitory test results of the *Pithecellobium clypearia* Benth water extract and the five antibiotics to the MDRPAs

| | MIC (μg/ml) | | | | | |
|---|---|---|---|---|---|---|
| Strain No. | EA | LVX | IMP | AMK | CAZ | CFP |
| P1 | 800  | 32  | 32 | 1   | 32  | 128 |
| P2 | 800  | 4   | 64 | 1   | 64  | 256 |
| P3 | 800  | 8   | 64 | 4   | 4   | 16  |
| P4 | 800  | 8   | 32 | 1   | 256 | 8   |
| P5 | 800  | 1   | 64 | 2   | 64  | 512 |
| P6 | 1600 | 0.5 | 32 | 256 | 512 | 512 |
| P7 | 800  | 32  | 32 | 1   | 64  | 512 |
| P8 | 1600 | 1   | 64 | 1   | 256 | 16  |

TABLE P1-continued

In-vitro inhibitory test results of the *Pithecellobium clypearia* Benth water extract and the five antibiotics to the MDRPAs

| Strain No. | MIC (µg/ml) | | | | | |
|---|---|---|---|---|---|---|
| | EA | LVX | IMP | AMK | CAZ | CFP |
| P9 | 800 | 4 | 32 | 1 | 8 | 64 |
| P10 | 800 | 128 | 64 | 4 | 4 | 8 |
| P11 | 800 | 2 | 8 | 1 | 2 | 8 |
| P12 | 800 | 1 | 32 | 32 | 64 | 512 |
| P13 | 800 | 2 | 8 | 2 | 16 | 256 |
| P14 | 800 | 32 | 32 | 2 | 16 | 8 |
| P15 | 800 | 2 | 32 | 2 | 256 | 64 |
| P16 | 1600 | 32 | 16 | 256 | 32 | >512 |
| P17 | 800 | 4 | 16 | 1 | 32 | 16 |
| P18 | 800 | 4 | 32 | 16 | 64 | 256 |
| P19 | 800 | 16 | 64 | 1 | 4 | 64 |
| P20 | 800 | 4 | 4 | 2 | 256 | >512 |
| ATCC27853 | 400 | 1 | 4 | 2 | 4 | 8 |

TABLE P2

In-vitro bactericidal test results of the *Pithecellobium clypearia* Benth water extract to the MDRPAs

| Strain No. | MBC (µg/ml) |
|---|---|
| P1 | 1600 |
| P2 | 1600 |
| P3 | 1600 |
| P4 | 1600 |
| P5 | 1600 |
| P6 | 1600 |
| P7 | 1600 |
| P8 | 1600 |
| P9 | 1600 |
| P10 | 1600 |
| P11 | 1600 |
| P12 | 1600 |
| P13 | 1600 |
| P14 | 3200 |
| P15 | 1600 |
| P16 | 1600 |
| P17 | 1600 |
| P18 | 1600 |
| P19 | 3200 |
| P20 | 1600 |

TABLE P3

Statistical results on in-vitro inhibitory $MIC_{50}$ and $MIC_{90}$ of the *Pithecellobium clypearia* Benth water extract and the five antibiotics to the MDRPAs

| | MIC (µg/ml) | | |
|---|---|---|---|
| Drug | Range | $MIC_{50}$ | $MIC_{90}$ |
| EA | 800-1600 | 800 | 1600 |
| CAZ | 2-512 | 32 | 256 |
| CFP | 8-512 | 64 | 512 |
| AMK | 1-256 | 1 | 32 |
| IMP | 4-64 | 32 | 64 |
| LVX | 0.5-128 | 4 | 32 |

TABLE P4

Bactericidal $MBC_{50}$ and $MBC_{90}$ of the *Pithecellobium clypearia* Benth water extract to the MDRPAs

| | MBC (µg/ml) | | |
|---|---|---|---|
| Drug | Range | $MBC_{50}$ | $MBC_{90}$ |
| EA | 1600-3200 | 1600 | 1600 |

TABLE P5

FIC values of the combined drug sensitive test of the *Pithecellobium clypearia* Benth water extract and the five antibiotics

| | FIC | | | | |
|---|---|---|---|---|---|
| Strain No. | EA + CAZ | EA + CFP | EA + AMK | EA + IMP | EA + LVX |
| P1 | 0.5 | 0.375 | 0.5625 | 1 | 0.625 |
| P2 | 0.5 | 1 | 0.1875 | 0.28125 | 0.507813 |
| P3 | 0.75 | 0.375 | 0.375 | 0.28125 | 0.503906 |
| P4 | 0.5 | 1 | 1.5 | 1.0625 | 0.75 |
| P5 | 1 | 0.75 | 1.03125 | 0.5 | 0.53125 |
| P6 | 0.625 | 0.75 | 0.75 | 0.5625 | 0.3125 |
| P7 | 0.75 | 0.53125 | 0.5625 | 1.0625 | 1.000977 |
| P8 | 0.375 | 0.15625 | 0.75 | 0.28125 | 0.28125 |
| P9 | 1 | 1 | 0.5625 | 1 | 1 |
| P10 | 1 | 0.5625 | 0.375 | 0.5 | 0.375 |
| P11 | 1 | 0.75 | 1 | 0.75 | 1 |
| P12 | 0.53125 | 0.250977 | 0.3125 | 0.5625 | 1 |
| P13 | 0.5 | 0.375 | 0.28125 | 0.5 | 1 |
| P14 | 1 | 0.5625 | 0.53125 | 0.625 | 1.03125 |
| P15 | 1 | 0.5 | 0.53125 | 0.5 | 1.5 |
| P16 | 0.5 | 0.375 | 0.250244 | 0.375 | 0.5625 |
| P17 | 0.5 | 0.53125 | 0.5625 | 0.75 | 2 |
| P18 | 0.5 | 0.75 | 0.5 | 0.625 | 2.03125 |
| P19 | 1 | 0.507813 | 0.5625 | 0.5625 | 0.75 |
| P20 | 0.5 | 0.500488 | 0.625 | 1 | 0.75 |

TABLE P6

Distribution statistical results of the FIC values of the combined drug sensitive test of the *Pithecellobium clypearia* Benth water extract and the five antibiotics

| FIC Range | EA + CAZ | EA + CFP | EA + AMK | EA + IMP | EA + LVX |
|---|---|---|---|---|---|
| FIC ≤ 0.5 | 45% | 35% | 35% | 40% | 15% |
| 0.5 < FIC ≤ 1 | 55% | 65% | 55% | 50% | 60% |
| 1 < FIC ≤ 2 | — | — | 10% | 10% | 25% |
| FIC > 2 | — | — | — | — | — |

TABLE P7

Sensibilization effect of the *Pithecellobium clypearia* Benth water extract to the CAZ and MIC after combined use

| Strain No. | EA single-use MIC (µg/ml) | EA combined-use MIC (µg/ml) | CAZ single-use MIC (µg/ml) | CAZ combined-use MIC (µg/ml) |
|---|---|---|---|---|
| P1 | 800 | 200 | 32 | 8 |
| P2 | 800 | 200 | 64 | 16 |
| P3 | 800 | 200 | 4 | 2 |
| P4 | 800 | 200 | 256 | 64 |
| P5 | 800 | 400 | 64 | 32 |
| P6 | 1600 | 200 | 512 | 256 |
| P7 | 800 | 200 | 64 | 32 |
| P8 | 1600 | 200 | 256 | 64 |
| P9 | 800 | 400 | 8 | 4 |
| P10 | 800 | 400 | 4 | 2 |

TABLE P7-continued

Sensibilization effect of the *Pithecellobium clypearia* Benth water extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| P11 | 800 | 400 | 2 | 1 |
| P12 | 800 | 400 | 64 | 2 |
| P13 | 800 | 200 | 16 | 4 |
| P14 | 800 | 400 | 16 | 8 |
| P15 | 800 | 400 | 256 | 128 |
| P16 | 1600 | 400 | 32 | 8 |
| P17 | 800 | 200 | 32 | 8 |
| P18 | 800 | 200 | 64 | 16 |
| P19 | 800 | 400 | 4 | 2 |
| P20 | 800 | 200 | 256 | 64 |

TABLE P8

Sensibilization effect of the *Pithecellobium clypearia* Benth water extract to the CFP and MIC after combined use

| Strain No. | EA single-use MIC (μg/ml) | EA combined-use MIC (μg/ml) | CFP single-use MIC (μg/ml) | CFP combined-use MIC (μg/ml) |
|---|---|---|---|---|
| P1 | 800 | 100 | 128 | 32 |
| P2 | 800 | 400 | 256 | 128 |
| P3 | 800 | 200 | 16 | 2 |
| P4 | 800 | 400 | 8 | 4 |
| P5 | 800 | 200 | 512 | 256 |
| P6 | 1600 | 400 | 512 | 256 |
| P7 | 800 | 400 | 512 | 16 |
| P8 | 1600 | 200 | 16 | 0.5 |
| P9 | 800 | 400 | 64 | 32 |
| P10 | 800 | 400 | 8 | 0.5 |
| P11 | 800 | 200 | 8 | 4 |
| P12 | 800 | 200 | 512 | 0.5 |
| P13 | 800 | 200 | 256 | 32 |
| P14 | 800 | 400 | 8 | 0.5 |
| P15 | 800 | 200 | 64 | 16 |
| P16 | 1600 | 200 | 1024 | 256 |
| P17 | 800 | 400 | 16 | 0.5 |
| P18 | 800 | 200 | 256 | 128 |
| P19 | 800 | 400 | 64 | 0.5 |
| P20 | 800 | 400 | 1024 | 0.5 |

TABLE P9

Sensibilization effect of the *Pithecellobium clypearia* Benth water extract to the AMK and MIC after combined use

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| P1 | 800 | 400 | 1 | 0.0625 |
| P2 | 800 | 100 | 1 | 0.0625 |
| P3 | 800 | 100 | 4 | 1 |
| P4 | 800 | 800 | 1 | 0.5 |
| P5 | 800 | 800 | 2 | 0.0625 |
| P6 | 1600 | 800 | 256 | 64 |
| P7 | 800 | 400 | 1 | 0.0625 |
| P8 | 1600 | 400 | 1 | 0.5 |
| P9 | 800 | 400 | 1 | 0.0625 |
| P10 | 800 | 100 | 4 | 1 |
| P11 | 800 | 400 | 1 | 0.5 |
| P12 | 800 | 50 | 32 | 8 |
| P13 | 800 | 200 | 2 | 0.0625 |
| P14 | 800 | 400 | 2 | 0.0625 |
| P15 | 800 | 400 | 2 | 0.0625 |
| P16 | 1600 | 400 | 256 | 0.0625 |
| P17 | 800 | 400 | 1 | 0.0625 |
| P18 | 800 | 200 | 16 | 4 |
| P19 | 800 | 400 | 1 | 0.0625 |
| P20 | 800 | 100 | 2 | 1 |

TABLE P10

Sensibilization effect of the *Pithecellobium clypearia* Benth water extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
|---|---|---|---|---|
| P1 | 800 | 400 | 32 | 16 |
| P2 | 800 | 200 | 64 | 2 |
| P3 | 800 | 200 | 64 | 2 |
| P4 | 800 | 800 | 32 | 2 |
| P5 | 800 | 200 | 64 | 16 |
| P6 | 1600 | 800 | 32 | 2 |
| P7 | 800 | 800 | 32 | 2 |
| P8 | 1600 | 400 | 64 | 2 |
| P9 | 800 | 400 | 32 | 16 |
| P10 | 800 | 200 | 64 | 16 |
| P11 | 800 | 200 | 8 | 4 |
| P12 | 800 | 400 | 32 | 2 |
| P13 | 800 | 200 | 8 | 2 |
| P14 | 800 | 400 | 32 | 4 |
| P15 | 800 | 200 | 32 | 8 |
| P16 | 1600 | 400 | 16 | 2 |
| P17 | 800 | 400 | 16 | 4 |
| P18 | 800 | 400 | 32 | 4 |
| P19 | 800 | 400 | 64 | 4 |
| P20 | 800 | 400 | 4 | 2 |

TABLE P11

Sensibilization effect of the *Pithecellobium clypearia* Benth water extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| P1 | 800 | 400 | 32 | 4 |
| P2 | 800 | 400 | 4 | 0.03125 |
| P3 | 800 | 400 | 8 | 0.03125 |
| P4 | 800 | 200 | 8 | 4 |
| P5 | 800 | 400 | 1 | 0.03125 |
| P6 | 1600 | 400 | 0.5 | 0.03125 |
| P7 | 800 | 800 | 32 | 0.03125 |
| P8 | 1600 | 400 | 1 | 0.03125 |
| P9 | 800 | 400 | 4 | 2 |
| P10 | 800 | 100 | 128 | 32 |
| P11 | 800 | 400 | 2 | 1 |
| P12 | 800 | 400 | 1 | 0.5 |
| P13 | 800 | 400 | 2 | 1 |
| P14 | 800 | 800 | 32 | 1 |
| P15 | 800 | 800 | 2 | 1 |
| P16 | 1600 | 800 | 32 | 2 |
| P17 | 800 | 800 | 4 | 4 |
| P18 | 800 | 25 | 4 | 8 |
| P19 | 800 | 400 | 16 | 4 |
| P20 | 800 | 400 | 4 | 1 |

TABLE P12

MIC$_{50}$ and MIC$_{90}$ of the five antibiotics after combined use

| Combined drug | Antibiotic (μg/ml) | |
|---|---|---|
| | MIC$_{50}$ after combined use | MIC$_{90}$ after combined use |
| EA + CAZ | 8 | 64 |
| EA + CFP | 0.5 | 256 |
| EA + AMK | 0.0625 | 2 |
| EA + IMP | 2 | 16 |
| EA + LVX | 1 | 8 |

With the single use of the EA to the MDRPA, the MIC$_{50}$ is 800 μg/ml, the MIC$_{90}$ is 1600 μg/ml, the MBC$_{50}$ is 1600 μg/ml, and the MBC$_{90}$ is 1600 μg/ml.

For the 20 MDRPAs, it is indicated by FIC≤2 with the combined use of the EA and the CAZ that the two drugs have no antagonistic effect, wherein 45% with FIC≤0.5 have the synergistic effect. For the 20 MDRPAs, when the concentration of the EA is smaller than or equal to the single-use MIC, the MIC$_{50}$ of the CAZ is reduced from single-use 32 μg/ml to 8 μg/ml and is reduced by 75%; and the MIC$_{90}$ is reduced from 256 μg/ml to 64 μg/ml and is reduced by 75%.

It is indicated by FIC≤2 with the combined use of the EA and the CFP to the 20 MDRPAs that the two drugs have no antagonistic effect, wherein 35% with FIC≤0.5 have the synergistic effect. For the 20 MDRPAs, when the concentration of the EA is smaller than or equal to the single-use MIC, the MIC$_{50}$ of the CFP is reduced from single-use 64 μg/ml to 0.5 μg/ml and is reduced by 99.2%; and the MIC$_{90}$ is reduced from 512 μg/ml to 256 μg/ml and is reduced by 50%.

It is indicated by FIC≤2 with the combined use of the EA and the AMK that the two drugs have no antagonistic effect, wherein 35% with FIC≤0.5 have the synergistic effect. For the 20 MDRPAs, when the concentration of the EA is smaller than or equal to the single-use MIC, the MIC$_{50}$ of the AMK is reduced from single-use 1 μg/ml to 0.0625 μg/ml and is reduced by 93.75%; and the MIC$_{90}$ is reduced from 32 μg/ml to 2 μg/ml and is reduced by 93.75%.

It is indicated by FIC≤2 with the combined use of the EA and the IMP that the two drugs have no antagonistic effect, wherein 40% with FIC≤0.5 have the synergistic effect. For the 20 MDRPAs, when the concentration of the EA is smaller than or equal to the single-use MIC, the MIC$_{50}$ of the IMP is reduced from single-use 32 μg/ml to 2 μg/ml and is reduced by 93.75%; and the MIC$_{90}$ is reduced from 64 μg/ml to 16 μg/ml and is reduced by 75%.

It is indicated by FIC≤2 with the combined use of the EA and the LVX to the 20 MDRPAs that the two drugs have no antagonistic effect, wherein 15% with FIC≤0.5 show that the two drugs have a certain synergistic effect. For the 20 MDRPA, when the concentration of the EA is smaller than or equal to the single-use MIC, the MIC$_{50}$ of the LVX is reduced from single-use 4 μg/ml to 1 μg/ml and is reduced by 75%; and the MIC$_{90}$ is reduced from 32 μg/ml to 8 μg/ml and is reduced by 75%.

2.2. In-vitro inhibitory test results of the *Pithecellobium clypearia* Benth 10% ethanol extract and the five antibiotics (the LVX, the IMP, the AMK, the CAZ and the CFP) to the MDRPAs are shown in table P13.

In-vitro bactericidal test results of the *Pithecellobium clypearia* Benth 10% ethanol extract to the MDRPAs are shown in table P14.

According to statistic analysis, the in-vitro inhibitory and bactericidal MBC$_{50}$ and MBC$_{90}$ of the *Pithecellobium clypearia* Benth 10% ethanol extract and the five antibiotics to the MDRPAs are shown in table P15.

According to statistic analysis, the bactericidal MBC$_{50}$ and MBC$_{90}$ of the EA to the MDRPAs are shown in table P16.

FIC values of a combined drug sensitive test of the *Pithecellobium clypearia* Benth 10% ethanol extract and the five antibiotics and distribution statistical results of the FIC values are shown in table P17 and table P18.

The sensibilization effects of the *Pithecellobium clypearia* Benth 10% ethanol extract to the five antibiotics and the MIC$_{50}$ and MIC$_{90}$ after combined use are shown in tables P19-P24.

TABLE P13

In-vitro inhibitory test results of the *Pithecellobium clypearia* Benth 10% ethanol extract and the five antibiotics to the MDRPAs

| Strain No. | MIC(μg/ml) | | | | |
|---|---|---|---|---|---|
| | EA | LVX | IMP | AMK | CAZ | CFP |
| P1 | 800 | 32 | 32 | 1 | 32 | 128 |
| P2 | 800 | 4 | 64 | 1 | 64 | 256 |
| P3 | 800 | 8 | 64 | 4 | 4 | 16 |
| P4 | 800 | 8 | 32 | 1 | 256 | 8 |
| P5 | 800 | 1 | 64 | 2 | 64 | 512 |
| P6 | 800 | 0.5 | 32 | 256 | 512 | 512 |
| P7 | 800 | 32 | 32 | 1 | 64 | 512 |
| P8 | 1600 | 1 | 64 | 1 | 256 | 16 |
| P9 | 800 | 4 | 32 | 1 | 8 | 64 |
| P10 | 800 | 128 | 64 | 4 | 4 | 8 |
| P11 | 800 | 2 | 8 | 1 | 2 | 8 |
| P12 | 800 | 1 | 32 | 32 | 64 | 512 |
| P13 | 800 | 2 | 8 | 2 | 16 | 256 |
| P14 | 800 | 32 | 32 | 2 | 16 | 8 |
| P15 | 800 | 2 | 32 | 2 | 256 | 64 |
| P16 | 1600 | 32 | 16 | 256 | 32 | >512 |
| P17 | 800 | 4 | 16 | 1 | 32 | 16 |
| P18 | 800 | 4 | 32 | 16 | 64 | 256 |
| P19 | 800 | 16 | 64 | 1 | 4 | 64 |
| P20 | 800 | 4 | 4 | 2 | 256 | >512 |
| ATCC27853 | 400 | 1 | 4 | 2 | 4 | 8 |

TABLE P14

In-vitro bactericidal test results of the *Pithecellobium clypearia* Benth 10% ethanol extract to the MDRPAs

| Strain No. | MBC (μg/ml) |
|---|---|
| P1 | 1600 |
| P2 | 1600 |
| P3 | 1600 |
| P4 | 1600 |
| P5 | 1600 |
| P6 | 1600 |
| P7 | 1600 |
| P8 | 1600 |
| P9 | 1600 |
| P10 | 1600 |
| P11 | 1600 |
| P12 | 1600 |
| P13 | 1600 |
| P14 | 1600 |
| P15 | 1600 |
| P16 | 1600 |
| P17 | 1600 |
| P18 | 1600 |
| P19 | 3200 |
| P20 | 1600 |

TABLE P15

Statistical results on in-vitro inhibitory $MIC_{50}$ and $MIC_{90}$ of the *Pithecellobium clypearia* Benth 10% ethanol extract and the antibiotics to the MDRPAs

| Drug | MIC (μg/ml) Range | $MIC_{50}$ | $MIC_{90}$ |
|---|---|---|---|
| EA | 800-1600 | 800 | 800 |
| CAZ | 2-512 | 32 | 256 |
| CFP | 8-512 | 64 | 512 |
| AMK | 1-256 | 1 | 32 |
| IMP | 4-64 | 32 | 64 |
| LVX | 0.5-128 | 4 | 32 |

TABLE P16

Bactericidal $MBC_{50}$ and $MBC_{90}$ of the *Pithecellobium clypearia* Benth 10% ethanol extract to the MDRPAs

| Drug | MBC (μg/ml) Range | $MBC_{50}$ | $MBC_{90}$ |
|---|---|---|---|
| EA | 1600-3200 | 1600 | 1600 |

TABLE P17

FIC values of the combined drug sensitive test of the *Pithecellobium clypearia* Benth 10% ethanol extract and the five antibiotics

| Strain No. | EA + CAZ | EA + CFP | EA + AMK | EA + IMP | EA + LVX |
|---|---|---|---|---|---|
| P1 | 0.75 | 0.5 | 0.5625 | 0.75 | 0.625 |
| P2 | 0.5 | 1 | 0.3125 | 0.28125 | 0.507813 |
| P3 | 0.75 | 0.375 | 0.75 | 0.28125 | 0.503906 |
| P4 | 0.5 | 1 | 1.5 | 1 | 1 |
| P5 | 0.75 | 1 | 1.03125 | 0.5 | 0.53125 |
| P6 | 0.75 | 0.625 | 0.75 | 0.5625 | 0.3125 |
| P7 | 0.75 | 0.515625 | 0.5625 | 0.5625 | 1.000977 |
| P8 | 0.375 | 0.15625 | 0.75 | 0.28125 | 0.28125 |
| P9 | 1 | 1 | 0.5625 | 1 | 1 |
| P10 | 0.75 | 0.75 | 0.5 | 0.5 | 0.75 |
| P11 | 1 | 0.75 | 0.75 | 0.75 | 1 |
| P12 | 0.53125 | 0.253906 | 0.5 | 0.5625 | 1 |
| P13 | 0.5 | 0.375 | 0.28125 | 0.5 | 1 |
| P14 | 1 | 0.53125 | 0.53125 | 0.625 | 0.5625 |
| P15 | 1 | 0.375 | 0.53125 | 0.375 | 1 |
| P16 | 0.5 | 0.375 | 0.257813 | 0.375 | 0.375 |
| P17 | 0.5 | 0.53125 | 0.5625 | 0.625 | 1 |
| P18 | 1 | 1 | 0.5 | 0.375 | 1.5 |
| P19 | 1 | 0.507813 | 0.5625 | 0.375 | 0.75 |
| P20 | 0.5 | 0.500977 | 50.5 | 1 | 0.75 |

TABLE 18

Distribution statistical results of the FIC values of the combined drug sensitive test of the *Pithecellobium clypearia* Benth 10% ethanol extract and the five antibiotics

| FIC Range | EA + CAZ | EA + CFP | EA + AMK | EA + IMP | EA + LVX |
|---|---|---|---|---|---|
| FIC ≤ 0.5 | 35% | 35% | 30% | 50% | 15% |
| 0.5 < FIC ≤ 1 | 65% | 65% | 55% | 50% | 75% |
| 1 < FIC ≤ 2 | — | — | 15% | — | 10% |
| FIC > 2 | — | — | — | — | — |

TABLE P19

Sensibilization effect of the *Pithecellobium clypearia* Benth 10% ethanol extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| P1 | 800 | 200 | 32 | 16 |
| P2 | 800 | 200 | 64 | 16 |
| P3 | 800 | 200 | 4 | 2 |
| P4 | 800 | 200 | 256 | 64 |
| P5 | 800 | 200 | 64 | 32 |
| P6 | 800 | 200 | 512 | 256 |
| P7 | 800 | 200 | 64 | 32 |
| P8 | 1600 | 200 | 256 | 64 |
| P9 | 800 | 400 | 8 | 4 |
| P10 | 800 | 200 | 4 | 2 |
| P11 | 800 | 400 | 2 | 1 |
| P12 | 800 | 400 | 64 | 2 |
| P13 | 800 | 200 | 16 | 4 |
| P14 | 800 | 400 | 16 | 8 |
| P15 | 800 | 400 | 256 | 128 |
| P16 | 1600 | 400 | 32 | 8 |
| P17 | 800 | 200 | 32 | 8 |
| P18 | 800 | 400 | 64 | 32 |
| P19 | 800 | 400 | 4 | 2 |
| P20 | 800 | 200 | 256 | 64 |

TABLE P20

Sensibilization effect of the *Pithecellobium clypearia* Benth 10% ethanol extract to the CFP and MIC after combined use

| Strain No. | EA single-use MIC (μg/ml) | EA combined-use MIC (μg/ml) | CFP single-use MIC (μg/ml) | CFP combined-use MIC (μg/ml) |
|---|---|---|---|---|
| P1 | 800 | 200 | 128 | 32 |
| P2 | 800 | 400 | 256 | 128 |
| P3 | 800 | 200 | 16 | 2 |
| P4 | 800 | 400 | 8 | 4 |
| P5 | 800 | 400 | 512 | 256 |
| P6 | 1600 | 200 | 512 | 256 |
| P7 | 800 | 400 | 512 | 8 |
| P8 | 1600 | 200 | 16 | 0.5 |
| P9 | 800 | 400 | 64 | 32 |
| P10 | 800 | 400 | 8 | 2 |
| P11 | 800 | 200 | 8 | 4 |
| P12 | 800 | 200 | 512 | 2 |
| P13 | 800 | 200 | 256 | 32 |
| P14 | 800 | 400 | 8 | 0.25 |
| P15 | 800 | 200 | 64 | 8 |
| P16 | 1600 | 200 | 1024 | 256 |
| P17 | 800 | 400 | 16 | 0.5 |
| P18 | 800 | 400 | 256 | 128 |
| P19 | 800 | 400 | 64 | 0.5 |
| P20 | 800 | 400 | 1024 | 1 |

TABLE P21

Sensibilization effect of the *Pithecellobium clypearia* Benth 10% ethanol extract to the AMK and MIC after combined use

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| P1 | 800 | 400 | 1 | 0.0625 |
| P2 | 800 | 200 | 1 | 0.0625 |
| P3 | 800 | 200 | 4 | 2 |
| P4 | 800 | 800 | 1 | 0.5 |
| P5 | 800 | 800 | 2 | 0.0625 |
| P6 | 1600 | 800 | 256 | 64 |
| P7 | 800 | 400 | 1 | 0.0625 |
| P8 | 1600 | 400 | 1 | 0.5 |

TABLE P21-continued

Sensibilization effect of the *Pithecellobium clypearia* Benth 10% ethanol extract to the AMK and MIC after combined use

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| P9 | 800 | 400 | 1 | 0.0625 |
| P10 | 800 | 200 | 4 | 1 |
| P11 | 800 | 400 | 1 | 0.25 |
| P12 | 800 | 200 | 32 | 8 |
| P13 | 800 | 200 | 2 | 0.0625 |
| P14 | 800 | 400 | 2 | 0.0625 |
| P15 | 800 | 400 | 2 | 0.0625 |
| P16 | 1600 | 400 | 256 | 2 |
| P17 | 800 | 400 | 1 | 0.0625 |
| P18 | 800 | 200 | 16 | 4 |
| P19 | 800 | 400 | 1 | 0.0625 |
| P20 | 800 | 40000 | 2 | 1 |

TABLE P22

Sensibilization effect of the *Pithecellobium clypearia* Benth 10% ethanol extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
|---|---|---|---|---|
| P1 | 800 | 200 | 32 | 16 |
| P2 | 800 | 200 | 64 | 2 |
| P3 | 800 | 200 | 64 | 2 |
| P4 | 800 | 400 | 32 | 16 |
| P5 | 800 | 200 | 64 | 16 |
| P6 | 1600 | 800 | 32 | 2 |
| P7 | 800 | 400 | 32 | 2 |
| P8 | 1600 | 400 | 64 | 2 |
| P9 | 800 | 400 | 32 | 16 |
| P10 | 800 | 200 | 64 | 16 |
| P11 | 800 | 200 | 8 | 4 |
| P12 | 800 | 400 | 32 | 2 |
| P13 | 800 | 200 | 8 | 2 |
| P14 | 800 | 400 | 32 | 4 |
| P15 | 800 | 200 | 32 | 4 |
| P16 | 1600 | 400 | 16 | 2 |
| P17 | 800 | 400 | 16 | 2 |
| P18 | 800 | 200 | 32 | 4 |
| P19 | 800 | 200 | 64 | 8 |
| P20 | 800 | 400 | 4 | 2 |

TABLE P23

Sensibilization effect of the *Pithecellobium clypearia* Benth 10% ethanol extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| P1 | 800 | 400 | 32 | 4 |
| P2 | 800 | 400 | 4 | 0.03125 |
| P3 | 800 | 400 | 8 | 0.03125 |
| P4 | 800 | 400 | 8 | 4 |
| P5 | 800 | 400 | 1 | 0.03125 |
| P6 | 1600 | 400 | 0.5 | 0.03125 |
| P7 | 800 | 800 | 32 | 0.03125 |
| P8 | 1600 | 400 | 1 | 0.03125 |
| P9 | 800 | 400 | 4 | 2 |
| P10 | 800 | 400 | 128 | 32 |
| P11 | 800 | 400 | 2 | 1 |
| P12 | 800 | 400 | 1 | 0.5 |
| P13 | 800 | 400 | 2 | 1 |
| P14 | 800 | 400 | 32 | 2 |
| P15 | 800 | 400 | 2 | 1 |
| P16 | 1600 | 400 | 32 | 4 |
| P17 | 800 | 400 | 4 | 2 |
| P18 | 800 | 400 | 4 | 4 |
| P19 | 800 | 400 | 16 | 4 |
| P20 | 800 | 400 | 4 | 1 |

TABLE P24

$MIC_{50}$ and $MIC_{90}$ of the five antibiotics after combined use

| Combined drug | $MIC_{50}$ after combined use | $MIC_{90}$ after combined use |
|---|---|---|
| | Antibiotic (μg/ml) | |
| EA + CAZ | 16 | 64 |
| EA + CFP | 4 | 256 |
| EA + AMK | 0.0625 | 4 |
| EA + IMP | 2 | 16 |
| EA + LVX | 1 | 4 |

With the single use of the *Pithecellobium clypearia* Benth 10% ethanol extract to the MDRPA, the $MIC_{50}$ is 800 μg/ml, the $MIC_{90}$ is 1600 μg/ml, the $MBC_{50}$ is 1600 μg/ml, and the $MBC_{90}$ is 1600 μg/ml.

For the 20 MDRPAs, it is indicated by FIC≤2 with the combined use of the *Pithecellobium clypearia* Benth 10% ethanol extract and the CAZ that the two drugs have no antagonistic effect, wherein 35% with FIC≤0.5 have the synergistic effect. For the 20 MDRPAs, when the concentration of the *Pithecellobium clypearia* Benth 10% ethanol extract is smaller than or equal to the single-use MIC, the $MIC_{50}$ of the CAZ is reduced from single-use 32 μg/ml to 16 μg/ml and is reduced by 50%; and the $MIC_{90}$ is reduced from 256 μg/ml to 64 μg/ml and is reduced by 75%.

It is indicated by FIC≤2 with the combined use of the *Pithecellobium clypearia* Benth 10% ethanol extract and the CFP to the 20 MDRPAs that the two drugs have no antagonistic effect, wherein 35% with FIC≤0.5 have the synergistic effect. For the 20 MDRPAs, when the concentration of the *Pithecellobium clypearia* Benth 10% ethanol extract is smaller than or equal to the single-use MIC, the $MIC_{50}$ of the CFP is reduced from single-use 64 μg/ml to 4 μg/ml and is reduced by 93.75%; and the $MIC_{90}$ is reduced from 512 μg/ml to 256 μg/ml and is reduced by 50%.

It is indicated by FIC≤2 with the combined use of the *Pithecellobium clypearia* Benth 10% ethanol extract and the AMK that the two drugs have no antagonistic effect, wherein 30% with FIC≤0.5 have the synergistic effect. For the 20 MDRPAs, when the concentration of the *Pithecellobium clypearia* Benth 10% ethanol extract is smaller than or equal to the single-use MIC, the $MIC_{50}$ of the AMK is reduced from single-use 1 μg/ml to 0.0625 μg/ml and is reduced by 93.75%; and the $MIC_{90}$ is reduced from 32 μg/ml to 4 μg/ml and is reduced by 87.5%.

It is indicated by FIC≤2 with the combined use of the *Pithecellobium clypearia* Benth 10% ethanol extract and the IMP that the two drugs have no antagonistic effect, wherein 50% with FIC≤0.5 have the synergistic effect. For the 20 MDRPAs, when the concentration of the *Pithecellobium clypearia* Benth 10% ethanol extract is smaller than or equal to the single-use MIC, the $MIC_{50}$ of the IMP is reduced from single-use 32 µg/ml to 2 µg/ml and is reduced by 93.75%; and the $MIC_{90}$ is reduced from 64 µg/ml to 16 µg/ml and is reduced by 75%.

It is indicated by FIC≤2 with the combined use of the *Pithecellobium clypearia* Benth 10% ethanol extract and the LVX to the 20 MDRPAs that the two drugs have no antagonistic effect, wherein 15% with FIC≤0.5 show that the two drugs have a certain synergistic effect. For the 20 MDRPA, when the concentration of the *Pithecellobium clypearia* Benth 10% ethanol extract is smaller than or equal to the single-use MIC, the $MIC_{50}$ of the LVX is reduced from single-use 4 µg/ml to 1 µg/ml and is reduced by 75%; and the $MIC_{90}$ is reduced from 32 µg/ml to 4 µg/ml and is reduced by 87.5%.

2.3. In-vitro inhibitory test results of the *Pithecellobium clypearia* Benth 60% ethanol extract and the five antibiotics (the LVX, the IMP, the AMK, the CAZ and the CFP) to the MDRPAs are shown in table P25.

In-vitro bactericidal test results of the *Pithecellobium clypearia* Benth 60% ethanol extract to the MDRPAs are shown in table P26.

The statistic analysis on in-vitro inhibitory and bactericidal $MIC_{50}$ and $MIC_{90}$ of the *Pithecellobium clypearia* Benth 60% ethanol extract and the five antibiotics to the MDRPAs is shown in table P27.

The statistic analysis on bactericidal $MBC_{50}$ and $MBC_{90}$ of the EA to the MDRPAs is shown in table P28.

FIC values of a combined drug sensitive test of the *Pithecellobium clypearia* Benth 60% ethanol extract and the five antibiotics and distribution statistical results of the FIC values are shown in table P29 and table P30.

The sensibilization effects of the *Pithecellobium clypearia* Benth 60% ethanol extract to the five antibiotics and the $MIC_{50}$ and $MIC_{90}$ after combined use are shown in tables P31-P36.

TABLE P25

In-vitro inhibitory test results of the *Pithecellobium clypearia* Benth 60% ethanol extract and the five antibiotics to the MDRPAs

| Strain No. | MIC(µg/ml) | | | | | |
|---|---|---|---|---|---|---|
| | EA | LVX | IMP | AMK | CAZ | CFP |
| P1 | 400 | 32 | 32 | 1 | 32 | 128 |
| P2 | 200 | 4 | 64 | 1 | 64 | 256 |
| P3 | 400 | 8 | 64 | 4 | 4 | 16 |
| P4 | 400 | 8 | 32 | 1 | 256 | 8 |
| P5 | 400 | 1 | 64 | 2 | 64 | 512 |
| P6 | 400 | 0.5 | 32 | 256 | 512 | 512 |
| P7 | 400 | 32 | 32 | 1 | 64 | 512 |
| P8 | 800 | 1 | 64 | 1 | 256 | 16 |
| P9 | 400 | 4 | 32 | 1 | 8 | 64 |
| P10 | 400 | 128 | 64 | 4 | 4 | 8 |
| P11 | 400 | 2 | 8 | 1 | 2 | 8 |
| P12 | 400 | 1 | 32 | 32 | 64 | 512 |
| P13 | 400 | 2 | 8 | 2 | 16 | 256 |
| P14 | 800 | 32 | 32 | 2 | 16 | 8 |
| P15 | 400 | 2 | 32 | 2 | 256 | 64 |
| P16 | 800 | 32 | 16 | 256 | 32 | >512 |
| P17 | 400 | 4 | 16 | 1 | 32 | 16 |
| P18 | 400 | 4 | 32 | 16 | 64 | 256 |
| P19 | 800 | 16 | 64 | 1 | 4 | 64 |
| P20 | 800 | 4 | 4 | 2 | 256 | >512 |
| ATCC27853 | 400 | 1 | 4 | 2 | 4 | 8 |

TABLE P26

In-vitro bactericidal test results of the *Pithecellobium clypearia* Benth 60% ethanol extract to the MDRPAs

| Strain No. | MBC (µg/ml) |
|---|---|
| P1 | 400 |
| P2 | 400 |
| P3 | 800 |
| P4 | 800 |
| P5 | 800 |
| P6 | 800 |
| P7 | 800 |
| P8 | 800 |
| P9 | 1600 |
| P10 | 1600 |
| P11 | 1600 |
| P12 | 1600 |
| P13 | 1600 |
| P14 | 1600 |
| P15 | 1600 |
| P16 | 1600 |
| P17 | 1600 |
| P18 | 1600 |
| P19 | 1600 |
| P20 | 1600 |

TABLE P27

Statistical results on in-vitro inhibitory $MIC_{50}$ and $MIC_{90}$ of the *Pithecellobium clypearia* Benth 60% ethanol extract and the five antibiotics to the MDRPAs

| Drug | MIC (µg/ml) | | |
|---|---|---|---|
| | Range | $MIC_{50}$ | $MIC_{90}$ |
| EA | 200-800 | 400 | 800 |
| CAZ | 2-512 | 32 | 256 |
| CFP | 8-512 | 64 | 512 |
| AMK | 1-256 | 1 | 32 |
| IMP | 4-64 | 32 | 64 |
| LVX | 0.5-128 | 4 | 32 |

TABLE P28

Bactericidal $MBC_{50}$ and $MBC_{90}$ of the *Pithecellobium clypearia* Benth 60% ethanol extract to the MDRPAs

| Drug | MBC (µg/ml) | | |
|---|---|---|---|
| | Range | $MBC_{50}$ | $MBC_{90}$ |
| EA | 400-1600 | 1600 | 1600 |

TABLE P29

FIC values of the combined drug sensitive test of the *Pithecellobium clypearia* Benth 60% ethanol extract and the five antibiotics

| Strain No. | FIC | | | | |
|---|---|---|---|---|---|
| | EA + CAZ | EA + CFP | EA + AMK | EA + IMP | EA + LVX |
| P1 | 0.375 | 0.375 | 1.0625 | 0.625 | 0.25 |
| P2 | 0.625 | 0.75 | 0.5625 | 0.53125 | 0.5078 |
| P3 | 1.125 | 1.03125 | 0.5 | 0.15625 | 1.0039 |
| P4 | 0.375 | 1.0625 | 1.5 | 1.0625 | 1 |
| P5 | 1.0078 | 0.625 | 1.03125 | 0.75 | 1.03125 |
| P6 | 0.75 | 1 | 1.125 | 1.0625 | 1.0625 |
| P7 | 1 | 0.625 | 1.0625 | 1.0625 | 1.0010 |
| P8 | 0.3125 | 0.53125 | 0.5625 | 0.53125 | 0.53125 |
| P9 | 1.0625 | 0.625 | 0.5625 | 0.75 | 1 |
| P10 | 1.125 | 1.0625 | 0.375 | 0.75 | 0.5 |

TABLE P29-continued

FIC values of the combined drug sensitive test of the *Pithecellobium clypearia* Benth 60% ethanol extract and the five antibiotics

| Strain No. | FIC | | | | |
|---|---|---|---|---|---|
| | EA + CAZ | EA + CFP | EA + AMK | EA + IMP | EA + LVX |
| P11 | 1.25 | 1.0625 | 0.75 | 1.25 | 2.0625 |
| P12 | 0.5078 | 0.5010 | 0.375 | 0.5625 | 1.5 |
| P13 | 0.75 | 0.375 | 0.53125 | 0.5 | 1.015625 |
| P14 | 0.375 | 0.5625 | 0.53125 | 0.5 | 1.03125 |
| P15 | 0.75 | 0.375 | 1.03125 | 0.75 | 2.5 |
| P16 | 0.375 | 0.3125 | 0.5002 | 0.625 | 0.53125 |
| P17 | 0.5 | 1.03125 | 1.0625 | 1.125 | 3 |
| P18 | 0.5 | 0.625 | 0.375 | 1.0625 | 2.0625 |
| P19 | 0.625 | 0.5078 | 0.5625 | 0.53125 | 0.625 |
| P20 | 0.3125 | 0.5005 | 0.5625 | 0.625 | 0.625 |

TABLE P30

Distribution statistical results of the FIC values of the combined drug sensitive test of the *Pithecellobium clypearia* Benth 60% ethanol extract and the five antibiotics

| FIC Range | EA + CAZ | EA + CFP | EA + AMK | EA + IMP | EA + LVX |
|---|---|---|---|---|---|
| FIC ≤ 0.5 | 40% | 20% | 20% | 15% | 10% |
| 0.5 < FIC ≤ 1 | 35% | 55% | 45% | 55% | 35% |
| 1 < FIC ≤ 2 | 25% | 25% | 35% | 30% | 35% |
| FIC > 2 | — | — | — | — | 20% |

TABLE P31

Sensibilization effect of the *Pithecellobium clypearia* Benth 60% ethanol extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| P1 | 400 | 50 | 32 | 8 |
| P2 | 200 | 100 | 64 | 8 |
| P3 | 400 | 50 | 4 | 4 |
| P4 | 400 | 50 | 256 | 64 |
| P5 | 400 | 400 | 64 | 0.5 |
| P6 | 400 | 100 | 512 | 256 |
| P7 | 400 | 200 | 64 | 32 |
| P8 | 800 | 50 | 256 | 64 |
| P9 | 400 | 400 | 8 | 0.5 |
| P10 | 400 | 400 | 4 | 0.5 |
| P11 | 400 | 400 | 2 | 0.5 |
| P12 | 400 | 200 | 64 | 0.5 |
| P13 | 400 | 100 | 16 | 8 |
| P14 | 800 | 100 | 16 | 4 |
| P15 | 400 | 100 | 256 | 128 |
| P16 | 800 | 100 | 32 | 8 |
| P17 | 400 | 100 | 32 | 8 |
| P18 | 400 | 100 | 64 | 16 |
| P19 | 800 | 400 | 4 | 0.5 |
| P20 | 800 | 50 | 256 | 64 |

TABLE P32

Sensibilization effect of the *Pithecellobium clypearia* Benth 60% ethanol extract to the CFP and MIC after combined use

| Strain No. | EA single-use MIC (μg/ml) | EA combined-use MIC (μg/ml) | CFP single-use MIC (μg/ml) | CFP combined-use MIC (μg/ml) |
|---|---|---|---|---|
| P1 | 400 | 50 | 128 | 32 |
| P2 | 200 | 50 | 256 | 128 |
| P3 | 400 | 400 | 16 | 0.5 |
| P4 | 400 | 400 | 8 | 0.5 |
| P5 | 400 | 50 | 512 | 256 |
| P6 | 400 | 200 | 512 | 256 |
| P7 | 400 | 50 | 512 | 256 |
| P8 | 800 | 400 | 16 | 0.5 |
| P9 | 400 | 50 | 64 | 32 |
| P10 | 400 | 400 | 8 | 0.5 |
| P11 | 400 | 400 | 8 | 0.5 |
| P12 | 400 | 200 | 512 | 0.5 |
| P13 | 400 | 100 | 256 | 32 |
| P14 | 800 | 400 | 8 | 0.5 |
| P15 | 400 | 50 | 64 | 16 |
| P16 | 800 | 50 | 1024 | 256 |
| P17 | 400 | 400 | 16 | 0.5 |
| P18 | 400 | 50 | 256 | 128 |
| P19 | 800 | 400 | 64 | 0.5 |
| P20 | 800 | 400 | 1024 | 0.5 |

TABLE P33

Sensibilization effect of the *Pithecellobium clypearia* Benth 60% ethanol extract to the AMK and MIC after combined use

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| P1 | 400 | 400 | 1 | 0.0625 |
| P2 | 200 | 100 | 1 | 0.0625 |
| P3 | 400 | 100 | 4 | 1 |
| P4 | 400 | 400 | 1 | 0.5 |
| P5 | 400 | 400 | 2 | 0.0625 |
| P6 | 400 | 400 | 256 | 32 |
| P7 | 400 | 400 | 1 | 0.0625 |
| P8 | 800 | 50 | 1 | 0.5 |
| P9 | 400 | 200 | 1 | 0.0625 |
| P10 | 400 | 50 | 4 | 1 |
| P11 | 400 | 100 | 1 | 0.5 |
| P12 | 400 | 50 | 32 | 8 |
| P13 | 400 | 200 | 2 | 0.0625 |
| P14 | 800 | 400 | 2 | 0.0625 |
| P15 | 400 | 400 | 2 | 0.0625 |
| P16 | 800 | 400 | 256 | 0.0625 |
| P17 | 400 | 400 | 1 | 0.0625 |
| P18 | 400 | 100 | 16 | 2 |
| P19 | 800 | 400 | 1 | 0.0625 |
| P20 | 800 | 50 | 2 | 1 |

TABLE P34

Sensibilization effect of the *Pithecellobium clypearia* Benth 60% ethanol extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
|---|---|---|---|---|
| P1 | 400 | 50 | 32 | 16 |
| P2 | 200 | 100 | 64 | 2 |
| P3 | 400 | 50 | 64 | 2 |
| P4 | 400 | 400 | 32 | 2 |
| P5 | 400 | 200 | 64 | 16 |
| P6 | 400 | 400 | 32 | 2 |
| P7 | 400 | 400 | 32 | 2 |
| P8 | 800 | 400 | 64 | 2 |
| P9 | 400 | 100 | 32 | 16 |
| P10 | 400 | 200 | 64 | 16 |

TABLE P34-continued

Sensibilization effect of the *Pithecellobium clypearia* Benth 60% ethanol extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
|---|---|---|---|---|
| P11 | 400 | 400 | 8 | 2 |
| P12 | 400 | 200 | 32 | 2 |
| P13 | 400 | 100 | 8 | 2 |
| P14 | 800 | 200 | 32 | 8 |
| P15 | 400 | 200 | 32 | 8 |
| P16 | 800 | 400 | 16 | 2 |
| P17 | 400 | 400 | 16 | 2 |
| P18 | 400 | 400 | 32 | 2 |
| P19 | 800 | 400 | 64 | 2 |
| P20 | 800 | 100 | 4 | 2 |

TABLE P35

Sensibilization effect of the *Pithecellobium clypearia* Benth 60% ethanol extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| P1  | 400 | 50  | 32  | 4 |
| P2  | 200 | 100 | 4   | 0.03125 |
| P3  | 400 | 400 | 8   | 0.03125 |
| P4  | 400 | 200 | 8   | 4 |
| P5  | 400 | 400 | 1   | 0.03125 |
| P6  | 400 | 400 | 0.5 | 0.03125 |
| P7  | 400 | 400 | 32  | 0.03125 |
| P8  | 800 | 400 | 1   | 0.03125 |
| P9  | 400 | 200 | 4   | 2 |
| P10 | 400 | 100 | 128 | 32 |
| P11 | 400 | 25  | 2   | 4 |
| P12 | 400 | 400 | 1   | 0.5 |
| P13 | 400 | 400 | 2   | 0.03125 |
| P14 | 800 | 800 | 32  | 1 |
| P15 | 400 | 800 | 2   | 1 |
| P16 | 800 | 25  | 32  | 16 |
| P17 | 400 | 800 | 4   | 4 |
| P18 | 400 | 25  | 4   | 8 |
| P19 | 800 | 100 | 16  | 8 |
| P20 | 800 | 100 | 4   | 2 |

TABLE P36

$MIC_{50}$ and $MIC_{90}$ of the five antibiotics after combined use

| Combined drug | $MIC_{50}$ after combined use | $MIC_{90}$ after combined use |
|---|---|---|
| EA + CAZ | 8 | 64 |
| EA + CFP | 4 | 256 |
| EA + AMK | 0.0625 | 4 |
| EA + IMP | 2 | 16 |
| EA + LVX | 1 | 8 |

With the single use of the *Pithecellobium clypearia* Benth 60% ethanol extract to the MDRPA, the $MIC_{50}$ is 800 μg/ml, the $MIC_{90}$ is 1600 μg/ml, the $MBC_{50}$ is 1600 μg/ml, and the $MBC_{90}$ is 1600 μg/ml.

For the 20 MDRPAs, it is indicated by FIC≤2 with the combined use of the *Pithecellobium clypearia* Benth 60% ethanol extract and the CAZ that the two drugs have no antagonistic effect, wherein 40% with FIC≤0.5 have the synergistic effect. For the 20 MDRPAs, when the concentration of the *Pithecellobium clypearia* Benth 60% ethanol extract is smaller than or equal to the single-use MIC, the $MIC_{50}$ of the CAZ is reduced from single-use 32 μg/ml to 8 μg/ml and is reduced by 75%; and the $MIC_{90}$ is reduced from 256 μg/ml to 64 μg/ml and is reduced by 75%.

It is indicated by FIC≤2 with the combined use of the *Pithecellobium clypearia* Benth 60% ethanol extract and the CFP to the 20 MDRPAs that the two drugs have no antagonistic effect, wherein 20% with FIC≤0.5 have the synergistic effect. For the 20 MDRPAs, when the concentration of the *Pithecellobium clypearia* Benth 60% ethanol extract is smaller than or equal to the single-use MIC, the $MIC_{50}$ of the CFP is reduced from single-use 64 μg/ml to 4 μg/ml and is reduced by 93.75%; and the $MIC_{90}$ is reduced from 512 μg/ml to 256 μg/ml and is reduced by 50%.

It is indicated by FIC≤2 with the combined use of the *Pithecellobium clypearia* Benth 60% ethanol extract and the AMK that the two drugs have no antagonistic effect, wherein 20% with FIC≤0.5 have the synergistic effect. For the 20 MDRPAs, when the concentration of the *Pithecellobium clypearia* Benth 60% ethanol extract is smaller than or equal to the single-use MIC, the $MIC_{50}$ of the AMK is reduced from single-use 1 μg/ml to 0.0625 μg/ml and is reduced by 93.75%; and the $MIC_{90}$ is reduced from 32 μg/ml to 2 μg/ml and is reduced by 93.75%.

It is indicated by FIC≤2 with the combined use of the *Pithecellobium clypearia* Benth 60% ethanol extract and the IMP that the two drugs have no antagonistic effect, wherein 15% with FIC≤0.5 have the synergistic effect. For the 20 MDRPAs, when the concentration of the *Pithecellobium clypearia* Benth 60% ethanol extract is smaller than or equal to the single-use MIC, the $MIC_{50}$ of the IMP is reduced from single-use 32 μg/ml to 2 μg/ml and is reduced by 93.75%; and the $MIC_{90}$ is reduced from 64 μg/ml to 16 μg/ml and is reduced by 75%.

With the combined use of the *Pithecellobium clypearia* Benth 60% ethanol extract and the LVX to the 20 MDRPAs, there are four strains with FIC greater than 2 and has the antagonistic effect, wherein 10% with FIC≤0.5 show that the two drugs have a certain synergistic effect. For the 20 MDRPA, when the concentration of the *Pithecellobium clypearia* Benth 60% ethanol extract is smaller than or equal to the single-use MIC, the $MIC_{50}$ of the LVX is reduced from single-use 4 μg/ml to 1 μg/ml and is reduced by 75%; and the $MIC_{90}$ is reduced from 32 μg/ml to 8 μg/ml and is reduced by 75%.

2.4. In-vitro inhibitory test results of the *Pithecellobium clypearia* Benth 95% ethanol extract and the five antibiotics (the LVX, the IMP, the AMK, the CAZ and the CFP) to the MDRPAs are shown in table P37.

In-vitro bactericidal test results of the *Pithecellobium clypearia* Benth 95% ethanol extract to the MDRPAs are shown in table P38.

The statistic analysis on in-vitro inhibitory and bactericidal $MIC_{50}$ and $MIC_{90}$ of the *Pithecellobium clypearia* Benth 95% ethanol extract and the five antibiotics to the MDRPAs is shown in table P39.

The statistic analysis on bactericidal $MBC_{50}$ and $MBC_{90}$ of the *Pithecellobium clypearia* Benth 95% ethanol extract to the MDRPAs is shown in table P40.

FIC values of a combined drug sensitive test of the *Pithecellobium clypearia* Benth 95% ethanol extract and the five antibiotics and distribution statistical results of the FIC values are shown in table P41 and table P42.

The sensibilization effects of the *Pithecellobium clypearia* Benth 95% ethanol extract to the five antibiotics and the $MIC_{50}$ and $MIC_{90}$ after combined use are shown in tables P43-P48.

TABLE P37

In-vitro inhibitory test results of the *Pithecellobium clypearia* Benth 95% ethanol extract and the five antibiotics to the MDRPAs

| | MIC(μg/ml) | | | | | |
|---|---|---|---|---|---|---|
| Strain No. | EA | LVX | IMP | AMK | CAZ | CFP |
| P1 | 800 | 32 | 32 | 1 | 32 | 128 |
| P2 | 800 | 4 | 64 | 1 | 64 | 256 |
| P3 | 800 | 8 | 64 | 4 | 4 | 16 |
| P4 | 800 | 8 | 32 | 1 | 256 | 8 |
| P5 | 800 | 1 | 64 | 2 | 64 | 512 |
| P6 | 800 | 0.5 | 32 | 256 | 512 | 512 |
| P7 | 800 | 32 | 32 | 1 | 64 | 512 |
| P8 | 800 | 1 | 64 | 1 | 256 | 16 |
| P9 | 800 | 4 | 32 | 1 | 8 | 64 |
| P10 | 800 | 128 | 64 | 4 | 4 | 8 |
| P11 | 800 | 2 | 8 | 1 | 2 | 8 |
| P12 | 800 | 1 | 32 | 32 | 64 | 512 |
| P13 | 800 | 2 | 8 | 2 | 16 | 256 |
| P14 | 800 | 32 | 32 | 2 | 16 | 8 |
| P15 | 800 | 2 | 32 | 2 | 256 | 64 |
| P16 | 800 | 32 | 16 | 256 | 32 | >512 |
| P17 | 800 | 4 | 16 | 1 | 32 | 16 |
| P18 | 800 | 4 | 32 | 16 | 64 | 256 |
| P19 | 800 | 16 | 64 | 1 | 4 | 64 |
| P20 | 800 | 4 | 4 | 2 | 256 | >512 |
| ATCC27853 | 400 | 1 | 4 | 2 | 4 | 8 |

TABLE P38

In-vitro bactericidal test results of the *Pithecellobium clypearia* Benth 95% ethanol extract to the MDRPAs

| Strain No. | MBC (μg/ml) |
|---|---|
| P1 | 1600 |
| P2 | 1600 |
| P3 | 1600 |
| P4 | 1600 |
| P5 | 1600 |
| P6 | 1600 |
| P7 | 1600 |
| P8 | 1600 |
| P9 | 1600 |
| P10 | 1600 |
| P11 | 1600 |
| P12 | 1600 |
| P13 | 1600 |
| P14 | 1600 |
| P15 | 1600 |
| P16 | 3200 |
| P17 | 1600 |
| P18 | 1600 |
| P19 | 1600 |
| P20 | 1600 |

TABLE P39

Statistical results on in-vitro inhibitory $MIC_{50}$ and $MIC_{90}$ of the *Pithecellobium clypearia* Benth 95% ethanol extract and the five antibiotics to the MDRPAs

| | MIC (μg/ml) | | |
|---|---|---|---|
| Drug | Range | $MIC_{50}$ | $MIC_{90}$ |
| EA | 800 | 800 | 800 |
| CAZ | 2-512 | 32 | 256 |
| CFP | 8-512 | 64 | 512 |
| AMK | 1-256 | 1 | 32 |
| IMP | 4-64 | 32 | 64 |
| LVX | 0.5-128 | 4 | 32 |

TABLE P40

Bactericidal $MBC_{50}$ and $MBC_{90}$ of the *Pithecellobium clypearia* Benth 95% ethanol extract to the MDRPAs

| | MBC (μg/ml) | | |
|---|---|---|---|
| Drug | Range | $MBC_{50}$ | $MBC_{90}$ |
| EA | 1600-3200 | 1600 | 1600 |

TABLE P41

FIC values of the combined drug sensitive test of the *Pithecellobium clypearia* Benth 95% ethanol extract and the five antibiotics

| Strain | FIC | | | | |
|---|---|---|---|---|---|
| No. | EA + CAZ | EA + CFP | EA + AMK | EA + IMP | EA + LVX |
| P1 | 1 | 0.5 | 0.5625 | 1 | 0.625 |
| P2 | 0.75 | 1 | 0.3125 | 0.3125 | 0.507813 |
| P3 | 0.75 | 0.5 | 1 | 0.3125 | 0.503906 |
| P4 | 1 | 1 | 1.5 | 0.75 | 1 |
| P5 | 1 | 1 | 1.03125 | 0.375 | 1.03125 |
| P6 | 1 | 0.75 | 1.125 | 0.5625 | 1.0625 |
| P7 | 0.75 | 0.515625 | 0.37 | 0.5625 | 1.000977 |
| P8 | 0.5 | 0.28125 | 0.75 | 0.5 | 0.53125 |
| P9 | 1 | 1 | 0.3125 | 1 | 1 |
| P10 | 1 | 0.375 | 0.5 | 0.5 | 0.75 |
| P11 | 1 | 1 | 1 | 0.75 | 1 |
| P12 | 0.53125 | 0.503906 | 0.5 | 0.5625 | 1 |
| P13 | 0.5 | 0.375 | 0.28125 | 0.75 | 1 |
| P14 | 1 | 0.53125 | 0.53125 | 0.625 | 0.3125 |
| P15 | 1 | 0.375 | 0.28125 | 0.375 | 1 |
| P16 | 0.375 | 0.5 | 0.507813 | 0.625 | 0.625 |
| P17 | 0.375 | 0.53125 | 0.5625 | 0.625 | 1 |
| P18 | 1 | 0.75 | 0.5 | 0.375 | 1.5 |
| P19 | 0.75 | 0.28125 | 0.5625 | 0.375 | 0.5 |
| P20 | 0.5 | 0.500977 | 1 | 1 | 0.75 |

TABLE P42

Distribution statistical results of the FIC values of the combined drug sensitive test of the *Pithecellobium clypearia* Benth 95% ethanol extract and the five antibiotics

| FIC Strain No. | EA + CAZ | EA + CFP | EA + AMK | EA + IMP | EA + LVX |
|---|---|---|---|---|---|
| FIC ≤ 0.5 | 25% | 40% | 40% | 40% | 10% |
| 0.5 < FIC ≤ 1 | 75% | 60% | 45% | 60% | 70% |
| 1 < FIC ≤ 2 | — | — | 15% | — | 20% |
| FIC > 2 | — | — | — | — | — |

TABLE P43

Sensibilization effect of the *Pithecellobium clypearia* Benth 95% ethanol extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| P1 | 800 | 400 | 32 | 16 |
| P2 | 800 | 400 | 64 | 16 |
| P3 | 800 | 400 | 4 | 1 |
| P4 | 800 | 400 | 256 | 128 |
| P5 | 800 | 400 | 64 | 32 |
| P6 | 800 | 400 | 512 | 256 |
| P7 | 800 | 200 | 64 | 32 |
| P8 | 800 | 200 | 256 | 64 |
| P9 | 800 | 400 | 8 | 4 |
| P10 | 800 | 400 | 4 | 2 |
| P11 | 800 | 400 | 2 | 1 |

TABLE P43-continued

Sensibilization effect of the *Pithecellobium clypearia* Benth 95% ethanol extract to the CAZ and MIC after combined use

| Strain No. | EA single-use MIC (μg/ml) | EA combined-use MIC (μg/ml) | CAZ single-use MIC (μg/ml) | CAZ combined-use MIC (μg/ml) |
|---|---|---|---|---|
| P12 | 800 | 400 | 64 | 2 |
| P13 | 800 | 200 | 16 | 4 |
| P14 | 800 | 400 | 16 | 8 |
| P15 | 800 | 400 | 256 | 128 |
| P16 | 800 | 200 | 32 | 4 |
| P17 | 800 | 200 | 32 | 4 |
| P18 | 800 | 400 | 64 | 32 |
| P19 | 800 | 400 | 4 | 1 |
| P20 | 800 | 200 | 256 | 64 |

TABLE P44

Sensibilization effect of the *Pithecellobium clypearia* Benth 95% ethanol extract to the CFP and MIC after combined use

| Strain No. | EA single-use MIC (μg/ml) | EA combined-use MIC (μg/ml) | CFP single-use MIC (μg/ml) | CFP combined-use MIC (μg/ml) |
|---|---|---|---|---|
| P1 | 800 | 200 | 128 | 32 |
| P2 | 800 | 400 | 256 | 128 |
| P3 | 800 | 200 | 16 | 4 |
| P4 | 800 | 400 | 8 | 4 |
| P5 | 800 | 400 | 512 | 256 |
| P6 | 800 | 400 | 512 | 128 |
| P7 | 800 | 400 | 512 | 8 |
| P8 | 800 | 200 | 16 | 0.5 |
| P9 | 800 | 400 | 64 | 32 |
| P10 | 800 | 200 | 8 | 1 |
| P11 | 800 | 400 | 8 | 4 |
| P12 | 800 | 400 | 512 | 2 |
| P13 | 800 | 200 | 256 | 32 |
| P14 | 800 | 400 | 8 | 0.25 |
| P15 | 800 | 200 | 64 | 8 |
| P16 | 800 | 200 | 1024 | 256 |
| P17 | 800 | 400 | 16 | 0.5 |
| P18 | 800 | 200 | 256 | 128 |
| P19 | 800 | 200 | 64 | 2 |
| P20 | 800 | 400 | 1024 | 1 |

TABLE P45

Sensibilization effect of the *Pithecellobium clypearia* Benth 95% ethanol extract to the AMK and MIC after combined use

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| P1 | 800 | 400 | 1 | 0.0625 |
| P2 | 800 | 200 | 1 | 0.0625 |
| P3 | 800 | 400 | 4 | 2 |
| P4 | 800 | 800 | 1 | 0.5 |
| P5 | 800 | 800 | 2 | 0.0625 |
| P6 | 800 | 800 | 256 | 32 |
| P7 | 800 | 200 | 1 | 0.12 |
| P8 | 800 | 200 | 1 | 0.5 |
| P9 | 800 | 200 | 1 | 0.0625 |
| P10 | 800 | 200 | 4 | 1 |
| P11 | 800 | 400 | 1 | 0.5 |
| P12 | 800 | 200 | 32 | 8 |
| P13 | 800 | 200 | 2 | 0.0625 |
| P14 | 800 | 400 | 2 | 0.0625 |
| P15 | 800 | 200 | 2 | 0.0625 |
| P16 | 800 | 400 | 256 | 2 |
| P17 | 800 | 400 | 1 | 0.0625 |
| P18 | 800 | 200 | 16 | 4 |
| P19 | 800 | 400 | 1 | 0.0625 |
| P20 | 800 | 400 | 2 | 1 |

TABLE P46

Sensibilization effect of the *Pithecellobium clypearia* Benth 95% ethanol extract to the IMP and MIC after combined use

| Strain No. | EA single-use MIC (μg/ml) | EA combined-use MIC (μg/ml) | IMP single-use MIC (μg/ml) | IMP combined-use MIC (μg/ml) |
|---|---|---|---|---|
| P1 | 800 | 400 | 32 | 16 |
| P2 | 800 | 200 | 64 | 4 |
| P3 | 800 | 200 | 64 | 4 |
| P4 | 800 | 400 | 32 | 8 |
| P5 | 800 | 200 | 64 | 8 |
| P6 | 800 | 400 | 32 | 2 |
| P7 | 800 | 400 | 32 | 2 |
| P8 | 800 | 200 | 64 | 16 |
| P9 | 800 | 400 | 32 | 16 |
| P10 | 800 | 200 | 64 | 16 |
| P11 | 800 | 200 | 8 | 4 |
| P12 | 800 | 400 | 32 | 2 |
| P13 | 800 | 400 | 8 | 2 |
| P14 | 800 | 400 | 32 | 4 |
| P15 | 800 | 200 | 32 | 4 |
| P16 | 800 | 400 | 16 | 2 |
| P17 | 800 | 400 | 16 | 2 |
| P18 | 800 | 200 | 32 | 4 |
| P19 | 800 | 200 | 64 | 8 |
| P20 | 800 | 400 | 4 | 2 |

TABLE P47

Sensibilization effect of the *Pithecellobium clypearia* Benth 95% ethanol extract to the LVX and MIC after combined use

| Strain No. | EA single-use MIC (μg/ml) | EA combined-use MIC (μg/ml) | LVX single-use MIC (μg/ml) | LVX combined-use MIC (μg/ml) |
|---|---|---|---|---|
| P1 | 800 | 400 | 32 | 4 |
| P2 | 800 | 400 | 4 | 0.03125 |
| P3 | 800 | 400 | 8 | 0.03125 |
| P4 | 800 | 400 | 8 | 4 |
| P5 | 800 | 800 | 1 | 0.03125 |
| P6 | 800 | 800 | 0.5 | 0.03125 |
| P7 | 800 | 800 | 32 | 0.03125 |
| P8 | 800 | 400 | 1 | 0.03125 |
| P9 | 800 | 400 | 4 | 2 |
| P10 | 800 | 400 | 128 | 32 |
| P11 | 800 | 400 | 2 | 1 |
| P12 | 800 | 400 | 1 | 0.5 |
| P13 | 800 | 400 | 2 | 1 |
| P14 | 800 | 200 | 32 | 2 |
| P15 | 800 | 400 | 2 | 1 |
| P16 | 800 | 400 | 32 | 4 |
| P17 | 800 | 400 | 4 | 2 |
| P18 | 800 | 400 | 4 | 4 |
| P19 | 800 | 200 | 16 | 4 |
| P20 | 800 | 400 | 4 | 1 |

TABLE P48

MIC$_{50}$ and MIC$_{90}$ of the five antibiotics after combined use

| Combined drug | Antibiotic (µg/ml) | |
|---|---|---|
| | MIC$_{50}$ after combined use | MIC$_{90}$ after combined use |
| EA + CAZ | 16 | 128 |
| EA + CFP | 4 | 128 |
| EA + AMK | 0.12 | 4 |
| EA + IMP | 4 | 16 |
| EA + LVX | 1 | 4 |

With the single use of the *Pithecellobium clypearia* Benth 95% ethanol extract to the MDRPA, the MIC$_{50}$ is 800 µg/ml, the MIC$_{90}$ is 800 µg/ml, the MBC$_{50}$ is 1600 µg/ml, and the MBC$_{90}$ is 1600 µg/ml.

For the 20 MDRPAs, it is indicated by FIC≤2 with the combined use of the *Pithecellobium clypearia* Benth 95% ethanol extract and the CAZ that the two drugs have no antagonistic effect, wherein 25% with FIC≤0.5 have the synergistic effect.

For the 20 MDRPAs, when the concentration of the *Pithecellobium clypearia* Benth 95% ethanol extract is smaller than or equal to the single-use MIC, the MIC$_{50}$ of the CAZ is reduced from single-use 32 µg/ml to 16 µg/ml and is reduced by 50%; and the MIC$_{90}$ is reduced from 256 µg/ml to 128 µg/ml and is reduced by 50%.

It is indicated by FIC≤2 with the combined use of the *Pithecellobium clypearia* Benth 95% ethanol extract and the CFP to the 20 MDRPAs that the two drugs have no antagonistic effect, wherein 40% with FIC≤0.5 have the synergistic effect. For the 20 MDRPAs, when the concentration of the *Pithecellobium clypearia* Benth 95% ethanol extract is smaller than or equal to the single-use MIC, the MIC$_{50}$ of the CFP is reduced from single-use 64 µg/ml to 4 µg/ml and is reduced by 93.75%; and the MIC$_{90}$ is reduced from 512 µg/ml to 128 µg/ml and is reduced by 75%.

It is indicated by FIC≤2 with the combined use of the *Pithecellobium clypearia* Benth 95% ethanol extract and the AMK that the two drugs have no antagonistic effect, wherein 40% with FIC≤0.5 have the synergistic effect. For the 20 MDRPAs, when the concentration of the *Pithecellobium clypearia* Benth 95% ethanol extract is smaller than or equal to the single-use MIC, the MIC$_{50}$ of the AMK is reduced from single-use 1 µg/ml to 0.12 µg/ml and is reduced by 87.5%; and the MIC$_{90}$ is reduced from 32 µg/ml to 4 µg/ml and is reduced by 87.5%.

It is indicated by FIC≤2 with the combined use of the *Pithecellobium clypearia* Benth 95% ethanol extract and the IMP that the two drugs have no antagonistic effect, wherein 40% with FIC≤0.5 have the synergistic effect. For the 20 MDRPAs, when the concentration of the *Pithecellobium clypearia* Benth 95% ethanol extract is smaller than or equal to the single-use MIC, the MIC$_{50}$ of the IMP is reduced from single-use 32 µg/ml to 4 µg/ml and is reduced by 75%; and the MIC$_{90}$ is reduced from 64 µg/ml to 16 µg/ml and is reduced by 75%.

It is indicated by FIC≤2 with the combined use of the *Pithecellobium clypearia* Benth 95% ethanol extract and the LVX to the 20 MDRPAs that the two drugs have no antagonistic effect, wherein 10% with FIC≤0.5 show that the two drugs have a certain synergistic effect. For the 20 MDRPA, when the concentration of the *Pithecellobium clypearia* Benth 95% ethanol extract is smaller than or equal to the single-use MIC, the MIC$_{50}$ of the LVX is reduced from single-use 4 µg/ml to 1 µg/ml and is reduced by 75%; and the MIC$_{90}$ is reduced from 32 µg/ml to 4 µg/ml and is reduced by 87.5%.

III. Inhibitory and bactericidal tests of the ESBL-producing *escherichia coli* (hereinafter referred to as an ESBL-producing ECO) resistance of the EA and test of the sensibilization effect by respectively using with the AMK or the SXT Embodiment 3

1. Test method: the MDRPA (serial No.: E1-E20) strains are tested and are evaluated with reference to the method in the first embodiment.

2. Test Results 2.1. In-vitro inhibitory test results of the *Pithecellobium clypearia* Benth water extract and the two antibiotics (the AMK and the SXT) to the ESBL-producing ECOs are shown in table E1.

In-vitro bactericidal test results of the *Pithecellobium clypearia* Benth water extract to the ESBL-producing ECOs are shown in table E2.

The statistic analysis on in-vitro inhibitory and bactericidal MIC$_{50}$ and MIC$_{90}$ of the *Pithecellobium clypearia* Benth water extract and the two antibiotics to the ESBL-producing ECOs is shown in table E3.

The statistic analysis on bactericidal MBC$_{50}$ and MBC$_{90}$ of the EA to the ESBL-producing ECOs is shown in table E4.

FIC values of a combined drug sensitive test of the *Pithecellobium clypearia* Benth water extract and the two antibiotics and distribution statistical results of the FIC values are shown in table E5 and table E6.

The sensibilization effects of the *Pithecellobium clypearia* Benth water extract to the two antibiotics and the MIC$_{50}$ and MIC$_{90}$ after combined use are shown in tables E7-E9.

TABLE E1

| Strain No. | MIC (µg/ml) | | |
|---|---|---|---|
| | EA | AMK | SXT |
| E1 | 1600 | 4 | 2432/128 |
| E2 | 1600 | 16 | 2432/128 |
| E3 | 1600 | 512 | 2432/128 |
| E4 | 1600 | 4 | 76/4 |
| E5 | 1600 | 16 | 2432/128 |
| E6 | 1600 | 4 | 2432/128 |
| E7 | 1600 | 32 | 2432/128 |
| E8 | 1600 | 32 | 2432/128 |
| E9 | 1600 | 64 | 2432/128 |
| E10 | 1600 | 8 | 2432/128 |
| E11 | 1600 | 32 | 76/4 |
| E12 | 1600 | 32 | 2432/128 |
| E13 | 1600 | 4 | 2432/128 |
| E14 | 1600 | 8 | 2432/128 |
| E15 | 1600 | 8 | 2432/128 |
| E16 | 1600 | 16 | 2432/128 |
| E17 | 1600 | 8 | 2432/128 |
| E18 | 1600 | 128 | 2432/128 |
| E19 | 1600 | 64 | 152/8 |
| E20 | 1600 | 16 | 76/4 |
| ATCC25922 | 800 | 4 | 9.5/0.5 |

TABLE E2

| Strain No. | MBC(μg/ml) |
|---|---|
| E1 | 3200 |
| E2 | 3200 |
| E3 | 3200 |
| E4 | 3200 |
| E5 | 3200 |
| E6 | 3200 |
| E7 | 3200 |
| E8 | 3200 |
| E9 | 3200 |
| E10 | 3200 |
| E11 | 3200 |
| E12 | 3200 |
| E13 | 3200 |
| E14 | 3200 |
| E15 | 3200 |
| E16 | 3200 |
| E17 | 3200 |
| E18 | 3200 |
| E19 | 3200 |
| E20 | 3200 |

TABLE E3

| Drug | MIC (μg/ml) Range | $MIC_{50}$ | $MIC_{90}$ |
|---|---|---|---|
| EA | 1600 | 1600 | 1600 |
| AMK | 4-512 | 16 | 64 |
| SXT | 76/4-2432/128 | 2432/128 | 2432/128 |

TABLE E4

| Drug | MBC (μg/ml) Range | $MBC_{50}$ | $MBC_{90}$ |
|---|---|---|---|
| EA | 3200 | 3200 | 3200 |

TABLE E5

| Strain No. | FIC EA + AMK | EA + SXT |
|---|---|---|
| E1 | 0.75 | 0.507813 |
| E2 | 0.375 | 1.003906 |
| E3 | 0.28125 | 0.507813 |
| E4 | 0.75 | 0.75 |
| E5 | 0.625 | 0.507813 |
| E6 | 1 | 0.515625 |
| E7 | 0.375 | 0.507813 |
| E8 | 0.5 | 0.507813 |
| E9 | 0.375 | 0.500061 |
| E10 | 0.75 | 0.507813 |
| E11 | 0.5 | 0.375 |
| E12 | 0.75 | 0.125485 |
| E13 | 1.25 | 0.507813 |
| E14 | 0.75 | 0.507813 |
| E15 | 0.75 | 0.500058 |
| E16 | 0.5 | 0.125485 |
| E17 | 0.5 | 0.507813 |
| E18 | 0.625 | 0.250977 |
| E19 | 0.375 | 0.375 |
| E20 | 0.5 | 0.75 |

TABLE E6

| FIC Range | EA + AMK | EA + SXT |
|---|---|---|
| FIC ≤ 0.5 | 50% | 25% |
| 0.5 < FIC ≤ 1 | 45% | 70% |
| 1 < FIC ≤ 2 | 5% | 5% |
| FIC > 2 | — | — |

TABLE E7

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| E1 | 1600 | 400 | 4 | 2 |
| E2 | 1600 | 200 | 16 | 4 |
| E3 | 1600 | 400 | 512 | 16 |
| E4 | 1600 | 400 | 4 | 2 |
| E5 | 1600 | 200 | 16 | 8 |
| E6 | 1600 | 800 | 4 | 2 |
| E7 | 1600 | 200 | 32 | 8 |
| E8 | 1600 | 400 | 32 | 8 |
| E9 | 1600 | 400 | 64 | 8 |
| E10 | 1600 | 400 | 8 | 4 |
| E11 | 1600 | 400 | 32 | 8 |
| E12 | 1600 | 400 | 32 | 16 |
| E13 | 1600 | 800 | 4 | 2 |
| E14 | 1600 | 400 | 8 | 4 |
| E15 | 1600 | 400 | 8 | 4 |
| E16 | 1600 | 400 | 16 | 4 |
| E17 | 1600 | 400 | 8 | 2 |
| E18 | 1600 | 800 | 128 | 16 |
| E19 | 1600 | 200 | 64 | 16 |
| E20 | 1600 | 400 | 16 | 4 |

TABLE E8

| Strain No. | EA single-use MIC (μg/ml) | EA combined-use MIC (μg/ml) | SXT single-use MIC (μg/ml) | SXT combined-use MIC (μg/ml) |
|---|---|---|---|---|
| E1 | 1600 | 800 | 2432/128 | 19/1 |
| E2 | 1600 | 1600 | 2432/128 | 9.5/0.5 |
| E3 | 1600 | 800 | 2432/128 | 19/1 |
| E4 | 1600 | 800 | 76/4 | 19/1 |
| E5 | 1600 | 800 | 2432/128 | 19/1 |
| E6 | 1600 | 800 | 2432/128 | 38/2 |
| E7 | 1600 | 800 | 2432/128 | 19/1 |
| E8 | 1600 | 800 | 2432/128 | 19/1 |
| E9 | 1600 | 800 | 2432/128 | 0.148438/0.078125 |
| E10 | 1600 | 800 | 2432/128 | 19/1 |
| E11 | 1600 | 200 | 76/4 | 19/1 |
| E12 | 1600 | 200 | 2432/128 | 1.1875/0.0625 |
| E13 | 1600 | 800 | 2432/128 | 19/1 |
| E14 | 1600 | 800 | 2432/128 | 19/1 |
| E15 | 1600 | 800 | 2432/128 | 0.148438/0.078125 |
| E16 | 1600 | 200 | 2432/128 | 1.1875/0.0625 |
| E17 | 1600 | 800 | 2432/128 | 19/1 |
| E18 | 1600 | 400 | 2432/128 | 2.375/0.125 |
| E19 | 1600 | 400 | 152/8 | 19/1 |
| E20 | 1600 | 800 | 76/4 | 19/1 |

TABLE E9

| Combined drug | Antibiotic (μg/ml) $MIC_{50}$ after combined use | $MIC_{90}$ after combined use |
|---|---|---|
| EA + AMK | 4 | 16 |
| EA + SXT | 19/1 | 19/1 |

The test results shows that, with the single use of the *Pithecellobium clypearia* Benth water extract to the ESBL-producing ECOs, the $MIC_{50}$ is 1600 μg/ml, the $MIC_{90}$ is 1600 μg/ml, the $MBC_{50}$ is 3200 μg/ml, and the $MBC_{90}$ is 3200 μg/ml.

For the 20 ESBL-producing ECOs, it is indicated by FIC≤2 with the combined use of the *Pithecellobium clypearia* Benth water extract and the AMK that the two drugs have no antagonistic effect, wherein 50% with FIC≤0.5 have the synergistic effect. When the *Pithecellobium clypearia* Benth water extract is smaller than or equal to ½ MIC, the $MIC_{50}$ of the AMK is reduced from single-use 16 μg/ml to 4 μg/ml and is reduced by 75%; and the $MIC_{90}$ is reduced from 64 μg/ml to 16 μg/ml and is reduced by 75%.

It is indicated by FIC≤2 with the combined use of the *Pithecellobium clypearia* Benth water extract and the SXT to the 20 ESBL-producing ECOs that the two drugs have no antagonistic effect, wherein 25% with FIC≤0.5 have the synergistic effect. When the *Pithecellobium clypearia* Benth water extract is smaller than or equal to the single-use MIC, the $MIC_{50}$ and the $MIC_{90}$ of the SXT are respectively reduced from single-use 2432/128 μg/ml to 19/1 μg/ml, and are reduced by 99.3%.

2.2. In-vitro inhibitory test results of the *Pithecellobium clypearia* Benth 10% ethanol extract and the two antibiotics (the AMK and the SXT) to the ESBL-producing ECOs are shown in table E10.

In-vitro bactericidal test results of the *Pithecellobium clypearia* Benth 10% ethanol extract to the ESBL-producing ECOs are shown in table E11.

The statistic analysis on in-vitro inhibitory and bactericidal $MIC_{50}$ and $MIC_{90}$ of the *Pithecellobium clypearia* Benth 10% ethanol extract and the two antibiotics to the ESBL-producing ECOs is shown in table E12.

The statistic analysis on bactericidal $MBC_{50}$ and $MBC_{90}$ of the *Pithecellobium clypearia* Benth 10% ethanol extract to the ESBL-producing ECOs is shown in table E13.

FIC values of a combined drug sensitive test of the *Pithecellobium clypearia* Benth 10% ethanol extract and the two antibiotics and distribution statistical results of the FIC values are shown in table E14 and table E15.

The sensibilization effects of the *Pithecellobium clypearia* Benth 10% ethanol extract to the two antibiotics and the $MIC_{50}$ and $MIC_{90}$ after combined use are shown in tables E16-E18.

TABLE E10

| Strain No. | MIC (μg/ml) | | |
|---|---|---|---|
| | EA | AMK | SXT |
| E1 | 1600 | 4 | 2432/128 |
| E2 | 1600 | 16 | 2432/128 |
| E3 | 1600 | 512 | 2432/128 |
| E4 | 1600 | 4 | 76/4 |
| E5 | 1600 | 16 | 2432/128 |
| E6 | 1600 | 4 | 2432/128 |
| E7 | 1600 | 32 | 2432/128 |
| E8 | 1600 | 32 | 2432/128 |
| E9 | 1600 | 64 | 2432/128 |
| E10 | 1600 | 8 | 2432/128 |
| E11 | 1600 | 32 | 76/4 |
| E12 | 1600 | 32 | 2432/128 |
| E13 | 1600 | 4 | 2432/128 |
| E14 | 1600 | 8 | 2432/128 |
| E15 | 1600 | 8 | 2432/128 |
| E16 | 1600 | 16 | 2432/128 |
| E17 | 1600 | 8 | 2432/128 |
| E18 | 1600 | 128 | 2432/128 |
| E19 | 1600 | 64 | 152/8 |
| E20 | 1600 | 16 | 76/4 |
| ATCC25922 | 800 | 4 | 9.5/0.5 |

TABLE E11

| Strain No. | MBC(μg/ml) |
|---|---|
| E1 | 3200 |
| E2 | 3200 |
| E3 | 3200 |
| E4 | 3200 |
| E5 | 3200 |
| E6 | 3200 |
| E7 | 3200 |
| E8 | 3200 |
| E9 | 3200 |
| E10 | 3200 |
| E11 | 3200 |
| E12 | 3200 |
| E13 | 3200 |
| E14 | 3200 |
| E15 | 3200 |
| E16 | 3200 |
| E17 | 3200 |
| E18 | 3200 |
| E19 | 3200 |
| E20 | 3200 |

TABLE E12

| Drug | MIC (μg/ml) | | |
|---|---|---|---|
| | Range | $MIC_{50}$ | $MIC_{90}$ |
| EA | 1600 | 1600 | 1600 |
| AMK | 4-512 | 16 | 64 |
| SXT | 76/4-2432/128 | 2432/128 | 2432/128 |

TABLE E13

| Drug | MBC (μg/ml) | | |
|---|---|---|---|
| | Range | $MBC_{50}$ | $MBC_{90}$ |
| EA | 3200 | 3200 | 3200 |

TABLE E14

| Strain No. | FIC | |
|---|---|---|
| | EA + AMK | EA + SXT |
| E1 | 1 | 0.507813 |
| E2 | 0.75 | 0.507813 |
| E3 | 0.265625 | 0.507813 |
| E4 | 0.5 | 0.75 |
| E5 | 0.5 | 0.507813 |
| E6 | 1 | 0.507813 |
| E7 | 0.5 | 0.507813 |
| E8 | 0.75 | 0.507813 |
| E9 | 0.5 | 0.500061 |
| E10 | 0.75 | 0.507813 |
| E11 | 0.5 | 0.5 |
| E12 | 0.75 | 0.250975 |
| E13 | 1 | 0.507813 |
| E14 | 1 | 0.507813 |
| E15 | 0.75 | 0.500058 |
| E16 | 0.5 | 0.125485 |
| E17 | 0.75 | 0.507813 |
| E18 | 0.5 | 1.000977 |
| E19 | 0.375 | 0.375 |
| E20 | 0.5 | 0.75 |

TABLE E15

| FIC Range | EA + AMK | EA + SXT |
|---|---|---|
| FIC ≤ 0.5 | 50% | 20% |
| 0.5 < FIC ≤ 1 | 50% | 75% |
| 1 < FIC ≤ 2 | — | 5% |
| FIC > 2 | — | — |

TABLE E16

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| E1 | 1600 | 800 | 4 | 2 |
| E2 | 1600 | 800 | 16 | 4 |
| E3 | 1600 | 400 | 512 | 8 |
| E4 | 1600 | 400 | 4 | 1 |
| E5 | 1600 | 400 | 16 | 4 |
| E6 | 1600 | 800 | 4 | 2 |
| E7 | 1600 | 400 | 32 | 8 |
| E8 | 1600 | 800 | 32 | 8 |
| E9 | 1600 | 400 | 64 | 16 |
| E10 | 1600 | 400 | 8 | 4 |
| E11 | 1600 | 400 | 32 | 8 |
| E12 | 1600 | 400 | 32 | 16 |
| E13 | 1600 | 800 | 4 | 2 |
| E14 | 1600 | 800 | 8 | 4 |
| E15 | 1600 | 400 | 8 | 4 |
| E16 | 1600 | 400 | 16 | 4 |
| E17 | 1600 | 800 | 8 | 2 |
| E18 | 1600 | 400 | 128 | 32 |
| E19 | 1600 | 400 | 64 | 8 |
| E20 | 1600 | 400 | 16 | 4 |

TABLE E17

| Strain No. | EA single-use MIC (μg/ml) | EA combined-use MIC (μg/ml) | SXT single-use MIC (μg/ml) | SXT combined-use MIC (μg/ml) |
|---|---|---|---|---|
| E1 | 1600 | 800 | 2432/128 | 19/1 |
| E2 | 1600 | 800 | 2432/128 | 19/1 |
| E3 | 1600 | 800 | 2432/128 | 19/1 |
| E4 | 1600 | 800 | 76/4 | 19/1 |
| E5 | 1600 | 800 | 2432/128 | 19/1 |
| E6 | 1600 | 800 | 2432/128 | 19/1 |
| E7 | 1600 | 800 | 2432/128 | 19/1 |
| E8 | 1600 | 800 | 2432/128 | 19/1 |
| E9 | 1600 | 800 | 2432/128 | 0.148438/0.078125 |
| E10 | 1600 | 800 | 2432/128 | 19/1 |
| E11 | 1600 | 400 | 76/4 | 19/1 |
| E12 | 1600 | 400 | 2432/128 | 2.375/0.125 |
| E13 | 1600 | 800 | 2432/128 | 19/1 |
| E14 | 1600 | 800 | 2432/128 | 19/1 |
| E15 | 1600 | 800 | 2432/128 | 0.148438/0.078125 |
| E16 | 1600 | 200 | 2432/128 | 1.1875/0.0625 |
| E17 | 1600 | 800 | 2432/128 | 19/1 |
| E18 | 1600 | 1600 | 2432/128 | 2.375/0.125 |
| E19 | 1600 | 400 | 152/8 | 19/1 |
| E20 | 1600 | 800 | 76/4 | 19/1 |

TABLE E18

| Combined drug | Antibiotic (μg/ml) $MIC_{50}$ after combined use | Antibiotic (μg/ml) $MIC_{90}$ after combined use |
|---|---|---|
| EA + AMK | 4 | 16 |
| EA + SXT | 19/1 | 19/1 |

The test results shows that, with the single use of the *Pithecellobium clypearia* Benth 10% ethanol extract to the ESBL-producing ECOs, the $MIC_{50}$ is 1600 μg/ml, the $MIC_{90}$ is 1600 μg/ml, the $MBC_{50}$ is 3200 μg/ml, and the $MBC_{90}$ is 3200 μg/ml.

For the 20 ESBL-producing ECOs, it is indicated by FIC≤2 with the combined use of the *Pithecellobium clypearia* Benth 10% ethanol extract and the AMK that the two drugs have no antagonistic effect, wherein 50% with FIC≤0.5 have the synergistic effect. When the *Pithecellobium clypearia* Benth 10% ethanol extract is smaller than or equal to ½ MIC, the $MIC_{50}$ of the AMK is reduced from single-use 16 μg/ml to 4 μg/ml and is reduced by 75%; and the $MIC_{90}$ is reduced from 64 μg/ml to 16 μg/ml and is reduced by 75%.

It is indicated by FIC≤2 with the combined use of the *Pithecellobium clypearia* Benth 10% ethanol extract and the SXT to the 20 ESBL-producing ECOs that the two drugs have no antagonistic effect, wherein 20% with FIC≤0.5 have the synergistic effect. When the *Pithecellobium clypearia* Benth 10% ethanol extract is smaller than or equal to the single-use MIC, the $MIC_{50}$ and the $MIC_{90}$ of the SXT are respectively reduced from single-use 2432/128 μg/ml to 19/1 μg/ml, and are reduced by 99.3%.

2.3. In-vitro inhibitory test results of the *Pithecellobium clypearia* Benth 60% ethanol extract and the two antibiotics (the AMK and the SXT) to the ESBL-producing ECOs are shown in table E19.

In-vitro bactericidal test results of the *Pithecellobium clypearia* Benth 60% ethanol extract to the ESBL-producing ECOs are shown in table E20.

The statistic analysis on in-vitro inhibitory and bactericidal $MIC_{50}$ and $MIC_{90}$ of the *Pithecellobium clypearia* Benth 60% ethanol extract and the two antibiotics to the ESBL-producing ECOs is shown in table E21.

The statistic analysis on bactericidal $MBC_{50}$ and $MBC_{90}$ of the *Pithecellobium clypearia* Benth 60% ethanol extract to the ESBL-producing ECOs is shown in table E22.

FIC values of a combined drug sensitive test of the *Pithecellobium clypearia* Benth 60% ethanol extract and the two antibiotics and distribution statistical results of the FIC values are shown in table E23 and table E24.

The sensibilization effects of the *Pithecellobium clypearia* Benth 60% ethanol extract to the two antibiotics and the $MIC_{50}$ and $MIC_{90}$ after combined use are shown in tables E25-E27.

TABLE E19

| Strain No. | MIC (μg/ml) EA | MIC (μg/ml) AMK | MIC (μg/ml) SXT |
|---|---|---|---|
| E1 | 800 | 4 | 2432/128 |
| E2 | 800 | 16 | 2432/128 |
| E3 | 800 | 512 | 2432/128 |
| E4 | 800 | 4 | 76/4 |
| E5 | 800 | 16 | 2432/128 |
| E6 | 1600 | 4 | 2432/128 |
| E7 | 800 | 32 | 2432/128 |
| E8 | 800 | 32 | 2432/128 |
| E9 | 800 | 64 | 2432/128 |
| E10 | 800 | 8 | 2432/128 |
| E11 | 800 | 32 | 76/4 |
| E12 | 800 | 32 | 2432/128 |
| E13 | 400 | 4 | 2432/128 |
| E14 | 800 | 8 | 2432/128 |
| E15 | 800 | 8 | 2432/128 |
| E16 | 800 | 16 | 2432/128 |
| E17 | 800 | 8 | 2432/128 |
| E18 | 800 | 128 | 2432/128 |
| E19 | 800 | 64 | 152/8 |

TABLE E19-continued

| Strain No. | MIC (μg/ml) | | |
|---|---|---|---|
| | EA | AMK | SXT |
| E20 | 800 | 16 | 76/4 |
| ATCC25922 | 800 | 4 | 9.5/0.5 |

TABLE E20

| Strain No. | MBC (μg/ml) |
|---|---|
| E1 | 1600 |
| E2 | 1600 |
| E3 | 1600 |
| E4 | 1600 |
| E5 | 1600 |
| E6 | >1600 |
| E7 | 1600 |
| E8 | 1600 |
| E9 | 1600 |
| E10 | 1600 |
| E11 | 1600 |
| E12 | 1600 |
| E13 | >1600 |
| E14 | 1600 |
| E15 | 1600 |
| E16 | 1600 |
| E17 | 1600 |
| E18 | 1600 |
| E19 | 1600 |
| E20 | 1600 |

TABLE E21

| Drug | MIC (μg/ml) | | |
|---|---|---|---|
| | Range | $MIC_{50}$ | $MIC_{90}$ |
| EA | 400-1600 | 800 | 800 |
| AMK | 4-512 | 16 | 64 |
| SXT | 76/4-2432/128 | 2432/128 | 2432/128 |

TABLE E22

| Drug | MBC (μg/ml) | | |
|---|---|---|---|
| | Range | $MBC_{50}$ | $MBC_{90}$ |
| EA | ≥1600 | 1600 | 1600 |

TABLE E23

| Strain no. | FIC | |
|---|---|---|
| | EA + AMK | EA + SXT |
| E1 | 0.5625 | 1.0078 |
| E2 | 0.25 | 1.0078 |
| E3 | 0.2656 | 1.0001 |
| E4 | 0.5625 | 0.75 |
| E5 | 0.5625 | 0.5078 |
| E6 | 0.375 | 0.2656 |
| E7 | 0.125 | 0.5078 |
| E8 | 0.1875 | 0.5078 |
| E9 | 0.3125 | 1.0001 |
| E10 | 0.5625 | 0.5078 |
| E11 | 0.1875 | 0.0703 |
| E12 | 0.1875 | 0.0630 |
| E13 | 1.125 | 1.0039 |
| E14 | 0.5625 | 0.5156 |
| E15 | 0.3125 | 1.0001 |
| E16 | 0.1875 | 0.0630 |
| E17 | 0.3125 | 0.5078 |
| E18 | 0.375 | 0.0635 |
| E19 | 0.25 | 0.625 |
| E20 | 0.3125 | 0.375 |

TABLE E24

| FIC Range | EA + AMK | EA + SXT |
|---|---|---|
| FIC ≤ 0.5 | 70% | 30% |
| 0.5 < FIC ≤ 1 | 25% | 40% |
| 1 < FIC ≤ 2 | 5% | 30% |
| FIC > 2 | — | — |

TABLE E25

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| E1 | 800 | 50 | 4 | 2 |
| E2 | 800 | 100 | 16 | 2 |
| E3 | 800 | 200 | 512 | 8 |
| E4 | 800 | 50 | 4 | 2 |
| E5 | 800 | 50 | 16 | 8 |
| E6 | 1600 | 400 | 4 | 0.5 |
| E7 | 800 | 50 | 32 | 2 |
| E8 | 800 | 50 | 32 | 4 |
| E9 | 800 | 200 | 64 | 4 |
| E10 | 800 | 50 | 8 | 4 |
| E11 | 800 | 50 | 32 | 4 |
| E12 | 800 | 50 | 32 | 4 |
| E13 | 400 | 50 | 4 | 4 |
| E14 | 800 | 50 | 8 | 4 |
| E15 | 800 | 50 | 8 | 2 |
| E16 | 800 | 50 | 16 | 2 |
| E17 | 800 | 50 | 8 | 2 |
| E18 | 800 | 100 | 128 | 32 |
| E19 | 800 | 100 | 64 | 8 |
| E20 | 800 | 50 | 16 | 4 |

TABLE E26

| Strain No. | EA single-use MIC (μg/ml) | EA combined-use MIC (μg/ml) | SXT single-use MIC (μg/ml) | SXT combined-use MIC (μg/ml) |
|---|---|---|---|---|
| E1 | 800 | 800 | 2432/128 | 19/1 |
| E2 | 800 | 800 | 2432/128 | 9.5/0.5 |
| E3 | 800 | 800 | 2432/128 | 0.148438/0.078125 |
| E4 | 800 | 400 | 76/4 | 19/1 |
| E5 | 800 | 400 | 2432/128 | 19/1 |
| E6 | 1600 | 400 | 2432/128 | 38/2 |
| E7 | 800 | 400 | 2432/128 | 19/1 |
| E8 | 800 | 400 | 2432/128 | 19/1 |
| E9 | 800 | 800 | 2432/128 | 0.148438/0.078125 |
| E10 | 800 | 400 | 2432/128 | 19/1 |
| E11 | 800 | 50 | 76/4 | 19/1 |
| E12 | 800 | 50 | 2432/128 | 1.1875/0.0625 |
| E13 | 400 | 400 | 2432/128 | 9.5/0.5 |
| E14 | 800 | 400 | 2432/128 | 38/2 |
| E15 | 800 | 800 | 2432/128 | 0.148438/0.078125 |
| E16 | 800 | 50 | 2432/128 | 1.1875/0.0625 |
| E17 | 800 | 400 | 2432/128 | 19/1 |
| E18 | 800 | 50 | 2432/128 | 2.375/0.125 |
| E19 | 800 | 400 | 152/8 | 19/1 |
| E20 | 800 | 100 | 76/4 | 19/1 |

TABLE E27

| Combined drug | MIC$_{50}$ after combined use | MIC$_{90}$ after combined use |
|---|---|---|
| EA + AMK | 4 | 8 |
| EA + SXT | 19/1 | 19/1 |

The test results shows that, with the single use of the *Pithecellobium clypearia* Benth 60% ethanol extract to the ESBL-producing ECOs, the MIC$_{50}$ is 800 μg/ml, the MIC$_{90}$ is 800 μg/ml, the MBC$_{50}$ is 1600 μg/ml, and the MBC$_{90}$ is 1600 μg/ml.

For the 20 ESBL-producing ECOs, it is indicated by FIC≤2 with the combined use of the *Pithecellobium clypearia* Benth 60% ethanol extract and the AMK that the two drugs have no antagonistic effect, wherein 70% with FIC≤0.5 have the synergistic effect. When the *Pithecellobium clypearia* Benth 60% ethanol extract is smaller than or equal to ¼ MIC, the MIC$_{50}$ of the AMK is reduced from single-use 16 μg/ml to 4 μg/ml and is reduced by 75%; and the MIC$_{90}$ is reduced from 64 μg/ml to 8 μg/ml.

It is indicated by FIC≤2 with the combined use of the *Pithecellobium clypearia* Benth 60% ethanol extract and the SXT to the 20 ESBL-producing ECOs that the two drugs have no antagonistic effect, wherein 30% with FIC≤0.5 have the synergistic effect. When the *Pithecellobium clypearia* Benth 60% ethanol extract is smaller than or equal to the single-use MIC, the MIC$_{50}$ and the MIC$_{90}$ of the SXT are respectively reduced from single-use 2432/128 μg/ml to 19/1 μg/ml, and are reduced by 99.3%.

2.4. In-vitro inhibitory test results of the *Pithecellobium clypearia* Benth 95% ethanol extract and the two antibiotics (the AMK and the SXT) to the ESBL-producing ECOs are shown in table E28.

In-vitro bactericidal test results of the *Pithecellobium clypearia* Benth 95% ethanol extract to the ESBL-producing ECOs are shown in table E29.

The statistic analysis on in-vitro inhibitory and bactericidal MIC$_{50}$ and MIC$_{90}$ of the *Pithecellobium clypearia* Benth 95% ethanol extract and the two antibiotics to the ESBL-producing ECOs is shown in table E30.

The statistic analysis on bactericidal MBC$_{50}$ and MBC$_{90}$ of the *Pithecellobium clypearia* Benth 95% ethanol extract to the ESBL-producing ECOs is shown in table E31.

FIC values of a combined drug sensitive test of the *Pithecellobium clypearia* Benth 95% ethanol extract and the two antibiotics and distribution statistical results of the FIC values are shown in table E32 and table E33.

The sensibilization effects of the *Pithecellobium clypearia* Benth 95% ethanol extract to the two antibiotics and the MIC$_{50}$ and MIC$_{90}$ after combined use are shown in tables E34-E36.

TABLE E28

| Strain No. | MIC (μg/ml) | | |
|---|---|---|---|
| | EA | AMK | SXT |
| E1 | 1600 | 4 | 2432/128 |
| E2 | 1600 | 16 | 2432/128 |
| E3 | 1600 | 512 | 2432/128 |
| E4 | 1600 | 4 | 76/4 |
| E5 | 1600 | 16 | 2432/128 |
| E6 | 1600 | 4 | 2432/128 |
| E7 | 1600 | 32 | 2432/128 |
| E8 | 1600 | 32 | 2432/128 |
| E9 | 1600 | 64 | 2432/128 |
| E10 | 1600 | 8 | 2432/128 |
| E11 | 1600 | 32 | 76/4 |
| E12 | 1600 | 32 | 2432/128 |
| E13 | 1600 | 4 | 2432/128 |
| E14 | 1600 | 8 | 2432/128 |
| E15 | 1600 | 8 | 2432/128 |
| E16 | 1600 | 16 | 2432/128 |
| E17 | 1600 | 8 | 2432/128 |
| E18 | 1600 | 128 | 2432/128 |
| E19 | 1600 | 64 | 152/8 |
| E20 | 1600 | 16 | 76/4 |
| ATCC25922 | 800 | 4 | 9.5/0.5 |

TABLE E29

| Strain No. | MBC(μg/ml) |
|---|---|
| E1 | 3200 |
| E2 | 3200 |
| E3 | 3200 |
| E4 | 3200 |
| E5 | 3200 |
| E6 | 3200 |
| E7 | 3200 |
| E8 | 3200 |
| E9 | 3200 |
| E10 | 3200 |
| E11 | 3200 |
| E12 | 3200 |
| E13 | 3200 |
| E14 | 3200 |
| E15 | 3200 |
| E16 | 3200 |
| E17 | 3200 |
| E18 | 3200 |
| E19 | 3200 |
| E20 | 3200 |

TABLE E30

| Drug | Range | MIC (μg/ml) MIC$_{50}$ | MIC$_{90}$ |
|---|---|---|---|
| EA | 1600 | 1600 | 1600 |
| AMK | 4-512 | 16 | 64 |
| SXT | 76/4-2432/128 | 2432/128 | 2432/128 |

TABLE E31

| Drug | Range | MBC (μg/ml) MBC$_{50}$ | MBC$_{90}$ |
|---|---|---|---|
| EA | 3200 | 3200 | 3200 |

TABLE E32

| Strain No. | FIC EA + AMK | EA + SXT |
|---|---|---|
| E1 | 1 | 0.507813 |
| E2 | 0.5 | 0.507813 |
| E3 | 0.53125 | 0.507813 |
| E4 | 0.5 | 0.75 |

TABLE E32-continued

| | FIC | |
|---|---|---|
| Strain No. | EA + AMK | EA + SXT |
| E5 | 0.5 | 0.507813 |
| E6 | 0.75 | 0.507813 |
| E7 | 0.75 | 0.503906 |
| E8 | 0.75 | 0.507813 |
| E9 | 0.75 | 0.503906 |
| E10 | 0.75 | 0.507813 |
| E11 | 0.75 | 0.75 |
| E12 | 0.5 | 1.000975 |
| E13 | 0.75 | 0.507813 |
| E14 | 0.75 | 0.507813 |
| E15 | 0.75 | 0.500058 |
| E16 | 0.5 | 0.132813 |
| E17 | 0.75 | 0.507813 |
| E18 | 0.5 | 1.000977 |
| E19 | 0.375 | 0.625 |
| E20 | 0.5 | 0.75 |

TABLE E33

| FIC Range | EA + AMK | EA + SXT |
|---|---|---|
| FIC ≤ 0.5 | 40% | 5% |
| 0.5 < FIC ≤ 1 | 60% | 85% |
| 1 < FIC ≤ 2 | — | 10% |
| FIC > 2 | — | — |

TABLE E34

| Strain No. | EA single-use MIC (μg/ml) | EA combined-use MIC (μg/ml) | AMK single-use MIC (μg/ml) | AMK combined-use MIC (μg/ml) |
|---|---|---|---|---|
| E1 | 1600 | 800 | 4 | 2 |
| E2 | 1600 | 400 | 16 | 4 |
| E3 | 1600 | 800 | 512 | 16 |
| E4 | 1600 | 400 | 4 | 1 |
| E5 | 1600 | 400 | 16 | 4 |
| E6 | 1600 | 800 | 4 | 1 |
| E7 | 1600 | 800 | 32 | 8 |
| E8 | 1600 | 800 | 32 | 8 |
| E9 | 1600 | 800 | 64 | 16 |
| E10 | 1600 | 400 | 8 | 4 |
| E11 | 1600 | 800 | 32 | 8 |
| E12 | 1600 | 400 | 32 | 8 |
| E13 | 1600 | 400 | 4 | 2 |
| E14 | 1600 | 800 | 8 | 2 |
| E15 | 1600 | 400 | 8 | 4 |
| E16 | 1600 | 400 | 16 | 4 |
| E17 | 1600 | 800 | 8 | 2 |
| E18 | 1600 | 400 | 128 | 32 |
| E19 | 1600 | 400 | 64 | 8 |
| E20 | 1600 | 400 | 16 | 4 |

TABLE E35

| Strain No. | EA single-use MIC (μg/ml) | EA combined-use MIC (μg/ml) | SXT single-use MIC (μg/ml) | SXT combined-use MIC (μg/ml) |
|---|---|---|---|---|
| E1 | 1600 | 800 | 2432/128 | 19/1 |
| E2 | 1600 | 800 | 2432/128 | 19/1 |
| E3 | 1600 | 800 | 2432/128 | 19/1 |
| E4 | 1600 | 800 | 76/4 | 19/1 |
| E5 | 1600 | 800 | 2432/128 | 19/1 |
| E6 | 1600 | 800 | 2432/128 | 19/1 |
| E7 | 1600 | 800 | 2432/128 | 9.5/0.5 |
| E8 | 1600 | 800 | 2432/128 | 19/1 |
| E9 | 1600 | 800 | 2432/128 | 9.5/0.5 |
| E10 | 1600 | 800 | 2432/128 | 19/1 |
| E11 | 1600 | 800 | 76/4 | 19/1 |
| E12 | 1600 | 1600 | 2432/128 | 2.375/0.125 |
| E13 | 1600 | 800 | 2432/128 | 19/1 |
| E14 | 1600 | 800 | 2432/128 | 19/1 |
| E15 | 1600 | 800 | 2432/128 | 0.148438/0.078125 |
| E16 | 1600 | 200 | 2432/128 | 19/1 |
| E17 | 1600 | 800 | 2432/128 | 19/1 |
| E18 | 1600 | 1600 | 2432/128 | 2.375/0.125 |
| E19 | 1600 | 800 | 152/8 | 19/1 |
| E20 | 1600 | 800 | 76/4 | 19/1 |

TABLE E36

| | Antibiotic (μg/ml) | |
|---|---|---|
| Combined drug | $MIC_{50}$ after combined use | $MIC_{90}$ after combined use |
| EA + AMK | 4 | 16 |
| EA + SXT | 19/1 | 19/1 |

The test results shows that, with the single use of the *Pithecellobium clypearia* Benth 95% ethanol extract to the ESBL-producing ECOs, the $MIC_{50}$ is 1600 μg/ml, the $MIC_{90}$ is 1600 μg/ml, the $MBC_{50}$ is 3200 μg/ml, and the $MBC_{90}$ is 3200 μg/ml.

For the 20 ESBL-producing ECOs, it is indicated by FIC≤2 with the combined use of the *Pithecellobium clypearia* Benth 95% ethanol extract and the AMK that the two drugs have no antagonistic effect, wherein 50% with FIC≤0.5 have the synergistic effect. When the *Pithecellobium clypearia* Benth 95% ethanol extract is smaller than or equal to ½ MIC, the $MIC_{50}$ of the AMK is reduced from single-use 16 μg/ml to 4 μg/ml and is reduced by 75%; and the $MIC_{90}$ is reduced from 64 μg/ml to 16 μg/ml and is reduced by 75%.

It is indicated by FIC≤2 with the combined use of the *Pithecellobium clypearia* Benth 95% ethanol extract and the SXT to the 20 ESBL-producing ECOs that the two drugs have no antagonistic effect, wherein 20% with FIC≤0.5 have the synergistic effect. When the *Pithecellobium clypearia* Benth 95% ethanol extract is smaller than or equal to the single-use MIC, the $MIC_{50}$ and the $MIC_{90}$ of the SXT are respectively reduced from single-use 2432/128 μg/ml to 19/1 μg/ml, and are reduced by 99.3%.

IV. Inhibitory and bactericidal tests of ESBL-producing *klebsiella pneumoniae* (hereinafter referred to as an ESBL-producing KPN) resistance of the EA Embodiment 4

1. Test method: the ESBL-producing KPN (serial No.: K1-K20) strains are tested and are evaluated with reference to the inhibitory and bactericidal test method in the first embodiment.

2. Test Results

In-vitro inhibitory and bactericidal test results of the *Pithecellobium clypearia* Benth water extract to the ESBL-producing KPNs are shown in table K1.

The statistic analysis on in-vitro inhibitory and bactericidal $MIC_{50}$, $MIC_{90}$, $MBC_{50}$ and $MBC_{90}$ of the *Pithecellobium clypearia* Benth water extract to the ESBL-producing KPNs is shown in table K2 and table K3.

In-vitro inhibitory and bactericidal test results of the *Pithecellobium clypearia* Benth 10% ethanol extract to the ESBL-producing KPNs are shown in table K4.

The statistic analysis on in-vitro inhibitory and bactericidal $MIC_{50}$, $MIC_{90}$, $MBC_{50}$ and $MBC_{90}$ of the *Pithecellobium clypearia* Benth 10% ethanol extract to the ESBL-producing KPNs is shown in table K5 and table K6.

In-vitro inhibitory and bactericidal test results of the *Pithecellobium clypearia* Benth 60% ethanol extract to the ESBL-producing KPNs are shown in table K7.

The statistic analysis on in-vitro inhibitory and bactericidal $MIC_{50}$, $MIC_{90}$, $MBC_{50}$ and $MBC_{90}$ of the *Pithecellobium clypearia* Benth 60% ethanol extract to the ESBL-producing KPNs is shown in table K8 and table K9.

In-vitro inhibitory and bactericidal test results of the *Pithecellobium clypearia* Benth 95% ethanol extract to the ESBL-producing KPNs are shown in table K10.

The statistic analysis on in-vitro inhibitory and bactericidal $MIC_{50}$, $MIC_{90}$, $MBC_{50}$ and $MBC_{90}$ of the *Pithecellobium clypearia* Benth 95% ethanol extract to the ESBL-producing KPNs is shown in table K11 and table K12.

TABLE K1

In-vitro inhibitory and bactericidal test results of the *Pithecellobium clypearia* Benth water extract to the ESBL-producing KPNs

| Strain No. | MIC(μg/ml) | MBC(μg/ml) |
| --- | --- | --- |
| K1 | 1600 | >1600 |
| K2 | 1600 | >1600 |
| K3 | 1600 | >1600 |
| K4 | 1600 | >1600 |
| K5 | 1600 | >1600 |
| K6 | 1600 | >1600 |
| K7 | 1600 | >1600 |
| K8 | 1600 | >1600 |
| K9 | 1600 | >1600 |
| K10 | 1600 | >1600 |
| K11 | 1600 | >1600 |
| K12 | 1600 | >1600 |
| K13 | 1600 | >1600 |
| K14 | 1600 | >1600 |
| K15 | 1600 | >1600 |
| K16 | 1600 | >1600 |
| K17 | 1600 | >1600 |
| K18 | 1600 | >1600 |
| K19 | 1600 | >1600 |
| K20 | 1600 | >1600 |

TABLE K2

In-vitro inhibitory $MIC_{50}$ and $MIC_{90}$ of the *Pithecellobium clypearia* Benth water extract to the ESBL-producing KPNs

| MIC Range | $MIC_{50}$ | $MIC_{90}$ |
| --- | --- | --- |
| 1600 | 1600 | 1600 |

TABLE K3

In-vitro inhibitory $MBC_{50}$ and $MBC_{90}$ of the *Pithecellobium clypearia* Benth water extract to the ESBL-producing KPNs

| MBC Range | $MBC_{50}$ | $MBC_{90}$ |
| --- | --- | --- |
| >1600 | >1600 | >1600 |

TABLE K4

In-vitro inhibitory and bactericidal test results of the *Pithecellobium clypearia* Benth 10% ethanol extract to the ESBL-producing KPNs

| Strain No. | MIC(μg/ml) | MBC(μg/ml) |
| --- | --- | --- |
| K1 | 1600 | >1600 |
| K2 | 800 | >1600 |
| K3 | 1600 | >1600 |
| K4 | 800 | >1600 |
| K5 | 1600 | >1600 |
| K6 | 1600 | >1600 |
| K7 | 1600 | >1600 |
| K8 | 1600 | >1600 |
| K9 | 1600 | >1600 |
| K10 | 1600 | >1600 |
| K11 | 1600 | >1600 |
| K12 | 1600 | >1600 |
| K13 | 1600 | >1600 |
| K14 | 1600 | >1600 |
| K15 | 800 | >1600 |
| K16 | 800 | >1600 |
| K17 | 1600 | >1600 |
| K18 | 1600 | >1600 |
| K19 | 1600 | >1600 |
| K20 | 1600 | >1600 |

TABLE K5

In-vitro inhibitory $MIC_{50}$ and $MIC_{90}$ of the *Pithecellobium clypearia* Benth 10% ethanol extract to the ESBL-producing KPNs

| MIC Range | $MIC_{50}$ | $MIC_{90}$ |
| --- | --- | --- |
| 800-1600 | 1600 | 1600 |

TABLE K6

In-vitro inhibitory $MBC_{50}$ and $MBC_{90}$ of the *Pithecellobium clypearia* Benth 10% ethanol extract to the ESBL-producing KPNs

| MBC Range | $MBC_{50}$ | $MBC_{90}$ |
| --- | --- | --- |
| >1600 | >1600 | >1600 |

TABLE K7

In-vitro inhibitory and bactericidal test results of the *Pithecellobium clypearia* Benth 60% ethanol extract to the ESBL-producing KPNs

| Strain No. | MIC(μg/ml) | MBC(μg/ml) |
| --- | --- | --- |
| K1 | 1600 | >1600 |
| K2 | 800 | >1600 |
| K3 | 800 | >1600 |
| K4 | 800 | >1600 |
| K5 | 1600 | >1600 |
| K6 | 1600 | >1600 |
| K7 | 400 | >1600 |
| K8 | 800 | >1600 |
| K9 | 1600 | >1600 |
| K10 | 1600 | >1600 |
| K11 | 1600 | >1600 |
| K12 | 1600 | >1600 |
| K13 | 800 | >1600 |
| K14 | 800 | >1600 |
| K15 | 400 | >1600 |
| K16 | 800 | >1600 |
| K17 | 1600 | >1600 |
| K18 | 1600 | >1600 |
| K19 | 800 | >1600 |
| K20 | 800 | >1600 |

TABLE K8

In-vitro inhibitory MIC$_{50}$ and MIC$_{90}$ of the *Pithecellobium clypearia* Benth 60% ethanol extract to the ESBL-producing KPNs

| MIC Range | MIC$_{50}$ | MIC$_{90}$ |
| --- | --- | --- |
| 400-1600 | 800 | 1600 |

TABLE K9

In-vitro inhibitory MBC$_{50}$ and MBC$_{90}$ of the *Pithecellobium clypearia* Benth 60% ethanol extract to the ESBL-producing KPNs

| MBC Range | MBC$_{50}$ | MBC$_{90}$ |
| --- | --- | --- |
| >1600 | >1600 | >1600 |

TABLE K10

In-vitro inhibitory and bactericidal test results of the *Pithecellobium clypearia* Benth 95% ethanol extract to the ESBL-producing KPNs

| Strain No. | MIC(µg/ml) | MBC(µg/ml) |
| --- | --- | --- |
| K1 | 1600 | >1600 |
| K2 | 1600 | >1600 |
| K3 | 1600 | >1600 |
| K4 | 1600 | >1600 |
| K5 | 1600 | >1600 |
| K6 | 1600 | >1600 |
| K7 | 1600 | >1600 |
| K8 | 1600 | >1600 |
| K9 | 1600 | >1600 |
| K10 | 1600 | >1600 |
| K11 | 1600 | >1600 |
| K12 | 1600 | >1600 |
| K13 | 800 | >1600 |
| K14 | 800 | >1600 |
| K15 | 1600 | >1600 |
| K16 | 1600 | >1600 |
| K17 | 1600 | >1600 |
| K18 | 1600 | >1600 |
| K19 | 1600 | >1600 |
| K20 | 1600 | >1600 |

TABLE K11

In-vitro inhibitory MIC$_{50}$ and MIC$_{90}$ of the *Pithecellobium clypearia* Benth 95% ethanol extract to the ESBL-producing KPNs

| MIC Range | MIC$_{50}$ | MIC$_{90}$ |
| --- | --- | --- |
| 800-1600 | 1600 | 1600 |

TABLE K12

In-vitro inhibitory MBC$_{50}$ and MBC$_{90}$ of the *Pithecellobium clypearia* Benth 95% ethanol extract to the ESBL-producing KPNs

| MBC Range | MBC$_{50}$ | MBC$_{90}$ |
| --- | --- | --- |
| >1600 | >1600 | >1600 |

With the single use of the *Pithecellobium clypearia* Benth water extract to the ESBL-producing KPNs, the MIC$_{50}$ is 1600 µg/ml, the MIC$_{90}$ is 1600 µg/ml, and both the MBC$_{50}$ and the MBC$_{90}$ are greater than 1600 µg/ml.

With the single use of the *Pithecellobium clypearia* Benth 10% ethanol extract to the KPNs, the MIC$_{50}$ is 1600 µg/ml, the MIC$_{90}$ is 1600 µg/ml, and both the MBC$_{50}$ and the MBC$_{90}$ are greater than 1600 µg/ml.

With the single use of the *Pithecellobium clypearia* Benth 60% ethanol extract to the ESBL-producing KPNs, the MIC$_{50}$ is 1600 µg/ml, the MIC$_{90}$ is 1600 µg/ml, and both the MBC$_{50}$ and the MBC$_{90}$ are greater than 1600 µg/ml.

With the single use of the *Pithecellobium clypearia* Benth 95% ethanol extract to the ESBL-producing KPNs, the MIC$_{50}$ is 1600 µg/ml, the MIC$_{90}$ is 1600 µg/ml, and both the MBC$_{50}$ and the MBC$_{90}$ are greater than 1600 µg/ml.

What is claimed is:

1. A method of treating a disease caused by a Multi-Drug Resistant *Acinetobacter Baumanni* infection, comprising administering *Pithecellobium Clypearia* Benth Extract (EA) in combination with at least one antibiotic selected from the group consisting of imipenem, Tetracycline, Polymyxin B, Ceftazidime and Levofloxacin; and wherein the EA is a water extract or ethanol extract.

2. The method of claim 1, wherein the *Pithecellobium clypearia* Benth water extract or the *Pithecellobium clypearia* Benth ethanol extract is prepared with a following method: extracting *Pithecellobium clypearia* Benth coarse powder with water or an ethanol aqueous solution having a concentration of 10%-95% by a volume ratio, and then extracting an obtained extracting solution with ethyl acetate, in which the obtained extract is a final product.

3. The method of claim 2, wherein the ethanol aqueous solution is an ethanol aqueous solution having the concentration of 60% by the volume ratio.

* * * * *